(12) United States Patent
Aversa et al.

(10) Patent No.: US 9,821,024 B2
(45) Date of Patent: Nov. 21, 2017

(54) IMMUNOMODULATORY COMPOSITIONS

(75) Inventors: Vincenzo Aversa, Ridgewood Swords (IE); Ivan Coulter, Mount Merrion (IE); Mónica Torres Rosa, Dublin (IE); Bernard Francis McDonald, Castleblayney (IE)

(73) Assignee: Sigmoid Pharma Limited, Dublin (IE)

( * ) Notice: Subject to any disclaimer, the term of this patent is extended or adjusted under 35 U.S.C. 154(b) by 311 days.

(21) Appl. No.: 13/989,372

(22) PCT Filed: Nov. 25, 2011

(86) PCT No.: PCT/EP2011/071088
§ 371 (c)(1),
(2), (4) Date: May 23, 2013

(87) PCT Pub. No.: WO2012/069658
PCT Pub. Date: May 31, 2012

(65) Prior Publication Data
US 2013/0243873 A1    Sep. 19, 2013

(30) Foreign Application Priority Data
Nov. 25, 2010   (GB) .................................. 1020032.7

(51) Int. Cl.
| | | |
|---|---|---|
| A61K 38/13 | (2006.01) | |
| A61K 9/16 | (2006.01) | |
| A61K 9/50 | (2006.01) | |
| A61K 31/436 | (2006.01) | |
| A61K 31/502 | (2006.01) | |
| A61K 45/06 | (2006.01) | |

(52) U.S. Cl.
CPC ................ *A61K 38/13* (2013.01); *A61K 9/16* (2013.01); *A61K 9/167* (2013.01); *A61K 9/1658* (2013.01); *A61K 9/5036* (2013.01); *A61K 9/5042* (2013.01); *A61K 9/5084* (2013.01); *A61K 31/436* (2013.01); *A61K 31/502* (2013.01); *A61K 45/06* (2013.01)

(58) Field of Classification Search
CPC .............. A61K 2300/00; A61K 31/436; A61K 31/502; A61K 38/13; A61K 45/06; A61K 9/16; A61K 9/1658; A61K 9/167; A61K 9/5036; A61K 9/5042; A61K 9/5084
See application file for complete search history.

(56) References Cited

U.S. PATENT DOCUMENTS

| | | |
|---|---|---|
| 3,971,852 A | 7/1976 | Brenner et al. |
| 4,279,632 A | 7/1981 | Frosch et al. |
| 4,379,454 A | 4/1983 | Campbell et al. |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 4,891,223 A | 1/1990 | Ambegaonkar et al. |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,350,741 A | 9/1994 | Takada |
| 5,362,564 A | 11/1994 | Suzuki et al. |
| 5,385,737 A | 1/1995 | Shigeno et al. |
| 5,401,502 A | 3/1995 | Wunderlich et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |
| 5,498,439 A | 3/1996 | Bonner et al. |
| 5,500,224 A | 3/1996 | Vranckx et al. |
| 5,510,118 A | 4/1996 | Bosch et al. |
| 5,529,783 A | 6/1996 | Burke et al. |
| 5,571,533 A | 11/1996 | Santus et al. |
| 5,589,455 A | 12/1996 | Woo et al. |
| 5,645,856 A | 7/1997 | Lacy et al. |
| 5,650,232 A | 7/1997 | Glenn et al. |

(Continued)

FOREIGN PATENT DOCUMENTS

| | | |
|---|---|---|
| AU | 1977031116 | 12/1976 |
| AU | 627220 B2 | 8/1992 |

(Continued)

OTHER PUBLICATIONS

Murthy (S.N.S Murthy, et al, Treatment of Dextran Sulfate Sodium-Induced Murine Colitis by Intracolonic Cyclosporin, 38 Dig. Disease Sci. 1722 (1993)).*
Milojevic (Snezana Milojevic, et al, Amylose as a Coating for Drug Delivery to the Colon: Preparation and In Vitro Evaluation Using 5-aminosalicylic Acid Pellets, 38 J Control. Rel. 75 (1996).*
Riviere (J.E. Riviere, et al, Effects of Vasoactive Drugs on Transdermal Lidocaine Iontophoresis, 80 J Pharma. Sci. 615 (1991)).*
Loufrani (Laurent Loufrani & Daniel Henrion, Vasodilator Treatment with Hydralazine Increases Blood Flow in mdx Mice Resistance Arteries Without Vascular Wall Remodeling or Endothelium Function Impairment, 23 J Hyperten. 1855 (2005)).*
Feagan et al., "Low-Dose Cyclosporine for the Treatment of Crohn's Disease," *The New England Journal of Medicine*, 330(26):1846-1851, Jun. 30, 1994.

(Continued)

*Primary Examiner* — Snigdha Maewall
(74) *Attorney, Agent, or Firm* — Klarquist Sparkman, LLP

(57) ABSTRACT

Immunomodulator formulations for use in the treatment of disease of the GI tract. The formulations comprise a hydroxylase inhibitor and/or an immunosuppressant. Exemplary formulations comprise hydralazine as a hydroxylase inhibitor and/or cyclosporin A as an immunosuppressant.

8 Claims, 23 Drawing Sheets

(56) References Cited

U.S. PATENT DOCUMENTS

| | | |
|---|---|---|
| 5,665,386 A | 9/1997 | Benet et al. |
| 5,674,495 A | 10/1997 | Bowersock et al. |
| 5,795,590 A | 8/1998 | Kiefer et al. |
| 5,827,531 A | 10/1998 | Morrison et al. |
| 5,843,347 A | 12/1998 | Nguyen et al. |
| 5,858,401 A | 1/1999 | Bhalani et al. |
| 5,871,774 A | 2/1999 | Lemelson |
| 5,882,680 A * | 3/1999 | Suzuki et al. ............... 424/451 |
| 5,914,132 A | 6/1999 | Kelm et al. |
| 5,959,876 A | 9/1999 | Woo et al. |
| 5,961,970 A | 10/1999 | Lowell et al. |
| 6,022,562 A | 2/2000 | Autant et al. |
| 6,113,936 A | 9/2000 | Takebayashi et al. |
| 6,146,663 A | 11/2000 | Bissery et al. |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,457,339 B2 | 10/2002 | Komura |
| 6,531,150 B1 | 3/2003 | Sunohara et al. |
| 6,569,463 B2 | 5/2003 | Patel et al. |
| 6,585,997 B2 | 7/2003 | Moro et al. |
| 6,761,903 B2 | 7/2004 | Chen et al. |
| 6,923,988 B2 | 8/2005 | Patel et al. |
| 6,972,132 B1 | 12/2005 | Kudo et al. |
| 7,267,813 B2 | 9/2007 | Watanabe et al. |
| 7,374,779 B2 | 5/2008 | Chen et al. |
| 7,727,551 B2 | 6/2010 | Massironi |
| 2001/0003589 A1 | 6/2001 | Neuer et al. |
| 2001/0024658 A1 | 9/2001 | Chen et al. |
| 2002/0009457 A1 | 1/2002 | Bowersock et al. |
| 2002/0098242 A1 | 7/2002 | Darder |
| 2003/0045516 A1 | 3/2003 | Luly et al. |
| 2003/0055028 A1 | 3/2003 | Stergiopoulos et al. |
| 2003/0078194 A1 | 4/2003 | Cho et al. |
| 2003/0104048 A1 | 6/2003 | Patel et al. |
| 2003/0124061 A1 | 7/2003 | Roberts |
| 2003/0180352 A1 | 9/2003 | Patel et al. |
| 2003/0193102 A1 | 10/2003 | Yan |
| 2003/0232076 A1 | 12/2003 | Makino et al. |
| 2003/0235595 A1 | 12/2003 | Chen et al. |
| 2004/0028619 A1 | 2/2004 | Watanabe et al. |
| 2004/0029855 A1 | 2/2004 | Klaveness et al. |
| 2004/0062802 A1 | 4/2004 | Hermelin |
| 2004/0126428 A1 | 7/2004 | Hughes et al. |
| 2004/0258701 A1 | 12/2004 | Dominowski et al. |
| 2005/0095288 A1 | 5/2005 | Honea |
| 2005/0249807 A1 | 11/2005 | Brown et al. |
| 2006/0018965 A1 | 1/2006 | Moodley et al. |
| 2006/0034937 A1* | 2/2006 | Patel ............................. 424/497 |
| 2006/0135441 A1 | 6/2006 | Khodadoust et al. |
| 2006/0222701 A1 | 10/2006 | Kulkarni et al. |
| 2007/0154554 A1 | 7/2007 | Burgermeister et al. |
| 2007/0292523 A1 | 12/2007 | Moodley et al. |
| 2008/0020018 A1 | 1/2008 | Moodley et al. |
| 2008/0107694 A1 | 5/2008 | Trogden et al. |
| 2008/0113031 A1* | 5/2008 | Moodley et al. ............. 424/490 |
| 2008/0124279 A1 | 5/2008 | Andremont et al. |
| 2008/0311201 A1 | 12/2008 | Der-Yang et al. |
| 2008/0318912 A1 | 12/2008 | Fox et al. |
| 2010/0136105 A1 | 6/2010 | Chen et al. |
| 2010/0215737 A1 | 8/2010 | Coulter |
| 2010/0239665 A1 | 9/2010 | Coulter |
| 2010/0255087 A1 | 10/2010 | Coulter |
| 2010/0297221 A1 | 11/2010 | Coulter |
| 2011/0052645 A1 | 3/2011 | Coulter |
| 2012/0141531 A1 | 6/2012 | Coulter et al. |
| 2012/0141585 A1 | 6/2012 | Coulter et al. |

FOREIGN PATENT DOCUMENTS

| | | |
|---|---|---|
| CA | 2170748 | 3/1995 |
| CA | 2376261 | 6/2000 |
| CN | 1557283 | 12/2004 |
| EP | 0 348 910 | 6/1989 |
| EP | 0 396 425 | 11/1990 |
| EP | 0 525 731 | 2/1993 |
| EP | 0 550 067 | 7/1993 |
| EP | 0 621 775 | 11/1994 |
| EP | 0 650 721 | 5/1995 |
| EP | 0694308 | 1/1996 |
| EP | 0 760 237 | 3/1997 |
| EP | 0 778 083 | 6/1997 |
| EP | 0813876 | * 12/1997 |
| EP | 0 922 451 | 6/1999 |
| EP | 0 813 876 | 3/2002 |
| EP | 0 789 561 | 4/2004 |
| GB | 2257359 | 1/1993 |
| GB | 2391473 | 2/2004 |
| JP | A-58 013508 | 1/1983 |
| JP | A-58 077810 | 5/1983 |
| JP | 59-088420 | 5/1984 |
| JP | A-61 151119 | 7/1986 |
| JP | H0549899 A | 3/1993 |
| JP | 7247215 A | 9/1995 |
| JP | 2000-247911 | 9/2000 |
| JP | 2000-302654 | 10/2000 |
| JP | 64 000015 | 8/2010 |
| WO | WO 93/00063 | 1/1993 |
| WO | WO 94/15636 | 7/1994 |
| WO | WO 96/36322 | 11/1996 |
| WO | WO 97/02017 | 1/1997 |
| WO | WO 97/02042 | 1/1997 |
| WO | WO 98/18610 | 5/1998 |
| WO | WO 98/40051 | 9/1998 |
| WO | WO 98/50018 | 11/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 00/33862 | 6/2000 |
| WO | WO 00/69420 | 11/2000 |
| WO | WO 01/08666 | 2/2001 |
| WO | WO 01/32142 | 5/2001 |
| WO | WO 01/37808 | 5/2001 |
| WO | WO 01/51008 | 7/2001 |
| WO | WO 03/018134 | 3/2003 |
| WO | WO 03/020243 | 3/2003 |
| WO | WO 03/030878 | 4/2003 |
| WO | WO 03/053404 | 7/2003 |
| WO | WO 03/056938 | 7/2003 |
| WO | WO 03/092741 | 11/2003 |
| WO | WO 2004/022220 | 3/2004 |
| WO | WO 2004/042024 | 5/2004 |
| WO | WO 2004/064997 | 8/2004 |
| WO | WO 2004/084870 | 10/2004 |
| WO | WO 2004/108121 | 12/2004 |
| WO | WO 2005/020994 | 3/2005 |
| WO | WO 2005/030205 | 4/2005 |
| WO | WO 2005/048998 | 6/2005 |
| WO | WO 2005/072088 | 8/2005 |
| WO | WO 2005/074913 | 8/2005 |
| WO | WO 2005/100454 | 10/2005 |
| WO | WO 2006/026592 | 3/2006 |
| WO | WO 2006/035416 | 4/2006 |
| WO | WO 2006/110802 | 10/2006 |
| WO | WO 2007/012478 | 2/2007 |
| WO | WO 2007/014445 | 2/2007 |
| WO | WO 2007/018943 | 2/2007 |
| WO | WO 2007/095092 | 8/2007 |
| WO | WO 2008/122965 | 10/2008 |
| WO | WO 2008/122967 | 10/2008 |
| WO | WO 2009/002533 | 12/2008 |
| WO | WO 2010/005980 | 1/2010 |

(56) References Cited

OTHER PUBLICATIONS

French et al., "Evaluation of the Physiochemical Properties and Dissolution Characteristics of Mesalamine: Relevance to Controlled Intestinal Drug Delivery," *Pharmaceutical Research* 10(9):1285-1290, 1993.

Van Deventer, "Small therapeutic molecules for the treatment of inflammatory bowel disease", *Gut* 50(Suppl III): iii47-iii53, 2002.

Drug Bank, www.drugbank.ca/drugs/DB00244, 12 pages.

Malaekeh-Nikouei et al. "Preparation, Characterization, and Mucoadhesive Properties of Chitosan-Coated Microspheres Encapsulated with Cyclosporine A," *Drug Development and Industrial Pharmacy*, 34:492-498, 2008.

Rutgeerts et al., "A comparison of Budesonide with Prednisolone for Active Crohn's Disease," *The New England Journal of Medicine*, 331(13): 842-845, 1994.

Wakerly et al., "Pectin/Ethylcellulose Film Coating Formulations for Colonic Drug Delivery," Pharmaceutical Research, 13(8): 1210-1212, 1996.

Dhara et al., "Stability of Sodium Dodecyl Sulfate Micelles in the Presence of a Range of Water-Soluble Polymers: A Pressure-Jump Study," *J. Phys. Chem. B.*, 105: 7153-7138; 2001.

Greener et al., "Interaction of Anionic Surfactants with Gelatin: Viscosity Effects," *Macromolecules*, 20: 2490-2498: 1987.

Holmberg e al., *Surfactants and Polymers in Aqueous Solution*. John Wiley & Sons, Ltd. 2002.

Muller et al. "Competitive Adsorption of Gelatin and Sodium Dodecylbenzenesulfonate at Hydrophobic Surfaces," *Langmuir*, 14: 3107-3114; 1998.

Wesley- et al., "Structure of Polymer/Surfactant Complexes Formed by Poly(2-(dimethylamino)ethyl metharylate) and Sodium Dodecyl Sulfate," *Langmuir* 18: 5704-5707: 2002.

International Search Report from PCT Application No. PCT/EP2011/0710888 dated May 29, 2012.

Fukata et al. "The effective therapy of cyclosporine A with drug delivery system in experimental colitis," *Journal of Drug Targeting*, 19(6): 458-467, 2011.

Sharkey et al. "The use of Cyclosporin A in acute steroid-refractory ulcerative colitis: Long term outcomes," *Journal of Crohn's and Colitis*, 5: 91-94, 2011.

Al-Meshal et al., "Oral administration of liposomes containing cyclosporine: a pharmacokinetic study," *International Journal of Pharmaceutics* 168:163-168, 1998.

Anderberg et al., "Sodium Caprate Elicits Dilatations in Human Intestinal Tight Junctions and Enhances Drug Absorption by the Paracellular Route," *Pharmaceutical Research* 10(6):857-864, 1993.

Barnes et al., "Theophylline: New Perspectives for an Old Drug," *AM J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Cannon, "Oral Solid Dosage Forms of Lipid-based Drug Delivery Systems," *AM Pharm Rev* 8(1):108-115, 2005.

Chourasia et al., "Pharmaceutical approaches to colon targeted drug delivery systems," *J Pharm. Pharmaceut. Sci.* 6(1):33-66-2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Cummins et al., "The Hydroxylase Inhibitor Dimethyloxalylglycine is Protective in a Murine Model of Colitis," *Gastroenterology* 134:156-165, 2008.

Downs, "The gastrointestinal tract and HIV pathogenesis," *S. Afr. J Clin. Nutr.* 23(1):Supplement:S65-S68, 2010.

Drewe et al., "The absorption site of cyclosporine in the human gastro-intestinal tract," *Br. J clin. Pharmac.* 33:39-43, 1992.

Gao et al., "Physiochemical characterization and evaluation of a microemulsion system for oral delivery of yclosporine A," *International Journal of Pharmaceutics* 161:75-86, 1998.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

Madene et al., "Flavour encapsulation and controlled release—a review," *International Journal of Food Science and Technology* 41:1-21, 2006.

Manakova et al., "Failure of FK506 (tacrolimus) to alleviate apomorphine-induced circling in rat Parkinson model in spite of some cytoprotective effects in SH-SYSY dopaminergic cells," *Brain Research* 1038:83-91, 2005.

McGinity et al., Aqueous Polymeric Coatings for Pharmaceuticals Dosage Forms, *Marcel Dekker, Inc.*, 1997.

Miller et al., "Controlled Trial of Nimodipine in Amyotrophic Lateral Sclerosis," *Neuromusc. Disord.*, 6(2):101-104, 1996.

Milojevic et al., "Amylose as a coating for drug delivery to the colon: Preparation and in vitro evaluation using 5-aminosalicylic acid pellets," *Journal of Controlled Release* 38:75-84, 1996.

Mohan et al., "Focused Examination of the Intestinal lamina Propria Yields Greater Molecular Insight into Mechanisms Underlying SIV Induced Immune Dysfunction," *PLoS One* 7(4):e34S61, Apr. 12, 2012.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Ribeiro et al., "Microencapsulation of lipophilic drugs in chitosan-coated alginate microspheres," *International Journal of Pharmaceutics* 187:115-123, 1999.

Rieder et al., "Wound Healing and Fibrosis in Intestinal Disease," *Gut* 56:130-139, 2007.

Rodriguez et al., "Colonic budesonide delivery from ph-dependent microcapsules containing lipidic cores," *Acta Technologiae et Legis Medicamenti* 11(1):45-52, 2000.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Suzuki et al., "Analysis of intestinal fibrosis in chronic colitis in mice induced by dextran sulfate sodium," *Pathology International* 61:228-238, 2011.

Sweetman and Martindale, "Nimodipine," *Cardiovascular Drugs* p. 946, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9):903-906, 2003.

Zuber et al., "Reversible cerebral angiopathy," *J. Neurol* 253:1585-1588, 2006.

Xu et al. "Structure Evolution of Gelatin Particles Induced by pH and Ionic Strength," *Microscopy Research and Technique*, 79:272-281, 2013.

Xu et al. "Effect of anionic surfactants on grafting density of gelatin modified with PDMS-E," *Colloids and Surfaces B: Biointerfaces*, 144:310-315, 2014.

Shioji, Yusaku "Manufacturing technology of solid formulation", CMC Publishing Co. Ltd., pp. 46-48 and 174-177, Jan. 27, 2003.

Office action issued for Japanese Patent Application No. 2006-507572.

(56) References Cited

OTHER PUBLICATIONS

Sandborn et al. "The Pharmacokinetics and Colonic Tissue Concentration of Cyclosporine After IV, Oral, and Enema Administration," *J. Clin. Pharmacol.* 31: 76-80, 1991.
LABRAFIL® M1944CS, http://www.gattefosse.com/en/applications/labrafil-m1944cs.html, accessed Dec. 10, 2015.
Strickley, "Solubilizing Excipients in Oral and Injectable Formulations," *Pharmaceutical Research*, 21(2): 201-230, Feb. 2004.
Cannon et al., "Chapter 11: Emulsions, Microemulsions, and Lipid-Based Drug Delivery Systems for Drug Solubilization and Delivery—Part II: Oral Applications," *Water-Insoluble Drug Formulation: Second Edition*, CRC Press, pp. 227-254, 2008.
Date et al., "Self-nanoemulsifying drug delivery systems: formulation insights, applications and advances," *Nanomedicine*, 5(10): 1595-1616, Dec. 2010.
Gibson, "Lipid-Based Excipients for Oral Drug Delivery: Chapter 2," *Oral Lipid-Based Formulations: Enhancing the Bioavailability of Poorly Water-Soluble Drugs*, CRC Press, pp. 33-61, 2007.
Liu et al., "Chapter 12: Micellization and Drug Solubility Enhancement," *Water-Insoluble Drug Formulation: Second Edition*, CRC Press, pp. 255-272, 2008.
Onoue et al., "Inhalable dry-emulsion formulation of cyclosporine A with improved anti-inflammatory effects in experimental asthma/COPD-model rats," *European Journal of Pharmaceutics and Biopharmaceutics*, vol. 80, pp. 54-60, Oct. 8, 2011.
Keck, "Cyclosporine Nanosuspensions: Optimised Size Characterisation & Oral Formulations," Doctoral Dissertation submitted at Freien Universitat Berlin, 2006.

\* cited by examiner

IMMUNOMODULATORY COMPOSITIONS

CROSS REFERENCE TO RELATED APPLICATIONS

This is the U.S. National Stage of International Application No. PCT/EP2011/071088, filed Nov. 25, 2011, which was published in English under PCT Article 21(2), which in turn claims the benefit of Great Britain Application No. 1020032.7, filed Nov. 25, 2010. The Great Britain application is incorporated herein in its entirety.

This invention relates to immunomodulatory compositions and to therapeutic methods using immunomodulatory compositions. The invention also relates to methods of making the compositions, methods of using them, and other subject matter.

BACKGROUND

Disorders of the intestine, disorders of the colon, and disorders associated with or suspected of being associated with a dysfunctional intestine and/or dysfunctional colon, are an unmet medical need. The present invention comprises products, methods and uses which are useful in relation to treating such disorders.

More particularly, inflammatory Bowel Disease (IBD), which includes ulcerative colitis and Crohn's Disease, is a common disease with severe morbidity and an extremely limited therapeutic repertoire. In most cases, surgical intervention is necessary due to the failure of successful pharmacologic intervention. Improved therapy for IBD is therefore extremely desirable.

Current pharmacologic therapy for IBD is limited to steroids, sulfasalizine and TNF antibodies all of which have significant limitations due to side effects caused by the high levels of systemic administration that must be given to achieve therapeutic effects. The underlying causes of inflammatory bowel disease are not clearly understood but the symptoms have been treated through the use of anti-inflammatory agents that often are not specific and lead to serious side effects, especially if administered chronically. In addition to being toxic, most current anti-inflammatory therapeutics have limited solubility, permeability or stability resulting in high drug doses, frequent administration or administered by injection or suppositories, thus therapeutic options in IBD are very limited. Hydroxylase inhibitors have a potential role in the treatment of IBD. See The Hydroxylase Inhibitor Dimethyloxalylglycine Is Protective in a Murine Model of Colitis *Gastroenterology, Volume* 134, *Issue* 1, January 2008, Pages 156-165.e1. Eoin P. Cummins, Fergal Seeballuck, Stephen J. Keely, Niamh E. Mangan, John J. Callanan, Padraic G. Fallon, Cormac T. Taylor.

A permeable ("leaky") intestinal epithelial barrier has been implicated in intestinal and extraintestinal diseases. Examples of such diseases are the intestinal diseases inflammatory bowel disease, celiac disease, Crohn's disease, ulcerative colitis, GI-GVHD, gastroenteritis, duodenitis, jejunitis, ileitis, peptic ulcer, Curling's ulcer, appendicitis, colitis, pseudomembraneous colitis, irritable bowel syndrome including Irritable bowel syndrome-diarrhea predominant (IBS-D), irritable bowel syndrome-constipation predominant (IBS-C) and irritable bowel syndrome-mixed (IBS-M); diverticulosis, diverticulitis and endometriosis.

Extraintestinal disorders in which a leaky intestinal epithelial barrier have been implicated include rheumatic disorders, rheumatoid arthritis, temporomandibular joint syndrome, type 1 diabetes, multiple sclerosis, atopic dermatitis, psoriasis, a chronic pain syndrome, fibromyalgia, chronic fatigue syndrome, depressive disorders, affective disorders and attention disorders, colorectal carcinoma, adenocarcinoma, and chronic heart failure.

For example, the reader is referred to Vaarala O, Atkinson M A, Neu J (October 2008). "The "perfect storm" for type 1 diabetes: the complex interplay between intestinal microbiota, gut permeability, and mucosal immunity". Diabetes 57 (10): 2555-62; Liu Z, Li N, Neu J (April 2005). "Tight junctions, leaky intestines, and pediatric diseases". Acta Paediatr. 94 (4): 386-93; Maes M. Inflammatory and oxidative and nitrosative stress pathways underpinning chronic fatigue, somatization and psychosomatic symptoms. Curr Opin Psychiatry. 2009 January; 22(1):75-83; de Magistris L, Familiari V, Pascotto A, Sapone A, Frolli A, Iardino P, Carteni M, De Rosa M, Francavilla R, Riegler G, Militerni R, Bravaccio C. Alterations of the intestinal barrier in patients with autism spectrum disorders and in their first-degree relatives. J Pediatr Gastroenterol Nutr. 2010 October; 51(4):418-24; Sandek A, Rauchhaus M, Anker S D, von Haehling S (September 2008). "The emerging role of the gut in chronic heart failure". Curr Opin Clin Nutr Metab Care 11 (5): 632-9; Terjung B, Spengler U (February 2009). "Atypical p-ANCA in PSC and AIH: a hint toward a "leaky gut"?". Clin Rev Allergy Immunol 36 (1): 40-51; Intestinal mucosal permeability in inflammatory rheumatic diseases. II. Role of disease. Mielants H, De Vox M, Goemaere S, Schelstraete K, Cuvelier C, Goethals K, Maertens M, Ackerman C, Veys E M, J. Rheumatol. 1991 March; 18(3):394-400; Intestinal mucosal permeability in inflammatory rheumatic diseases. I. Role of antiinflammatory drugs. Mielants H, Goemaere S, De Vos M, Schelstraete K, Goethals K, Maertens M, Ackerman C, Veys E M. J. Rheumatol. 1991 March; 18(3):389-93; Intestinal permeability and atopic disease. MacKie R M. Lancet. 1981 Jul. 18; 2(8238):155.

The reader is referred to a recent review by Andy Wullaert, Marion C Bonnet and Manolis Pasparakis in Cell Research (2011) 21:146-158 for an understanding of the role of NF-κB in the regulation of epithelial homeostasis and inflammation, and this publication and all the references mentioned in it are included herein by reference in their entirety. In summary, a number of in vivo studies in genetic mouse models over the past years have revealed that NF-κB inhibition can also trigger chronic inflammatory conditions. This function of NF-κB appears to be particularly important at epithelial surfaces, where NF-κB activity in epithelial cells is required for the maintenance of immune homeostasis. Therefore, proper regulation of NF-κB activation at epithelial interfaces is crucial for the maintenance of physiological tissue homeostasis and for efficient host defense against environmental insults. NF-κB inhibition sensitizes epithelial cells to stress-inducing stimuli coming either from the environment (e.g., microorganisms) or from immune cells (e.g., cytokines) and compromises their viability resulting in the deregulation of tissue immune homeostasis and triggering inflammation. Moreover, NF-κB is known to protect cells from a wide variety of cell death triggers.

A number of studies have showed that inhibition of NF-κB activation specifically in the intestinal epithelium causes severe intestinal inflammation. Thus, mice lacking NF-κB signaling protein NEMO specifically in intestinal epithelial cells (IECs) developed severe chronic colitis characterized by epithelial ulceration, elevated expression of proinflammatory mediators and infiltration of immune cells. Complete abrogation of canonical NF-κB activity in the intestinal epithelium, achieved by ablation of NEMO (or by combined deficiency of both IKK1 and IKK2), caused severe colon inflammation, demonstrating that IKK/NF-κB signaling performs essential homeostasis-preserving functions in the colonic epithelium. Patients carrying hypomorphic mutations in NEMO usually suffer from severe immunodeficiency and developmental skin defects, but some of these patients also develop colitis. Interestingly, hematopoietic stem cell transplantation (HSCT) is effective in treating the immunodeficiency, but does not improve the colitis phenotype. On the contrary, HSCT often worsens pre-existing colitis or even triggers colon inflammation in patients who did not suffer from it before transplantation, suggesting that impaired NF-κB signaling in non-hematopoietic cells is responsible for colitis development. It would therefore be desirable to up-regulate NF-κB activity in subjects who would benefit therefrom, for example in patients who suffer from or have suffered from inflammatory orders of the GI tract, for example those suffering from graft-versus host disease following HSCT.

BRIEF SUMMARY OF THE DISCLOSURE

This specification contains data indicating that combination therapy with hydralazine and cyclosporin A, particularly where the proportion of hydralazine is not too low, has potential for prophylactic and therapeutic treatment of disorders of the gastrointestinal tract. See in particular Examples 1-3 and 6-9. In one aspect, therefore, the invention provides a product comprising hydralazine and cyclosporin A in a weight ratio (hydralazine:cyclosporin) of from 1:10 to 10:1. The weight ratio may be: from 1:5 to 5:1; from 1:2 to 5:1; from 1:2 to 2:1; from 0.5:1 to 5:1; or from 0.5:1 to 2:1. The weight ratio may be from 0.8:1 to 5:1, e.g. from 0.8:1 to 2:1 or from 0.8:1 to 1.5:1. The weight ratio may be from 1:1 to 5:1 or from 1:1 to 2:1, e.g. from 1:1 to 1.5:1. The weight ratio may be at least 1.1:1, e.g. from 1.1:1 to 2:1 or from 1.1:1 to 1.5:1.

The product may be a pharmaceutical composition for oral administration. Advantageously, the cyclosporin A is dissolved. Cyclosporin A is poorly soluble in water and more soluble in a hydrophobic environment; the pharmaceutical composition may therefore comprise a hydrophobic phase in which the cyclosporin is dissolved. The pharmaceutical composition may be a multiple minibead composition wherein the hydralazine and cyclosporin A are contained in the minibeads, each minibead comprising a water-soluble polymer matrix material and, dispersed within the matrix material, the hydrophobic phase, the hydralazine being comprised in the matrix material. The matrix material may comprise a hydrophilic surfactant having an HLB value of at least 15 and the hydrophobic phase comprises a non-ionic surfactant having an HLB value of at least 10 but less than that of the hydrophilic surfactant.

The pharmaceutical composition may be adapted for at least a portion of each of the hydralazine and the cyclosporin to be released in the colon.

Included in the invention are pharmaceutical compositions wherein at least some of the minibeads have a controlled release coating adapted for the coated minibeads to release hydralazine and cyclosporin in the colon. The coated minibeads may be coated with a coating comprising a pH independent polymer and a polymer specifically susceptible of degradation by bacterial enzymes in the colon. The pH independent polymer may be ethylcellulose and the polymer specifically susceptible of degradation by bacterial enzymes in the colon may be pectin.

The pharmaceutical composition may be for use in a therapy selected from: maintaining the health of the gastrointestinal tract, restoring or improving the health of the gastrointestinal tract and delaying the progression of a disorder of the gastrointestinal tract. The pharmaceutical composition my be for use in treating, or delaying the progression of, a disorder selected from intestinal disorders which are inflammatory and/or fibrotic, or is for use in maintenance therapy of a patient who has suffered from or is suffering from such a disorder. The disorder may be selected from celiac disease, HIV or another enteropathy, pouchitis, cachexia, or the composition may be for use in preventing or reducing chemotherapy-induced or radiation therapy-induced gastrointestinal insult and inflammatory bowel disease, and combinations thereof. Celiac disease is primarily a disorder of the small intestine and, for treatment of this disease, formulations are suitably adapted to release active in the small intestine, e.g. minicapsules include an enteric barrier or coating for dissolution in the small intestine, for example in the duodenum. However, celiac disease may also manifest itself in the colon as microscopic colitis and IBD. Further, patients suffering from celiac disease suffer an increased risk of also suffering from ulcerative colitis. It will therefore often be beneficial for celiac patients to have the actives described herein delivered to the colon as well as the small intestine. The invention therefore provides combination formulations comprising hydralazine and cyclosporin A which are for use in delivery of the actives in the small intestine and for use in combination with a combination formulation comprising hydralazine and cyclosporin A for us in delivery of the actives in the colon. The two different combination formulations may be administered simultaneously, sequentially or separately. For example, a unit dosage, e.g. a capsule, may comprise a first population of hydralazine/cyclosporin minicapsules having a controlled release coating to release the active in the small intestine and a second population of hydralazine/cyclosporin minicapsules having a controlled release coating to release the actives in the colon. See below for more about coatings. The second population may constitute no more than 50% of minibeads in the unit dosage form, e.g. at least 10% or at least 20% and no more than 30% or 40%, for example from 20%-40% or 10%-30%.

It will be appreciated that the invention also includes an active agent selected from (i) hydralazine and (ii) cyclosporin A for oral administration with the other of (i) and (ii) in a ratio as above. Also provided is an active agent selected from (i) hydralazine and (ii) cyclosporin A for use in oral combination therapy with the other in a ratio as above. The two actives may be administered simultaneously, sequentially or separately, e.g. each in a separate formulation as described herein. The active agent may be for use in a method of treatment described above in relation to the product of the first aspect of the invention or for use in a method of treatment described elsewhere herein. Each active agent may be comprised in a multiple minibead formulation as described elsewhere herein.

This specification also contains data indicating that combination therapy with an immunosuppressant and a hydroxylase inhibitor has potential for the therapeutic and prophylactic treatment of fibrotic intestinal orders. See in particular examples 6 and 7. In a second aspect, therefore, the invention provides a pharmaceutical composition comprising an immunosuppressant and a hydroxylase inhibitor and for use in treating, or delaying the progression, of a fibrotic intestinal disorder, or for use in maintenance therapy of a patient who has suffered from or is suffering from a fibrotic intestinal disorder. The disorder may be selected from celiac disease and HIV enteropathy. The disorder may be another enteropathy, e.g. one disclosed herein.

See above for a discussion about the treatment of celiac disease with hydralazine and cyclosporin A. That discussion applies mutatis mutandis to formulations comprising a combination of an immunosuppressant and a hydroxylase inhibitor. HIV enteropathy is likely to occur widely throughout the intestinal tract and therapies will typically involve simultaneous, separate or sequential administration of at least two combination formulations for use in releasing their actives in respective different parts of the GI tract, e.g. at least in a part of the small intestine and at least in the colon. A multiple minibead unit dosage form, e.g. capsule, may therefore include at least two populations of minibeads, each for use in releasing their contained actives in a respective different part of the GI tract, e.g. at least a population to release the actives in a part of the small intestine (for example duodenum) and a population to release the actives in the ileum and/or colon. See below for more about targeted release and coatings therefor.

This paragraph applies to all aspects and implementations of the disclosure. The immunosuppressant may be selected from, or comprise, cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides. The hydroxylase inhibitor may be selected from, or comprise, DMOG, hydralazine, FG-4497, FG4095, AGN-2979, metirosine, 3-iodotyrosine, aquayamycin, bulbocapnine, oudenone, TM 6008, TM 6089, siRNAs against hydroxylases and antisense therapeutics against hydroxylases, e.g. against PHD1, or a combination thereof.

In the second aspect, the immunosuppressant may be cyclosporin A and/or the hydroxylase inhibitor may be hydralazine, e.g. it may be the case that the immunosuppressant is cyclosporin and the hydroxylase inhibitor is hydralazine. The composition may comprise cyclosporin A and hydralazine in a hydralazine:cyclosporin weight ratio as mentioned in relation to the first aspect, e.g. from 0.8:1 to 2:1.

In the second aspect the pharmaceutical composition may comprise a hydrophobic phase in which the immunosuppressant is dissolved; in particular the immunosuppressant may be a macrolide immunosuppressant. The pharmaceutical composition may be a multiple minibead composition wherein the immunosuppressant and the hydroxylase inhibitor are contained in the minibeads, each minibead comprising a water-soluble polymer matrix material and, dispersed within the matrix material, the hydrophobic phase. The hydroxylase inhibitor may be hydralazine or another water soluble drug and be comprised in the matrix material. The matrix material may comprise a hydrophilic surfactant having an HLB value of at least 15 and the hydrophobic phase comprises a non-ionic surfactant having an HLB value of at least 10 but less than that of the hydrophilic surfactant.

The pharmaceutical composition of the second aspect may be adapted for at least a portion of each of the immunosuppressant and the hydroxylase inhibitor to be released in the colon.

In the multiple minibead compositions of the second aspect, at least some of the minibeads have a controlled release coating adapted for the coated minibeads to release the hydroxylase inhibitor and the immunosuppressant in the colon. The coated minibeads may be coated with a coating comprising a pH independent polymer and a polymer specifically susceptible of degradation by bacterial enzymes in the colon. The pH independent polymer may be ethylcellulose and/or the polymer specifically susceptible of degradation by bacterial enzymes in the colon may be pectin.

The invention also includes an active agent selected from (i) an immunosuppressant and (ii) a hydroxylase inhibitor for administration with the other of (i) and (ii) and for use in treating, or delaying the progression, of a fibrotic intestinal disorder, or for use in maintenance therapy of a patient who has suffered from or is suffering from a fibrotic intestinal disorder. Also provided is an active agent selected from (i) an immunosuppressant and (ii) a hydroxylase inhibitor for use in oral combination therapy with the other and for use in treating, or delaying the progression, of a fibrotic intestinal disorder, or for use in maintenance therapy of a patient who has suffered from or is suffering from (e.g. continues to suffer from) a fibrotic intestinal disorder. The two actives may be administered simultaneously, sequentially or separately, e.g. each in a separate formulation as described herein. Each active agent may be comprised in a multiple minibead formulation as described elsewhere herein. The active agent may be comprised in a pharmaceutical composition comprising the immunosuppressant and the hydroxylase inhibitor and for use in treating, or delaying the progression, of a fibrotic intestinal disorder, or for use in maintenance therapy of a patient who has suffered from or is suffering from a fibrotic intestinal disorder. At least a portion of each of the immunosuppressant and the hydroxylase inhibitor may be released in the colon, each may therefore be included in a formulation adapted for at least a portion of its contained active to be released in the colon; suitably the formulation is a multiple minibead formulation wherein at least some of the minibeads have a controlled release coating adapted for the coated minibeads to release their active agent in the colon; such minibead formulations are described in more detail elsewhere herein.

This specification contains data indicating that hydroxylase inhibitors are effective to up-regulate activity of NF-κB but in monotherapy may not be effective to bring under control an existing inflammatory condition of the GI tract. See in particular Example 8. The data support a role for hydroxylase inhibitors in maintenance therapy, in subjects who previously had treatment to bring an inflammatory condition of the GI tract under control and might benefit from therapy, for example to maintain somewhere around their existing level of GI tract health. Maintenance therapy may control the symptoms of the disorder, e.g. stop, delay or reduce a worsening of symptoms. Accordingly, in a third aspect, there is provided a hydroxylase inhibitor for use in maintenance therapy of a patient who has suffered from or is suffering from an inflammatory intestinal disorder. The disorder may be selected from (i) inflammatory bowel disease and (ii) graft-versus-hose disease following hematopoietic stem cell transplantation. The disorder may be colitis.

The hydroxylase inhibitor may be selected from those listed previously, e.g. it may be hydralazine.

The hydroxylase inhibitor of the third aspect may be in solution phase in a pharmaceutical composition. The hydroxylase inhibitor may be sufficiently water-soluble for adequate drug loading with the inhibitor in the solution phase. The hydroxylase inhibitor may be sparingly soluble in water but more commonly is at least soluble and may be freely soluble or very soluble, as these terms are defined herein. The pharmaceutical composition may be a multiple minibead composition, the minibeads comprising a water soluble polymer matrix in which a water hydroxylase inhibitor is in solid solution. The minibeads may further comprise a hydrophobic phase dispersed in the matrix, the hydrophobic phase being formed of material liquid at body temperature. The pharmaceutical composition may be adapted for at least a portion of the hydroxylase inhibitor to be released in the colon. The hydroxylase inhibitor is not required to be in the solution phase, e.g. it may be in the form of micro- or nano-particles, in particular such a particulate hydroxylase inhibitor may be included in a water soluble polymer matrix if it is soluble, freely soluble or very soluble in water.

In the multiple minibead composition of the third aspect, at least some of the minibeads may have a controlled release coating adapted for the coated minibeads to release hydralazine in the colon. The coated minibeads may be coated with a coating comprising a pH independent polymer and a polymer specifically susceptible of degradation by bacterial enzymes in the colon. The pH independent polymer may be ethylcellulose and/or the polymer specifically susceptible of degradation by bacterial enzymes in the colon may be pectin.

According to a further aspect of the invention, there is provided a combination of actives or a composition as defined herein for use in a method of treatment of the human or animal body by therapy or prophylaxis.

The invention therefore provides a method of treating a warm-blooded animal e.g. a mammal, such as a human, to maintain the health of the gastrointestinal tract, to restore or improve the health of the gastrointestinal tract and/or to delay the progression of a disorder of the gastrointestinal tract, which method comprises orally administering to said animal simultaneously, sequentially or separately hydralazine and cyclosporin A in a weight ratio (hydralazine:cyclosporin) of from 1:10 to 10:1, e.g. 1:5 to 5:1, for example 0.8:1 to 5:1. Particular embodiments of this method comprise the administration of a composition according to any of the composition embodiments described herein. The composition may be administered in a therapeutically effective amount or in a prophylactically effective amount.

The invention therefore provides a method of treating a warm-blooded animal e.g. a mammal, such as a human, to treat, or delay the progression of, a disorder selected from intestinal disorders which are inflammatory and/or fibrotic, or for use in maintenance therapy of an animal who has suffered from or is suffering from such a disorder, which method comprises orally administering to said animal simultaneously, sequentially or separately hydralazine and cyclosporin A in a weight ratio (hydralazine:cyclosporin) of from 1:10 to 10:1 e.g. 1:5 to 5:1, for example 0.8:1 to 5:1. Particular embodiments of this method comprise the administration of a composition according to any of the composition embodiments described herein. The composition may be administered in a therapeutically effective amount or in a prophylactically effective amount. In particular, the disorder is selected from celiac disease, HIV and other enteropathies and inflammatory bowel disease, and combinations thereof.

The invention therefore provides a method of treating a disorder selected from celiac disease, HIV enteropathy and inflammatory bowel disease, and combinations thereof, in a warm-blooded animal e.g. a mammal, such as a human, which method comprises orally administering to said animal simultaneously, sequentially or separately hydralazine and cyclosporin A in a weight ratio (hydralazine:cyclosporin) of from 1:10 to 10:1 e.g. 1:5 to 5:1, for example 0.8:1 to 5:1. Particular embodiments of this method comprise the administration of a composition according to any of the composition embodiments described herein. The composition may be administered in a therapeutically effective amount or in a prophylactically effective amount.

There is therefore provided a method of treating a warm-blooded animal e.g. a mammal, such as a human, to treat, or delay the progression, of a fibrotic intestinal disorder, or for maintenance therapy of an animal which has suffered from or is suffering from a fibrotic intestinal disorder, which method comprises orally administering to said animal simultaneously, sequentially or separately an immunosuppressant and a hydroxylase inhibitor. Particular embodiments of this method comprise the administration of a composition according to any of the composition embodiments described herein. The composition may be administered in a therapeutically effective amount or in a prophylactically effective amount. In particular the disorder is selected from celiac disease and HIV enteropathy.

The invention therefore provided a method of treating a disorder selected from celiac disease and HIV enteropathy in a warm-blooded animal e.g. a mammal, such as a human, which method comprises administering to said animal simultaneously, sequentially or separately an immunosuppressant and a hydroxylase inhibitor. Particular embodiments of this method comprise the administration of a composition according to any of the composition embodiments described herein. The composition may be administered in a therapeutically effective amount or in a prophylactically effective amount.

According to a further aspect of the invention, there is provided a hydroxylase inhibitor as described herein for use in the method of treatment of the human or animal body by therapy or prophylaxis. In particular the treatment is maintenance therapy.

There is therefore provided a method for maintenance therapy of a warm-blooded animal e.g. a mammal, such as a human, which has suffered from or is suffering from an inflammatory intestinal disorder, which method comprises administered to said animal a hydroxylase inhibitor. Particular embodiments of this method comprise the administration of a composition according to any of the composition embodiments described herein. In particular, the disorder is selected from (i) inflammatory bowel disease and (ii) graft-versus-host disease following hematopoietic stem cell transplantation. In particular, the disorder is colitis.

There is therefore provided a method for maintenance therapy of a subject who has suffered from or is suffering from a disorder selected from (i) inflammatory bowel disease and (ii) graft-versus-host disease following hematopoietic stem cell transplantation, which method comprises administered to said subject a hydroxylase inhibitor. Particular embodiments of this method comprise the administration of a composition according to any of the composition embodiments described herein.

There is therefore provided a method for maintenance therapy of a subject who has suffered from, or is suffering from, colitis which method comprises administered to said subject a hydroxylase inhibitor. Particular embodiments of this method comprise the administration of a composition according to any of the composition embodiments described herein.

Aspects and embodiments of the present invention relate to compositions comprising an immunosuppressant as an active ingredient, and more particularly water-insoluble active ingredients selected from calcineurin inhibitors, mTor inhibitors and macrolide immunosuppressants. Embodiments relate to compositions comprising a macrolide immunosuppressant as active ingredient. Exemplary macrolide immunosuppressants cyclosporins, tacrolimus, ascomycins and sirolimus, for example cyclosporin A, whose international non-proprietary name is ciclosporin. Macrolide immunosuppressants are poorly soluble in water but may be dissolved more readily in hydrophobic environments, as described herein.

The disclosure includes an invention predicated on a finding relating to minibeads which themselves form an embodiment of the invention and which comprise a matrix constituted by gelatin or another water soluble polymer and contain a macrolide immunosuppressant, a water-immiscible liquid in which the macrolide immunosuppressant is soluble and a hydrophilic surfactant having an HLB value of at least 10. It is inferred in these beads that the water-immiscible liquid forms droplets or inclusions in the matrix (and for the purposes of defining the invention this is considered to be the case), with the immunosuppressant mainly or wholly (for practical purposes) being in the water-immiscible liquid and at least a significant proportion of the hydrophilic surfactant being in the water-soluble polymer phase (outside the water-immiscible liquid). Such minibeads, in some cases further containing a hydroxylase inhibitor, and having a coating designed to achieve release of the active(s) at least in the colon, were tested in an animal model and found to protect against loss (resist loss) of intestinal barrier function. Those tests involving co-administration of the macrolide immunosuppressant and the hydroxylase inhibitor were particularly effective. See in particular Examples 1-5.

The invention therefore includes a pharmaceutical composition for oral administration, comprising a unit solid which comprises a water-soluble polymer matrix material in which matrix material are dispersed a water-insoluble active ingredient selected from calcineurin inhibitors, mTor inhibitors and macrolide immunosuppressants; droplets of water-immiscible liquid in which the water-insoluble active ingredient is soluble; and a hydrophilic surfactant having an HLB value of at least 10, the composition being adapted to release water-insoluble active ingredient in at least the colon and the water-insoluble active ingredient being for therapeutic use in combination therapy with a hydroxylase inhibitor.

The hydroxylase inhibitor may be comprised in a pharmaceutical formulation adapted to release the inhibitor in at least the colon. In particular, the unit solid containing the water-insoluble active ingredient may contain the hydroxylase inhibitor; in this case the composition may comprise a single population of beads. It is implicit, and by virtue of this sentence explicit, that the hydroxylase inhibitor is for therapeutic use.

The composition may comprise two populations of unit solids, e.g. two populations of minibeads, a first population containing the water-insoluble active ingredient and a second population containing the hydroxylase inhibitor.

Further provided is an emulsion for use in manufacturing a composition as above, the emulsion comprising oil droplets dispersed in an aqueous phase characterised in that the aqueous phase comprises a water-soluble polymer and in that the emulsion comprises a water-insoluble active ingredient selected from calcineurin inhibitors, mTor inhibitors, and macrolide immunosuppressants, a hydroxylase inhibitor and a hydrophilic surfactant having an HLB value of at least 10.

A further aspect of the invention resides in a pharmaceutical composition for oral administration, obtainable by:

A) mixing together at least the following materials to form an emulsion:

i) a water-insoluble active ingredient selected from calcineurin inhibitors, mTor inhibitors, and macrolide immunosuppressants;
ii) an aqueous phase comprising water and a water-soluble polymer material;
iii) a hydrophobic liquid;
iv) a hydrophilic surfactant having an HLB value of at least 10;
v) optionally one or more excipients which are miscible with or soluble in hydrophobic liquid to increase the solubility of the immunosuppressant in the liquid, wherein the water-insoluble active ingredient is soluble in the hydrophobic liquid when it is combined with any said one or more excipients; and B) formulating the emulsion into a pharmaceutical composition comprising a unit solid which comprises the emulsion in a dry state, wherein the composition is adapted to release the active ingredient at least into the colon and the active ingredient is for therapeutic use in combination therapy with a hydroxylase inhibitor.

The invention includes a method for administering to a subject (i) a water-insoluble active ingredient selected from calcineurin inhibitors, mTor inhibitors and macrolide immunosuppressants; and (ii) a hydroxylase inhibitor, the method comprising:

orally administering a pharmaceutical composition comprising a unit solid which comprises a water-soluble polymer matrix material in which matrix material are dispersed the water-insoluble active ingredient, droplets of water-immiscible liquid in which the water-insoluble active ingredient is soluble and a hydrophilic surfactant having an HLB value of at least 10, the composition being adapted to release the water-insoluble active ingredient in at least the colon; and simultaneous, sequentially or separately administering a hydroxylase inhibitor to the subject The invention also includes a method for treating a disorder of, or at least suspected of being associated with, a leaky intestinal epithelial barrier, the method comprising orally administering an effective amount of a pharmaceutical composition comprising a water-soluble polymer matrix material in which are dispersed a water-insoluble active ingredient selected from calcineurin inhibitors, mTor inhibitors and macrolide immunosuppressants, and droplets of water-immiscible liquid in which the active ingredient is soluble, wherein the composition is adapted to release the active ingredient in at least the colon. See in particular Examples 1-5.

Another embodiment is a product for use in manufacturing a composition as previously defined, the product being a water-soluble polymer matrix material formulated as a minibead having a diameter of no more than 10 mm, e.g. of not more than 5 mm, in which matrix material are a water-insoluble active ingredient selected from calcineurin inhibitors, mTor inhibitors and macrolide immunosuppressants; droplets of a water-immiscible liquid in which the water-insoluble active ingredient is soluble, and a hydrophilic surfactant having an HLB value of at least 10.

Further provided by the invention is a pharmaceutical composition for oral administration, comprising a water-soluble polymer matrix material in which matrix material are dispersed a water-insoluble active ingredient selected from calcineurin inhibitors, mTor inhibitors and macrolide immunosuppressants; droplets of a water-immiscible liquid in which the water-insoluble active ingredient is soluble, wherein the composition is adapted to release the water-insoluble active ingredient in at least the colon and is for use in treating a disorder of, or at least suspected of being associated with, a leaky intestinal epithelial barrier. In one embodiment the disorder is not Crohn's disease, ulcerative colitis, GVHD, or GI-GVHD. In another embodiment the disorder is Crohn's disease, ulcerative colitis, GVHD, or GI-GVHD. In one embodiment the disorder is not inflammatory bowel disease, Crohn's disease, ulcerative colitis, GVHD, or GI-GVHD. In another embodiment the disorder is inflammatory bowel disease, Crohn's disease, ulcerative colitis, GVHD, or GI-GVHD. In one embodiment the disorder is not irritable bowel syndrome, inflammatory bowel disease, Crohn's disease, ulcerative colitis, GVHD, or GI-GVHD. In another embodiment the disorder is irritable bowel syndrome, inflammatory bowel disease, Crohn's disease, ulcerative colitis, GVHD, or GI-GVHD. Also disclosed is an embodiment in which the disorder is not irritable bowel syndrome, inflammatory bowel disease, Crohn's disease, ulcerative colitis, GVHD, or GI-GVHD.

Macrolide immunosuppressants are water-insoluble and act locally in the colon to suppress inflammations, and non-macrolide (as well as macrolide) calcineurin inhibitors and mTor inhibitors have the same function and are therefore usable in place of a macrolide immunosuppressant.

For all aspects and implementations of the invention, the therapy may affect the entirety of the GIT or a portion thereof, in particular any portion thereof which includes the GIT below the small intestine. The small intestine is the primary location of absoption of drugs and, by preferentially delivering the active agent below the small intestine, a therapy may reduce absorption whilst permitting effective local activity in the GIT, such as in the colon. It is generally understood that the GIT below the small intestine comprises the large intestine which, according to the Terminologia Anatomica (TA), the international standard on human anatomic terminology, comprises the cecum, colon, rectum and anal canal. Macrolide immunosuppressants are poorly absorbed in the colon and targeted delivery to the colon as described herein is beneficial to treat disorders of the colon, rectum and/or anal canal.

Preferential delivery of the active agent to the GIT below the small intestine means that the active agent is preferentially released into the lumen of the GIT below the small intestine, and preferably into the colon. All aspects of the invention may be implemented using a formulation which comprises minibeads (sometimes called minicapsules) and optionally more than half of the minibeads, e.g. all of them, comprise a barrier to prevent release and degradation of the active agent in the stomach and small intestine. The barrier may comprise an enteric polymer product, for example an enteric coating, or it may comprise an erodible coating. The barrier may comprise a coating which comprises a polymer, e.g. a polysaccharide, which is specifically susceptible to degradation by bacterial enzymes in the colon, i.e. is susceptible to degradation by bacterial enzymes in the colon but not by enzymes higher up the GIT.

A formulation comprising an immunosuppressant, e.g. a macrolide immunosuppressant, may be for use in achieving systemic inhibition of a pro-inflammatory cytokine, for example IL-1, IL-17, IL-8, IL-22 and/or TNFα which is lower than the local inhibition in the gastrointestinal tract. The formulation may be for use in limiting systemic inhibition of a pro-inflammatory cytokine while achieving clinically effective local inhibition in the gastrointestinal tract, e.g. optimising the local inhibition in the gastrointestinal tract. See Example 5.

For all aspects and implementations of the invention, therefore, at least a portion of the active agent may be protected against degradation in the upper gastrointestinal tract, and optionally in the stomach and small intestine. The formulation may be adapted for a first portion of the active agent to be released in the upper gastrointestinal tract and a second portion of the active agent to be released in the colon. The second portion may comprise more than half said active agent in the formulation, e.g. at least 60%, at least 70% or at least 80% thereof. As mentioned above, therefore, the formulation may comprise minibeads and more than half of the minibeads, e.g. at least 60% of them, at least 70% of them, at least 80% of them or all of them, may comprise a barrier to prevent release and degradation of the active agent in the stomach and small intestine. The protection against degradation or barrier may be provided by a coating selected from enteric coatings and coatings comprising a polymer specifically susceptible to degradation by bacterial enzymes in the colon.

However, celiac disease may also manifest itself in the colon as microscopic colitis and IBD. Further, patients suffering from celiac disease suffer an increased risk of also suffering from ulcerative colitis. It will therefore often be beneficial for celiac patients to have the actives described herein delivered to the colon as well as the small intestine. The invention therefore provides combination formulations comprising hydralazine and cyclosporin A which are for use in delivery of the actives in the small intestine and for use in combination with a combination formulation comprising hydralazine and cyclosporin A for us in delivery of the actives in the colon. The two different combination formulations may be administered simultaneously, sequentially or separately. For example, a unit dosage, e.g. a capsule, may comprise a first population of hydralazine/cyclosporin minicapsules having a controlled release coating to release the active in the small intestine and a second population of hydralazine/cyclosporin minicapsules having a controlled release coating to release the actives in the colon. See below for more about coatings. The second population may constitute no more than 50% of minibeads in the unit dosage form, e.g. at least 10% or at least 20% and no more than 30% or 40%, for example from 20%-40% or 10%-30%.

The active agent, therefore, may all be comprised in minibeads. A multiplicity of such minibeads may be comprised in a unit dosage form, for example a gelatine or other capsule, a sachet or a compressed tablet. The formulation may therefore consist of a multiplicity of minibeads and optionally a capsule or other container for the minibeads. For all aspects and implementations of the invention, the formulation may comprise a first population of minibeads adapted to release the active agent in the upper gastrointestinal tract and a second population of minibeads adapted to release the active agent in the colon. The second population of minibeads may comprise more than half said active agent in the formulation, e.g. at least 60%, at least 70% or at least 80% thereof. The second population of minibeads may have a coating comprising a polymer specifically susceptible to degradation by bacterial enzymes in the colon, i.e. susceptible to degradation by bacterial enzymes in the colon but not by enzymes higher up the GIT.

The formulation may comprise multiple seamless minibeads (also known as seamless minicapsules) comprising the active agent. The minibeads referred to throughout this specification may therefore be seamless. The seamless minibeads may comprise a water soluble polymer matrix and, dispersed in the matrix, a dispersed phase composed of materials selected from hydrophobic and amphiphilic materials, and combinations thereof. The minibeads may comprise a composition having the characteristics of a dried state of colloid having a continuous aqueous phase comprising a hydrogel-forming polymer. The colloid may have a dispersed phase selected from a hydrophobic phase, a water in oil emulsion, and a micellar phase selected from micelles, promicelles and combinations thereof. The matrix, or the hydrogel-forming polymer of the dried colloid, may comprise a hydrophilic surfactant. The dispersed phase may comprise a hydrophobic surfactant. For all aspects and implementations of the invention, the matrix (the hydrogel-forming polymer) may comprise a hydrophilic surfactant having an HLB value of at least 15 and the dispersed phase may be a hydrophobic phase comprising a non-ionic surfactant having an HLB value of at least 10 but less than that of the hydrophilic surfactant.

It is believed having regard to the data included in this application that a multiple minibead formulation as described herein and wherein the minibeads comprise hydralazine, may comprise a low amount of hydroxylase to be clinically useful, In particular, the hydralazine in such a formulation may be in solid solution in the matrix phase of the minibeads, i.e. the minibeads may have the characteristics of minibeads during the process of manufacturing which the hydralazine was dissolved in an aqueous phase mix or premix to form a clear solution, and the minibeads may be obtained by such a process. The minibeads may include a dispersed phase, e.g. to include a hydrophobic active, but a dispersed phase is not necessary, and the minibeads may therefore be optionally coated single-phase (matrix-only) minibeads. This insight applies both to hydralazine for maintenance therapy and therefore optionally for use in monotherapy, and to hydralazine for combination therapy as described herein, e.g. with an immunosuppressant, to restore or improve GIT health. Any immunosuppressant may be included in the same minibeads as the hydralazine, in a second population of minibeads from the hydralazine in the same dosage form, or in a separate dosage form, e.g. in separate multiple minibead capsules. Specifically a unit dosage form, for example a multiple minibead capsule may comprise hydralazine in an amount of from 2.5 mg-100 mg, e.g. 2.5 mg-50 mg or 5 mg-100 mg, e.g. 5 mg-50 mg. The amount of hydralazine may be from 2.5 mg to 25 mg, e.g. 5 mg-25 mg, for example 5 mg-10 mg. The unit dosage form may be administered for example one, two or three times a day, e.g. may be for once a day therapy. In particular, the unit dosage forms described in this paragraph are for administration to human subjects.

One embodiment of the minibeads mentioned herein comprises a water-soluble polymer matrix in which are dispersed droplets of water-immiscible liquid, the matrix including a surfactant and the composition comprising a said active principle. In another embodiment, the minibeads comprise a water-soluble polymer matrix in which are dispersed droplets of water-immiscible liquid, the water-immiscible liquid comprising a surfactant and the composition comprising a said active principle. In a further embodiment, the minibeads comprise a water-soluble polymer matrix in which are dispersed droplets of water-immiscible liquid, the matrix including a surfactant, the water-immiscible liquid comprising a surfactant, and the composition comprising a said active principle.

The dispersed phase described herein may be an oil phase. The dispersed phase described herein may be a micellar phase.

The extent to which dissolution may affect the composition's physical form and features depends on the initial shape, size and make-up of the composition. Where the composition bears a coat, the rate and manner of dissolution can be modified (see below).

In one aspect, the minibeads can be described as comprising a dried oil-in-water (o/w) emulsion. The formulations of the invention may comprise multiple droplets of water-immiscible liquid within a moulded or shaped form e.g. a minibead. The formulations of the invention may comprise multiple droplets of surfactant within a moulded or shaped form e.g. a minibead.

The formulations of the invention may comprise a plurality of optionally coated minibeads having a water-soluble polymer matrix. In a particular embodiment, the formulation comprises a plurality of minibeads of dried oil-in-water emulsion.

In the case of formulations which comprise minibeads, at least some of the minibeads (e.g. a first population) may comprise a said active agent (optionally in combination with at least one further active ingredient) and optionally other minibeads (e.g. a second population) which comprise a said active agent (optionally in combination with at least one further active ingredient) or one population may be free of active principles or include "deactivating" principles e.g. enzyme or toxin sequesters or include active excipients, such as, for example, permeability enhancers, which may enhance, moderate or potentiate the effect of an active principle in another population. The formulations of the invention may comprise multiple populations of minibeads. The active principles may be the same or different as between populations, provided that at least one population includes an active agent as required by the invention.

The invention includes formulations in which an active agent and optionally one or more further active ingredient(s) is (are) incorporated in a dispersed phase mentioned herein. The invention includes formulations in which an active agent and optionally one or more further active ingredient(s) is (are) incorporated in a continuous phase (matrix phase) mentioned herein. Both the dispersed phase and the continuous phase may include an active ingredient, and each phase may have an active ingredient different from that in the other phase, the minibeads comprising an active agent required by the invention.

In the case of formulations comprising minibeads, the minibeads may be coated with a polymer to alter the release profile or to protect the bead and/or the active principle within the bead from degradation or oxidation or hydrolysis or proteolysis or degradation mediated by high or low pH.

In the instance of formulations comprising minibeads having a water-soluble polymer matrix and a dispersed phase comprising a hydrophobic material, an amphiphilic material or a combination thereof, the invention is of particular interest for active agents of low aqueous solubility and/or liposoluble active agents where incorporation into the dispersed phase (e.g. an oil phase) brings particular advantages.

The invention includes within its scope formulations in which a said active agent is formulated for oral administration as minibeads of dried oil-in-water emulsions in which the active agent may be incorporated in the oil phase of the emulsion, the beads being optionally coated with a polymer. The invention includes within its scope formulations in which a said active agent is formulated for oral administration as minibeads of dried aqueous micelle compositions in which the active agent may be incorporated in the micelle phase of the emulsion, the beads being optionally coated with a polymer.

The water-soluble polymer matrix (or in one aspect, the aqueous phase of a dried emulsion) comprises, in one embodiment, a cross-linked water-soluble polymer e.g. resulting from chemical or physico-chemical (e.g. drying) solidification of a fluid aqueous continuous phase such that, in the matrix or dried emulsion, water is substantially absent and the dispersed phase is immobilized. In this embodiment, the dried aqueous phase can therefore be referred to as an immobilization matrix.

The term "dried emulsion" generally means an emulsion whose internal (discontinuous) phase has been immobilized in a substantially solid or solidified external phase. The solid external phase dissolves on contact with an aqueous medium. The term "dried aqueous micelle composition" generally means an aqueous micelle composition whose micelle phase has been immobilized in a substantially solid or solidified external phase. The solid external phase dissolves on contact with an aqueous medium.

The term "matrix" is a term well-known in the art and generally means, according to context, a solid, semi-solid, undissolved or not-yet-dissolved material which provides structure and volume to a composition.

Solidification of the external phase may have arisen through various means including chemically (e.g. by cross-linking) or physically (e.g. by cooling or heating). By use of the term "dried", it is not sought to imply that a drying step is necessary to produce the dried emulsion or micelle composition (although this is not excluded) rather that the solid or solidified aqueous external phase is substantially free of water or free of available water. In this respect, the term "aqueous phase" is nevertheless employed in this document to denote the external (continuous) phase of the composition of the invention even though water, in certain embodiments, is largely absent from (or trapped within the cross-linked matrix of) the minibead compositions. The external phase of the minibead composition is however water-soluble and dissolves in aqueous media. In one embodiment, the oil droplets or micelles are released when the aqueous phase dissolves or is exposed to aqueous media.

The term "released" in relation to the oil droplets or micelles means free to move, egress, coalesce, dissolve, (re)emulsify etc. although actual movement, egression, coalescence, association or (re)emulsification is not a requirement i.e. may not occur and indeed may intentionally be constrained e.g. by presence of a coat or coating and/or by incorporation of certain constraining or retarding substances into the water-soluble polymer matrix.

The inclusion in the aqueous phase of a surfactant (described below) may lead to improved dissolution or release of the active agent. In particular, it has been found that, when the formulation comprises minibeads bearing a polymeric coating, inclusion of a surfactant in the aqueous phase enhances dispersion/egress through pores or other openings in the polymer coat (or other local removal, swelling or weakening of the polymer coat). Where the minibeads have an oil phase which comprises a surfactant, the surfactant included in the aqueous phase may be different from any surfactant included in the oil phase.

In embodiments, the formulations comprise minibeads which comprise a matrix constituted by gelatin or another water soluble polymer (or a combination thereof) and contain a water-insoluble active agent, a water-immiscible liquid in which the active agent is soluble and a hydrophilic surfactant having an HLB value of at least 10. It is inferred in these minibeads that the water-immiscible liquid forms droplets or inclusions in the matrix (and for the purposes of defining the invention this is considered to be the case), with the active agent mainly or wholly (for practical purposes) being in the water-immiscible liquid and at least a significant proportion of the hydrophilic surfactant being in the water-soluble polymer phase (outside the water-immiscible liquid).

Some formulations of the invention are obtainable by a process comprising:

B) mixing together at least the following materials to form an emulsion:
  i) a said active agent;
  ii) an aqueous phase comprising water and a water-soluble polymer material;
  iii) a hydrophobic liquid;
  iv) a hydrophilic surfactant having an HLB value of at least 10;
  v) optionally one or more excipients which are miscible with or soluble in hydrophobic liquid to increase the solubility of the immunosuppressant in the liquid,
wherein the water-insoluble active ingredient is soluble in the hydrophobic liquid when it is combined with any said one or more excipients; and C) formulating the emulsion into a pharmaceutical composition comprising a minibead which comprises the emulsion in a dry state, wherein the composition is adapted to release the active ingredient at least into the colon.

For all embodiments and aspects of the invention, the minibead may optionally have the characteristics of a product prepared by a method comprising:

A) mixing together at least the following materials to form an emulsion:
  i) the active agent(s);
  ii) an aqueous phase comprising water and a water-soluble polymer material;
  iii) a hydrophobic liquid;
  iv) a hydrophilic surfactant having an HLB value of at least 10;
  v) optionally one or more excipients which are miscible with or soluble in hydrophobic liquid to increase the solubility of the immunosuppressant in the liquid,
wherein the water-insoluble active ingredient is soluble in the hydrophobic liquid when it is combined with any said one or more excipients; and B) formulating the emulsion into a unit solid which comprises the emulsion in a dry state.

In particular the mixing together may optionally comprise forming a clear solution of hydrophobic (water-insoluble) active agent(s) in the hydrophobic liquid together with any said one or more excipients. For all aspects and implementations of the disclosure, there may be formed a premix of the continuous phase and a premix formed of the disperse phase, each complete premix optionally being a clear solution before the two premixes are combined to form a liquid colloidal composition, e.g. emulsion or aqueous micelle composition.

More particularly, the manufacture of a minibead may optionally comprise:
  i) forming an aqueous phase premix comprising, or usually consisting of, a solution in water of water-soluble constituents including a water-soluble thermotropic hydrogel-forming polymer, any water-soluble excipient(s), any water-soluble active(s);
  ii) forming a water-immiscible phase premix (sometimes called an oil phase premix) comprising, or usually consisting of, a solution in water-immiscible liquid of water-insoluble constituents (e.g. water-insoluble active(s));
  iii) mixing the two phases form an emulsion, and iv) formulating the emulsion into a minibead, e.g. ejecting it through a single orifice nozzle to form droplets which are caused or allowed to fall into a water-immiscible cooling liquid in which the droplets cool to form minibeads, and then separating the minibeads from the cooling liquid.

In embodiments, therefore, the one or more active pharmaceutical ingredients are dissolved during manufacture. It is inferred therefore in such embodiments that, in the final minibead, the water-insoluble active ingredient is in solution in the water immiscible liquid. Similarly, if a water-soluble active ingredient is used, it will in the embodiments mentioned in this paragraph be dissolved in the aqueous phase and it is inferred that the water soluble active ingredient may in this case be considered in the minibead to be in solid solution in the polymer (i.e. outside the dispersed phase).

The invention includes embodiments in which water and water-soluble constituents are formed into a clear solution which is mixed with the dispersed phase medium (e.g. a water immiscible liquid). The invention includes embodiments in which a water-immiscible liquid and water-insoluble constituents are formed into a clear solution which is mixed with the aqueous phase. Both phases may be clear solutions prior to mixing of them to form an emulsion.

The reader will understand that the manufacture may use water and a water-immiscible liquid, e.g. a liquid lipid, or water and a micelle-former (surfactant). During manufacture, the constituents will partition between the water phase and the non-aqueous phase, or their interface, according to their solubilities in each phase. The water-insoluble constituents will overwhelmingly be present in the water-immiscible part (water immiscible liquid or micelle interior) and water-soluble but lipid-insoluble constituents will overwhelmingly be present in the water phase. Absolute exclusion of a constituent from one phase down to the molecular level may not occur. Some constituents, e.g. surfactants, may be significantly soluble in both phases and may be significantly present in both phases, though they may predominantly be in one of the two phases. Thus, where it is stated that a hydrophilic surfactant is in the aqueous phase, it may be expected that a small portion of the surfactant may perhaps be found in the non-aqueous phase. The same applies mutatis mutandis to hydrophobic surfactants.

It is inferred that when the liquid emulsion has been converted to a solid, e.g. a minibead, the various constituents will remain partitioned between the non-aqueous phase and the dried aqueous phase (i.e. the water-soluble polymer matrix) substantially in the same manner as in the emulsion. This has not been demonstrated, however.

The compositions of the invention may be for use in treating a disorder of, or at least suspected of being associated with, a leaky intestinal epithelial barrier.

This paragraph applies to all aspects and implementations of the disclosure. In one embodiment the disorder is not Crohn's disease, ulcerative colitis, GVHD, or GI-GVHD. In another embodiment the disorder is Crohn's disease, ulcerative colitis, GVHD, or GI-GVHD. In one embodiment the disorder is not inflammatory bowel disease, Crohn's disease, ulcerative colitis, GVHD, or GI-GVHD. In another embodiment the disorder is inflammatory bowel disease, Crohn's disease, ulcerative colitis, GVHD, or GI-GVHD. In one embodiment the disorder is not irritable bowel syndrome, inflammatory bowel disease, Crohn's disease, ulcerative colitis, GVHD, or GI-GVHD. In another embodiment the disorder is irritable bowel syndrome, inflammatory bowel disease, Crohn's disease, ulcerative colitis, GVHD, or GI-GVHD.

A judicious combination of different types of polymeric coating (described in more detail below) can produce advantages in relation to the in vitro dissolution and in vivo performance of the composition of the invention. In particular, inclusion of a polymer which degrades in the presence of bacterial enzymes present in the colon (and/or a polymer which encourages the formation of pores in the coating—a "pore-former") with a pH-independent polymer leads to release of active principle substantially in the colon or other pre-determined site of the GI tract. In a particular embodiment, the above mentioned polymer degradable by bacterial enzymes is water-soluble.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. Accordingly every disclosure herein is applicable to every aspect and implementation of the invention, unless mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

BRIEF DESCRIPTION OF THE DRAWINGS

Embodiments of the invention are further described hereinafter with reference to the accompanying drawings, in which:

FIG. 11 shows that there were differences between groups in the mean number of adenocarcinomas detected in the colon, with CyA (ip) and SmPill (Cya) groups having relatively fewer.

In FIG. 29 both hydralazine HCl forms result to give a similar activation level of NFκB with a tendency for stronger activation by the unformulated form, demonstrating the stability of the formulated drug. The general trend shows a maximal activation at 10 µg/mL and lower signals by increasing the concentration of the drug. An explanation is that the concentration of drug higher than 100 µg/mL could kill the cells. The activation range of NFκB seems to be between 0 and 10 µg/mL of drug. At all concentrations the excipients do not have any effect on the cells survival.

In FIG. 30 no significant activation of NFκB related to the drug is shown. Both forms result to give a similar activation level of NFκB, demonstrating again the stability of the formulated drug.

In FIG. 31 both drugs are administered together at the same concentrations. The greater influence of hydralazine HCl on the NFκB activation is clearly recognizable. To note is that the signal of formulated drug is greater than those of unformulated drug (except for 10 μg/mL and 25 μg/mL). This could indicate a better stability of the combined drugs in the formulated form, thanks the delivery in different phases. In the formulation Cyclosporin A is dissolved in the oil phase and cannot interact with hydralazine, dissolved in the water phase. The interaction of the two drugs is instead possible in the unformulated form. The concentration values in FIG. 31 express that of hydralazine (in the combination formulation).

DETAILED DESCRIPTION

Figure 1:
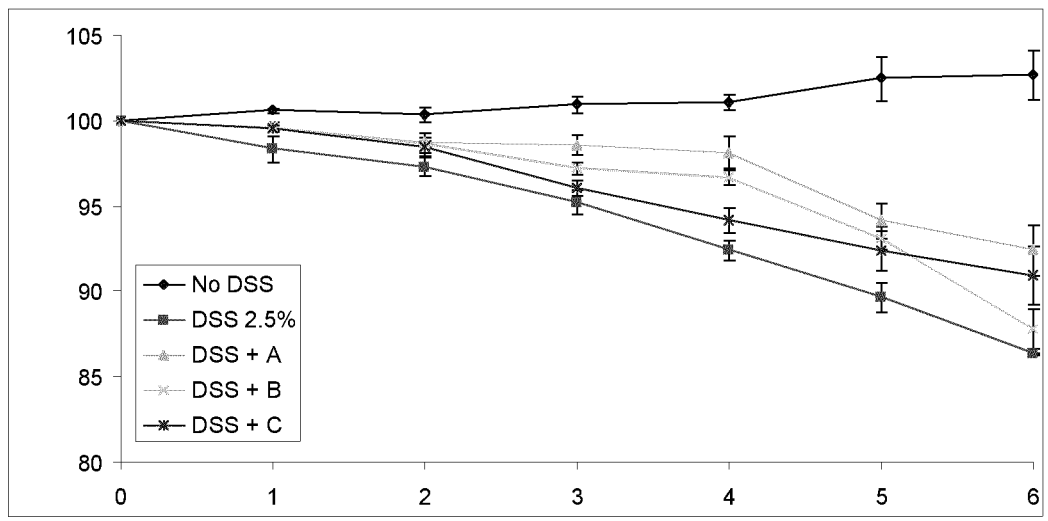
FIG. 1 is a plot of weight loss change showing the effect of compositions of the invention (see Example 2)

The present methods and compositions are as previously described useful for treatment of disorders of the GI tract which involve or result at least in part from inflammatory conditions, the treatments including by way of example maintenance therapy or prophylaxis as well as treatment to improve the condition of a patient. The methods and compositions are useful for treating such GI tract conditions whilst limiting absorption of the active(s) and thus limiting also unwanted system activity of the active(s). As mentioned in more detail elsewhere, methods and compositions of the invention may relate to fibrotic disorders of the GI tract; the aspects and implementations of the invention applicable to fibrotic disorders are therefore equally applicable to gastrointestinal fibrosis.

The invention will now be described in detail by reference to the various components which the composition of the invention may comprise. The term "excipient" may be used occasionally to describe all or some of the components other than the active principle(s) bearing in mind that some excipients can be active and that some active principles can have excipient character.

If not otherwise stated, ingredients, components, excipients etc of the composition of the invention are suitable for one or more of the intended purposes discussed elsewhere herein.

For the avoidance of doubt, it is hereby stated that the information disclosed earlier in this specification under the heading "Background" is relevant to the invention and is to be read as part of the disclosure of the invention.

The treatments provided by this invention may include any one or more of maintaining the health of the GIT (gastrointestinal tract), restoring or improving the health of the GIT and delaying the progression of a disorder of the GIT. In particular, the invention concerns inflammatory health of the GIT and the treatment of inflammatory disorders of the GIT. The term "treatment", and the therapies encompassed by this invention, include the following and combinations thereof: (1) inhibiting, e.g. delaying initiation and/or progression of a disorder or condition; (2) preventing or delaying the appearance of clinical symptoms of a state, disorder or condition developing in an animal (e.g. human) that may be afflicted with or predisposed to the state, disorder or condition but does not yet experience or display clinical or subclinical symptoms of the state, disorder or condition; (3) inhibiting the state, disorder or condition (e.g., arresting, reducing or delaying the development of the disease, or a relapse thereof in case of maintenance treatment, of at least one clinical or subclinical symptom thereof); and/or (4) relieving the condition (i.e., causing regression of the state, disorder or condition or at least one of its clinical or subclinical symptoms). The benefit to a patient to be treated may be either statistically significant or at least perceptible to the patient or to the physician. It will be understood that a medicament will not necessarily produce a clinical effect in every patient to whom it is administered, and this paragraph is to be understood accordingly. The compositions and methods described herein are of use for therapy and/or prophylaxis of the mentioned conditions.

The treatments may include maintenance therapy of patients who have suffered a GI tract disorder and whose condition has subsequently improved, e.g. because of treatment. Such patients may or may not suffer a symptomatic GIT disorder. Maintenance therapy aims to arrest, reduce or delay (re-)occurrence or progression of a GIT disorder.

The invention primarily concerns the treatment of humans but other warm-blooded animals, e.g. mammals are also embraced by the invention, for example agricultural mammals and domesticated mammals. Examples are pigs, dogs and cats. For example, the compositions and methods of the invention may be applied to porcine proliferative enteropathy.

In some embodiments, the subject is suffering from Crohn's disease. In other embodiments, the subject is suffering from ulcerative colitis. In still further embodiments, the subject is suffering from irritable bowel syndrome (e.g. with constipation, diarrhea and/or pain symptoms), celiac disease, stomach ulcers, diverticulitis, pouchitis, proctitis, mucositis, radiation-associated enteritis, short bowel disease, or chronic diarrhea. The administration of a composition of the disclosure may reduce the symptoms of disease (e.g. reduces the symptoms of inflammatory bowel disease, Crohn's disease, ulcerative colitis, irritable bowel syndrome, celiac disease, stomach ulcers, diverticulitis, pouchitis, proctitis, or chronic diarrhea). The subject may be suffering from GVHD. As used herein, "GVHD" in particular means GI-GVHD (gastrointestinal graft-versus-host disease). Further examples of inflammatory disorders to which the invention may be applied are: diversion colitis, ischemic colitis, infectious colitis, chemical colitis, microscopic colitis (including collagenous colitis and lymphocytic colitis), atypical colitis, pseudomembraneous colitis, fulminant colitis, autistic enterocolitis, interdeminate colitis, Behcet's disease, jejunoiletis, ileitis, ileocolitis and granulomatous colitis. The invention in its aspects and implementations is applicable to the disorders mentioned in this paragraph, therefore.

The products, methods and uses of the invention may be applied to enteropathies, for example gluten-sensitive enteropathy, hemorrhagic enteropathy, protein-losing enteropathy, radiation enteropathy, HIV-enteropathy, enteropathy associated with T-cell lymphoma, autoimmune enteropathy or porcine proliferative enteropathy. Colorectal carcinoma and adenocarcinoma are inflammation-related diseases. The treatments and products described herein are useful for patients who have suffered from, do suffer from or have risk factors for, such cancers. The disclosed therapies and products may be used in (e.g. as part of) the treatment of such carcinomas or in maintenance therapies of patients who have suffered from such carcinomas. The invention in its aspects and implementations is applicable to the disorders mentioned in this paragraph.

Solubilities of compounds, e.g. actives, in a solvent (for example water) may be defined as follows, the solubility being measured at 25° C. and parts being by weight:

| Descriptive Team | Parts of Solvent for 1 part of solute |
| --- | --- |
| Very Soluble | Less than 1 |
| Freely Soluble | From 1 to 10 |
| Soluble | From 10 to 30 |
| Sparingly Soluble | From 30 to 100 |

| Descriptive Team | Parts of Solvent for 1 part of solute |
| --- | --- |
| Slightly Soluble | From 100 to 1000 |
| Very Slightly Soluble | From 1000 to 10,000 |
| Practically Insoluble | More than 10,000 |

Typically, but not necessarily, the invention provides that active agents which are practically insoluble, very slightly soluble or sparingly soluble in water are in the form of a liquid, semi-solid or solid solution in a hydrophobic or amphiphilic environment, e.g. medium.

Actives which are not particularly water soluble, e.g. are practically insoluble, very slightly soluble or slightly soluble, perhaps even are sparingly soluble, may be more soluble in a suitable dispersed phase of a minibead than in the aqueous phase, and may therefore advantageously be incorporated in the dispersed phase.

The invention provides amongst other things oral pharmaceutical formulations for use in a therapy as mentioned herein. The formulations comprise an active agent as specified previously. The formulations may be multiple minibead formulations, i.e. comprise a multiplicity of minibeads, for example at least 25 minibeads, e.g. at least 50 minibeads.

In particular embodiments, the formulations comprise minibeads and the minibeads comprise or consist of minibeads in which the content of said active agent(s) is in dissolved form, i.e. is in solution.

The formulations may comprise a water-soluble polymeric matrix in which said active agent(s) is or are dispersed, the matrix in particular forming minibeads which may additionally comprise one or more coatings. The polymer material constituting the matrix may be, or may comprise, a hydrogel-forming polymer. The polymer part of the matrix may therefore consist of a hydrogel-forming polymer. The formulations may comprise minibeads formed of a polymeric matrix phase and a dispersed phase, although a dispersed phase may optionally be dispensed with, in particular where the active agent(s) is/are water soluble such that they can be dissolved in the matrix phase. Alternatively, water soluble actives may be dispersed in the polymeric matrix in particulate form, e.g. as micro- or nano-particles. The term "water soluble" in this paragraph and elsewhere in the specification includes reference to substances which are categorised as soluble, freely soluble and very soluble. It may include reference to substances where are sparingly soluble.

The matrix may include in addition to the water-soluble polymer and any dissolved active(s), other ingredients such as, for example, excipients which may, for example, modulate the behaviour of the matrix phase and/or of other constituents during manufacture and/or after administration.

The matrix advantageously comprises a hydrophilic surfactant having an HLB value of at least 10 and particularly of at least 15.

In embodiments, the active agent does not consist of a single one of, or consist of a combination consisting of, cyclosporin, tacrolimus, sirolimus, azathioprine, 6-mercaptopurine, methotrexate, soluble TNF receptor, antibodies raised to TNF, zinc, glucocorticosteriods, interferons, opioids, infliximab, etanercept, adalimumab, cucumin, catechins, mycophenolate mofetil, an NO donor, a steroid (e.g. is not budesonide or another corticosteroid and is not an adrenal steroid, e.g. is not prednisone or a hydrocortisone, administered alone or in combination with a xanthine or methylxanthine compound); a cytokine e.g. is not sulfasalizine (salicyl-azo-sulfapyridine, or "SASP") or a 5-aminosalicylic acid product. The invention also comprises products methods and uses which comprise at least one active mentioned in this paragraph.

The formulations may comprise gelatin as the water-soluble polymer. The gelatin may be substantially the only water-soluble polymer.

The water-soluble matrix material may be selected from a hydrocolloid, a non-hydrocolloid gum and chitosan and derivatives thereof.

The formulations may comprise a unit solid which may be a minibead having a diameter of not more than 10 mm, e.g. of not more than 5 mm, the composition optionally comprising a plurality of said minibeads. The minibead may be monolithic, optionally with layers thereon. The one or more minibeads may comprise a controlled-release polymer, e.g. incorporated in the matrix and/or coated on it. The minibeads may comprise plural controlled release polymers, which may be present as a mixture or be separated, e.g. a first controlled-release polymer may be comprised in a coat and a second (different) controlled-release polymer may be comprised in the matrix. The or each polymer may be associated with one or more excipients, e.g. a pore former. The or each controlled-release polymer may be an extended release polymer or an enteric polymer. The minibead(s) may have a coat which comprises the controlled release polymer and optionally a polymer susceptible of degradation by bacterial enzymes.

In embodiments, the or each minibead comprises a controlled-release polymer which is ethylcellulose comprised in a coating on the minibead and optionally in association with an emulsification agent, for example ammonium oleate. The ethylcellulose may also be in association with a plasticizer, e.g. dibutyl sebacate or medium chain triglycerides. The coating may further comprise polymer susceptible of degradation by bacterial enzymes. The polymer susceptible of degradation by bacterial enzymes may be water-soluble, preferably pectin.

The hydrophilic surfactant may have an HLB value of at least 15, and optionally of at least 18, e.g. of at least 20 or at least 25.

The hydrophilic surfactant may be an anionic surfactant. The anionic surfactant may have an HLB value of at least 30, e.g. at least 35, for example of 40±2. The anionic surfactant may comprise or be an alkyl sulfate salt. The alkyl sulfate salt may be sodium dodecyl sulfate (SDS). The water-soluble polymer matrix material may further contain a non-ionic surfactant having an HLB value of at least 10 but less than that of the hydrophilic surfactant. The non-ionic surfactant may comprise a poly(oxyethylene) group, e.g. comprise a glycerol polyethylene glycol ricinoleate (as in the case of Cremophor EL).

In embodiments, the hydrophilic surfactant is selected from cationic and non-ionic surfactants, and combinations thereof.

The dispersed phase may be composed of, or predominantly of, hydrophobic and/or amphiphilic materials in which hydrophobic active(s) may be dissolved. Generally, the dispersed phase may provide a hydrophobic environment either in a hydrophobic material or within the hydrophobic part of a micelle or promicelle. The dispersed phase may comprise a water-immiscible liquid. The water-immiscible liquid may comprise a liquid lipid and optionally a solvent miscible therewith, in which solvent the water-insoluble active ingredient is soluble. The ratio of liquid lipid to non-ionic surfactant may be in the range 1-4:1 by weight, optionally 1.2-3.0:1 by weight. The liquid lipid may be a medium chain triglyceride (MCT) composition, the medium chain triglyceride(s) being one or more triglycerides of at least one fatty acid selected from $C_6$-$C_{12}$ fatty acids. It will be understood that commercially available MCT compositions useful in the invention are mixtures derived from natural products and usually or always contain minor amounts of compounds which are not MCTs; the term "medium chain triglyceride composition" is therefore to be interpreted to include such compositions.

The liquid lipid may be a caprylic/capric triglyceride, i.e. a caprylic/capric triglyceride composition (which it will be understood may contain minor amounts of compounds which are not caprylic/capric triglycerides).

For all embodiments of the invention, a water-insoluble active ingredient may have a solubility in the water-immiscible liquid of at least 5 mg/ml, and often of at least 10 mg/ml, e.g. at least 25 mg/ml, for example at least 50 mg/ml.

Said solvent which is optionally included in a water-immiscible liquid may be miscible with both the liquid lipid and with water, e.g. it may be 2-(2-ethoxy)ethanol.

The dispersed phase, e.g. water-immiscible phase (water-immiscible droplets), may represent from 10-85% by dry weight of the composition.

The unit solid or minibead may have a low water content.

In an embodiment the pharmaceutical formulation is a capsule comprising a population of minibeads which have a diameter of at most 10 mm and which comprise a surfactant-containing water-soluble polymer matrix material and a coating on the matrix material, wherein the hydrophilic surfactant has an HLB value of at least 15, and wherein the coating comprises a controlled-release polymer, optionally wherein the coating is a barrier membrane for extended release of the active agent(s) and/or is a coating which resists becoming degraded or becoming of increased permeability in the conditions of the GI tract above the colon but which becomes degraded or of increased permeability in the conditions of the colon. The minibeads may further comprise in the polymer matrix part a non-ionic surfactant comprising a poly(oxyethylene) group and the hydrophilic surfactant may be an anionic surfactant.

For all embodiments of the invention, the composition may further comprise another active pharmaceutical ingredient, in addition to said active agent(s).

The composition may comprise a gelatin or other capsule containing a plurality of minibeads into which the water-soluble polymer matrix material is formed.

Included in the invention is an intermediate product for use in manufacturing a composition of the disclosure, the intermediate product being a water-soluble polymer matrix material formulated as a minibead having a diameter of no more than 10 mm, e.g. of not more than 5 mm, in which matrix material an active agent is present in solution in the matrix itself or in a dispersed phase contained by the matrix.

Also disclosed is a method of making dried emulsion formulations of the disclosure, which method comprises mixing an oil phase with an aqueous phase comprising a water soluble polymer matrix material to form an emulsion and then causing the emulsion to solidify. The emulsion may be formed into droplets which are then exposed to a solidification medium (e.g. a water immiscible oil). In the case of a dried micelle composition, the oil phase is replaced by a surfactant phase.

The invention includes a colloidal composition, e.g. an emulsion or aqueous micelle composition, useful in making the formulations of the invention and comprising a said active agent in solution in a phase of the colloid.

Further provided is an emulsion for use in manufacturing an intermediate product of the disclosure, the emulsion comprising oil droplets dispersed in an aqueous phase characterised in that the aqueous phase comprises a water-soluble polymer matrix material and in that the emulsion comprises a said active agent in solution. In the case of a micelle composition, the oil droplets are replaced by micelles.

The invention further includes a pharmaceutical composition for oral administration, obtainable by:

(A) mixing together at least the following materials to form a colloid:
  v) a said active agent, which may be soluble or insoluble in water;
  vi) an aqueous phase comprising water and a water-soluble polymer material;
  vii) a hydrophobic liquid or a micelle-forming surfactant;
  viii) optionally a hydrophilic surfactant having an HLB value of at least 10;
  ix) optionally one or more excipients which are miscible with or soluble in hydrophobic liquid or micelle-forming surfactant to increase the solubility of the immunosuppressant in said liquid or surfactant,
wherein any water-insoluble active ingredient is soluble in the hydrophobic liquid or micelle-forming surfactant when combined with any said one or more excipients; and (B) formulating the colloid into a pharmaceutical composition comprising a unit solid which comprises the colloid in a dry state. The composition may be adapted to release the active ingredient at least into the colon.

The mixing together may comprise forming a clear solution of the active ingredient in the hydrophobic liquid or micelle-forming surfactant together with any said one or more excipients.

The formulating may comprise ejecting the emulsion through a single-orifice nozzle, e.g. having a diameter of from 0.5-5 mm, to form drops which are then caused or allowed to fall into a cooling oil or other hardening medium and allowed to harden to form minibeads, after which the minibeads are recovered from the cooling oil and dried.

All optional features previously described in relation to the invention are applicable to the below described methods and all other aspects and embodiments of the invention. Likewise, optional features described in relation to the below described methods are applicable to embodiments and aspects of the invention described earlier and late in this specification.

Surfactants

In the description and claims of this specification, the term "surfactant" is employed as a contraction for "surface active agent". For the purposes of this description and claims, it is assumed that there are four major classifications of surfactants: anionic, cationic, non-ionic, and amphoteric (zwitterionic). The non-ionic surfactant remains whole, has no charge in aqueous solutions, and does not dissociate into positive and negative ions. Anionic surfactants are water-soluble, have a negative charge and dissociate into positive and negative ions when placed in water. The negative charge lowers the surface tension of water and acts as the surface-active agent. Cationic surfactants have a positive charge, and also dissociate into positive and negative ions when placed in water. In this case, the positive ions lower the surface tension of the water and act as the surfactant. The amphoteric (zwitterionic) surfactant assumes a positive charge in acidic solutions and performs as a cationic surfactant, or it assumes a negative charge in an alkaline solution and acts as an anionic surfactant.

Surfactants can also be classified according to their hydrophilic-lipophilic balance (HLB) which is a measure of the degree to which the surfactant is hydrophilic or lipophilic, determined by calculating values for the different regions of the molecule, as described (originally for non-ionic surfactants) by Griffin in 1949 and 1954 and later by Davies. The methods apply a formula to the molecular weight of the whole molecule and of the hydrophilic and lipophilic portions to give an arbitrary (semi-empirical) scale up to 40 although the usual range is between 0 and 20. An HLB value of 0 corresponds to a completely hydrophobic molecule, and a value of 20 would correspond to a molecule made up completely of hydrophilic components. The HLB value can be used to predict the surfactant properties of a molecule:

| HLB Value | Expected properties |
| --- | --- |
| 0 to 3 | antifoaming agent |
| from 4 to 6 | W/O emulsifier |
| from 7 to 9 | wetting agent |
| from 8 to 18 | an O/W emulsifier |
| from 13 to 15 | typical of detergents |
| 10 to 18 | solubiliser or hydrotrope |

Although HLB numbers are assigned to surfactants other than the non-ionic, for which the system was invented, HLB numbers for anionic, cationic, non-ionic, and amphoteric (zwitterionic) surfactants can have less significance and often represent a relative or comparative number and not the result of a mathematical calculation. This is why it is possible to have surfactants above the "maximum" of 20. HLB numbers can however be useful to describe the HLB requirement of a desired application for a given emulsion system in order to achieve good performance.

Hydrophilic Surfactants for the Aqueous Phase

In embodiments of the invention, the unit solid comprises a hydrophilic surfactant which, without being bound by theory, is believed at least partially to partition the aqueous phase (polymer matrix).

Surfactants for such inclusion in the aqueous phase of the inventive composition are preferably readily diffusing or diffusible surfactants to facilitate manufacturing and processing of the composition of the invention. The surfactant may have an HLB of at least 10 and optionally of at least 15, e.g. at least 30 and optionally of 38-42, e.g. 40. Such surfactants can be of any particular type (cationic, anionic, non-ionic, zwitterionic) and may comprise as a proportion of dry weight of the composition from 0.1% to 6%, e.g. 0.1% to 5%. 0.1% to 4% or 0.1% to 3%, e.g. in a proportion of at least 1% and in particular between 1.0 and 4.5 or 5%, for example within or just outside the 2-4% range, for example from 2 to 3% or approximately 2% or approximately 4%. The invention includes formulations in which the hydrophilic surfactant is, or comprises, an anionic surfactant, e.g. a single anionic surfactant or a mixture thereof.

Unless otherwise stated or required, all percentages and ratios are by weight.

Preferred anionic surfactants for inclusion in the aqueous phase include perfluoro-octanoate (PFOA or PFO), perfluoro-octanesulfonate (PFOS), sodium dodecyl sulfate (SDS), ammonium lauryl sulfate, and other alkyl sulfate salts, sodium laureth sulfate, also known as sodium lauryl ether sulfate (SLES) and alkyl benzene sulfonate. A particular class of surfactant comprises sulfate salts. A preferred anionic surfactant in the aqueous phase is SDS. Mixtures of anionic surfactants are also contemplated.

The physical form of the surfactant at the point of introduction into the aqueous phase during preparation plays a role in the ease of manufacture of the composition according to the invention. As such, although liquid surfactants can be employed, it is preferred to utilize a surfactant which is in solid form (e.g. crystalline, granules or powder) at room temperature, particularly when the aqueous phase comprises gelatin.

Possible non-ionic surfactants for the aqueous phase include perfluorocarbons, polyoxyethyleneglycol dodecyl ether (e.g. Brij such as, for example, Brij 35), Myrj (e.g. Myrj 49, 52 or 59), Tween 20 or 80 (also known as Polysorbate). Brij, Myrj and Tween products are available commercially from Croda.

In general, mixtures of surfactants can be utilised e.g. to achieve optimum long term stability of the composition of the invention with shorter chain surfactants in general facilitating shorter term stability (an aid to processing) and longer chain surfactants facilitating longer term stability (an aid to shelf life). In some embodiments, shorter chain surfactants have up to $C_{10}$ alkyl (e.g. $C_6$-$C_{10}$ alkyl) as the hydrophobic portion of the surfactant whilst longer chain surfactants have $C_{10}$ or higher alkyl (e.g. $C_{10}$-$C_{22}$ alkyl) as the hydrophobic portion of the surfactant. It is envisaged that $C_{10}$ alkyl surfactants may facilitate processing or facilitate prolongation of shelf life, or both, depending on the identity of the other excipients and of the active principle(s). Higher alkyl may in particular implementations of the invention be $C_{11}$-$C_{22}$ or $C_{12}$-$C_{22}$ alkyl, and in some embodiments has a length of no greater than $C_{18}$.

Instead of (or as complement to) the surfactant in the aqueous phase, the invention also contemplates use of surfactant-like emulsifiers (also known as crystallisation inhibitors) such as, for example, HPMC (also known as hypromellose) although their use is generally contemplated in relatively smaller amounts to avoid high viscosity which may constrain processing options.

Other non-ionic surfactants which may be included in the aqueous phase include poloxamers which are non-ionic triblock copolymers composed of a central hydrophobic chain of polyoxypropylene (poly(propylene oxide)) flanked by two hydrophilic chains of polyoxyethylene (poly(ethylene oxide)). Poloxamers are available commercially under the trade name Pluronics™ Such surfactants or similar larger polymeric surfactants are aqueously soluble and are therefore presented here as optional components of the aqueous phase. However, they may be used to reduce the amount of or to replace a higher HLB polymeric component of the oil phase (see also separate section) such as, for example, polyethoxylated castor oils (polyethylene glycol ethers) exemplified commercially as Cremophor™. Diblock, tetrablock, multiblock, etc copolymers (poloxomers) are also included.

Another type of polymeric aqueous soluble surfactant which may be used in a similar way are anionic copolymers based on methacrylic acid and methyl methacrylate in which the ratio of the free carboxyl groups to ester groups is approx. 1:1 and with average molecular weight is approx. 135,000. Such a polymeric surfactant is available from Degussa under the trade name EUDRAGIT® L 100.

The surfactant included in the aqueous phase is preferably present within ranges noted above. In the minibead embodiment, avoidance of excess surfactant is desirable to avoid the "golf ball effect" whereby minibeads when dried have a plurality of point-sized dimples in their surface (visible under the microscope). While not necessarily a major concern, such dimples can lead to variability in coating if it is desired to apply for example a polymer coat to the minibeads. Although higher values within the preferred range generally increase the rate of egress/dissolution of minibeads, the present inventors/applicants have found that in certain circumstances higher levels of surfactant included in the composition of the invention can cause a counterintuitive drop in the in vitro dissolution profile including a drop in the total amount dissolved of the composition according to the invention. The concentration of surfactant above which the dissolution profile dropped (or total amount of dissolved composition dropped) was approximately 5% by dry weight of the composition for example when SDS is selected as the surfactant. In certain embodiments, it is therefore preferred to have in the aqueous phase a surfactant, whether non-ionic or ionic, for example anionic e.g. SDS, in an amount of less than 5% by dry weight of the total composition (for example, the composition may be in the form of beads or minibeads, wherein the aqueous phase contains SDS or another surfactant in an amount of less than 5% by dry weight of the beads/minibeads). In embodiments of the invention, the composition, e.g. in the form of beads or minibeads, comprises in the aqueous phase surfactant in an amount of no more than 5%, no more than 4.5%, no more than 4% or no more than 3% by dry weight of the beads or minibeads. In one class of embodiments, the surfactant is in an amount of at least 0.1% by dry weight of the beads or minibeads. In another class of embodiments, the surfactant is in an amount of at least 1% by dry weight of the beads or minibeads. In a further class of embodiments, the surfactant is in an amount of at least 2% by dry weight of the beads or minibeads. Higher levels of surfactant in the aqueous phase (e.g. above 5% by weight of the total composition) restrict the processing parameters for manufacturing when certain manufacturing approaches are followed.

It is noteworthy that surfactants are used in dissolution testing media when complete dissolution of the composition being studied is otherwise not achievable. In respect of the amount of surfactant included in the aqueous phase of the composition of the present invention as described above, the inventors/applications have surprisingly found that such (small) quantities included in the composition have a much greater effect than larger quantities included in the dissolution medium.

In the case of the minibead embodiment, the present inventors hypothesise that the local concentration of surfactant in and around the minibead as it dissolves or disperses is more effective than an otherwise greater concentration in the medium as a whole. It is also believed, although the inventors/applicants do not necessarily intend to be bound by this or other hypotheses advanced in this text, that the surfactant in the beads assists egress of active agent from within the polymer coat (if a coat is afterwards added to the minibeads) and also possibly to shield the active agent from crystallisation and/or precipitation after release from the bead.

In certain embodiments complete or substantially complete dissolution of active agent in USP/EP/JP etc dissolution apparatus using standard media can be achieved, using no or only minor amounts of surfactant in the dissolution medium, by incorporating in to the formulation of the invention (e.g. dosage form) one or more surfactants even when the quantity of surfactant incorporated into the formulation is much smaller than would have been required in the medium to achieve a comparable degree of dissolution of a formulation containing no surfactant. The one or more surfactants may be comprised in the aqueous phase (the polymer matrix) or the oil phase, or both, and are in particular comprised in at least the aqueous phase and optionally also in the oil phase.

These observations are particularly relevant to the class of minibead embodiments of the invention, in particular where an oil-soluble active agent is incorporated in an oil phase and the minibead comprises a surfactant, e.g. in at least the aqueous phase (polymer matrix). On full dissolution of the composition of the invention in standard 900-1000 mL dissolution pots using compendial medium, the concentration of surfactant in an exemplary embodiment would be of the order of 0.001% i.e. much lower than the amount (around 0.5%-1%) typically added to the dissolution medium. Putting it another way, very significantly greater amounts of surfactant would need to be included in this embodiment of the composition of the invention in order to achieve a fully diluted equivalent concentration of surfactant typically used in 900-1000 mL dissolution pots.

High surfactant concentrations in the dissolution medium can generate very good in vitro data but which is not necessarily predictive of in vivo performance (e.g. pharmacokinetic profile). In contrast, incorporation of (much lower overall quantities of) surfactant in one embodiment of the minibeads of the invention produces unexpectedly superior in-vivo performance. The inventors/applicants hypothesise (without wishing to be bound by the hypothesis) that surfactant in the dissolution medium is more playing the role of a dispersing agent (bringing other components into the dissolution medium) rather than its classical role as an aid to dissolution and that it is the surfactant included in the aqueous phase of this embodiment of the composition of the invention which ensures or enables dissolution. In this setting, the small amount of surfactant included in the dissolution medium therefore makes the test more a dispersion test than a dissolution test and achieves dissolution/dispersion maintenance for the purposes of compendial methods.

Surfactants for the Water-Immiscible Phase

The oil phase, where present, may also include surfactant more hydrophobic than that chosen for the aqueous phase, e.g. a non-ionic surfactant. The surfactant usually has an HLB value of at least 10 but, in any event, less than that of the hydrophilic surfactant. The non-ionic surfactant typically comprises a poly(oxyethylene) group, e.g. comprises a glycerol polyethylene glycol ricinoleate.

Examples include polyethoxylated castor oils (polyethylene glycol ethers) which can be prepared by reacting ethylene oxide with castor oil. Commercial preparations may also be used as the surfactant e.g. those commercial preparations which contain minor components such as, for example, polyethylene glycol esters of ricinoleic acid, polyethylene glycols and polyethylene glycol ethers of glycerol. The preferred example is Cremophor by BASF Corp. also known as Cremophor EL. Alternative or additional surfactants include phospholipids such as, for example, phosphatidylcholine. In embodiments of the composition of the invention which comprise a phospholipid surfactant, the phospholipid surfactant may be incorporated either in the aqueous phase or in the oil phase or both. If at least one phospholipid surfactant is incorporated in each phase, it may be the same phospholipid surfactant in both phases or different in each.

The HLB of the surfactant for the water-immiscible phase, where present, may be from 10-20, e.g. 10-15, and optionally 11-20 (preferably 11-15).

The Dispersed Phase: The Water-Immiscible Phase (Oil Phase)

Any pharmaceutically suitable oil may be used to constitute the oil phase (oil drops) according to the invention. In terms of dry weight of the composition of the invention, the oil phase generally comprises a proportion from 10% to 85%, preferably 15% to 50%, more preferably 20% to 30% or from 35% to 45% e.g. for vaccine formulations. The term "oil" means any substance that is wholly or partially liquid at ambient temperature or close-to-ambient temperature e.g. between 10° C. and 40° C. or between 15° C. and 35° C., and which is hydrophobic but soluble in at least one organic solvent. Oils include vegetable oils (e.g. neem oil), petrochemical oils, and volatile essential oils. The water-immiscible phase in particular comprises a liquid lipid, e.g. a liquid composition comprising triglycerides and/or diglycerides, for example medium chain ($C_6$, $C_7$, $C_8$, $C_8$, $C_9$, $C_{10}$, $C_{11}$ or $C_{12}$) diglycerides or triglycerides or combinations thereof.

Oils which may be included in the oil phase include poly-unsaturated fatty acids such as, for example, omega-3 oils for example eicosapentanoic acid (EPA), docosohexaenoic acid (DHA), alpha-linoleic acid (ALA), conjugated linoleic acid (CLA). Preferably ultrapure EPA, DHA or ALA or CLA are used e.g. purity up to or above 98%. Omega oils may be sourced e.g. from any appropriate plant e.g. sacha inchi. Such oils may be used singly e.g. EPA or DHA or ALA or CLA or in any combination. Combinations of such components including binary, tertiary etc combinations in any ratio are also contemplated e.g. a binary mixture of EPA and DHA in a ratio of 1:5 available commercially under the trade name Epax 6000.

Oils which may be included in the oil phase are particularly natural triglyceride-based oils which include olive oil, sesame oil, coconut oil, palm kernel oil. Oils which are particularly preferred include saturated coconut and palm kernel oil-derived caprylic and capric fatty acids and glycerin e.g. as supplied under the trade name Miglyol™ a range of which are available and from which one or more components of the oil phase of the invention may be selected including Miglyol™ 810, 812 (caprylic/capric triglyceride); Miglyol™ 818: (caprylic/capric/linoleic triglyceride); Miglyol™ 829: (caprylic/capric/succinic triglyceride; Miglyol™ 840: (propylene glycol dicaprylate/dicaprate). Note that Miglyol™ 810/812 differ only in $C_8/C_{10}$-ratio and because of its low $C_{10}$-content, the viscosity and cloud point of Miglyol™ 810 are lower. The Miglyol™ range is available commercially from Sasol Industries. As noted above, oils which may be included in the oil phase need not necessarily be liquid or fully liquid at room temperature. Waxy-type oils are also possible: these are liquid at manufacturing temperatures but solid or semi-solid at normal ambient temperatures.

Alternative or additional oils which may be included in the oil phase according to the invention are medium chain triglyceride compositions such as for example Labrafac™ Lipophile manufactured by Gattefosse in particular product number WL1349. Miglyol™ 810, 812 are also medium chain triglyceride compositions. The medium chain triglyceride(s) mentioned herein are those which comprise one or more triglycerides of at least one fatty acid selected from fatty acids having 6, 7, 8, 9, 10, 11 or 12 carbon atoms, e.g. $C_8$-$C_{10}$ fatty acids.

Other possible (alternative or additional) oils include linoleoyl macrogolglycerides (polyoxylglycerides) such as, for example, Labrafil (e.g. product number M2125CS by Gattefosse) and caprylocaproyl macrogolglycerides such as, for example, Labrasol by Gattefosse.

In one embodiment of the invention, the oil phase comprises more than one component. For example, as just mentioned, the oil phase may comprise a surfactant.

Within this preferred embodiment, it is further preferred that the HLB of the oil be in the range 0-10 (optionally 1-8, e.g. 1-6 and sometimes 1-5) and the HLB of the surfactant be in the range 10-20 and optionally 11-20 (preferably 11-15).

Particularly preferred oils in the lower HLB category include medium chain triglycerides, linoleoyl macrogolglycerides (polyoxylglycerides), caprylocaproyl macrogolglycerides and caprylic/capric triglyceride. In terms of commercial products, particularly preferred oils in the lower HLB range are Labrafac™ Lipophile (e.g. 1349 WL), Labrafil, Labrasol, Captex 355 and Miglyol 810.

Particularly preferred surfactants in the higher HLB category include polyethoxylated castor oils (polyethylene glycol ethers). The preferred commercial product for example is Cremophor.

While higher HLB surfactants can be considered surfactants, the invention also contemplates, additionally or alternatively, inclusion of any other appropriate (non-ionic or other) surfactant in the oil phase.

For certain active principles, particularly hydrophobic/lipophilic agents such as cyclosporin A for example, the present inventors/applicants have observed to their surprise that incorporation into the oil phase of a surfactant of high HLB and an oil of low HLB in a ratio of 1-4:1 by weight, e.g. 1.2-3.0:1 by weight, preferably 1.5-2.5:1 by weight and most preferably 1.8-2.2:1 by weight (high HLB: low HLB) advantageously stabilizes the emulsion before and after immobilization of the oil droplets in the aqueous phase. In this context "stabilize" means in particular that the embodiment improves dissolution and/or dispersion of the composition in vitro.

By "high" HLB in this context is generally intended above 10, preferably from 10-16, e.g. from 12 and 16 or 12 to 14. By "low" HLB is generally intended below 10, preferably in the range 1 to 4, more preferably 1 to 2.

The oil phase preferably also comprises a solvent, miscible with the oil, for the active principle. The oil phase may therefore comprise a liquid lipid and a solvent miscible therewith, in which solvent the water-insoluble active ingredient is soluble. The solvent for the active principle may be miscible with both the liquid lipid and with water.

Examples of suitable solvents are 2-(2-ethoxyethoxy)ethanol available commercially under trade names Carbitol™, Carbitol cellosolve, Transcutol™, Dioxitol™, Polysols DE™, and Dowanal DE™; or the purer Transcutol™ HP (99.9). Transcutol P or HP, which are available commercially from Gattefosse, are preferred. Another possible co-solvent is poly(ethylene glycol). PEGs of molecular weight 190-210 (e.g. PEG 200) or 380-420 (e.g. PEG 400) are preferred in this embodiment. Suitable PEGs can be obtained commercially under the name "Carbowax" manufactured by Union Carbide Corporation although many alternative manufacturers or suppliers are possible.

A particularly preferred oil phase according to the invention is made up of an oil (low HLB), a surfactant (high HLB) and a solvent for the active principle. The oil may be a liquid lipid e.g. an MCT composition. For example the following three commercial products: Transcutol P (as solvent), Miglyol 810 (as oil) and Cremophor e.g. Cremophor EL (as surfactant) is particularly preferred. Miglyol 810 has a low HLB and Cremophor has a high HLB. This particularly preferred oil phase is preferably used to prepare (and is preferably a component of) a composition of the invention comprising cyclosporin. In one embodiment, the composition comprises an oil-soluble or hydrophobic antioxidant e.g. hydralazine or BHT or carnosic acid or vitamin E.

The oil phase may also be a water-in-oil (w/o) emulsion so that the composition of the invention becomes a water-in-oil-in-water (w/o/w) emulsion.

The oil phase may include a said active agent and/or one or more active principles and may also include one or more volatile or non-volatile solvents, which may be the same or different from the solvent or oil phase surfactant previously mentioned. Such solvents may for example remain in the composition of the invention following processing e.g. initial dissolution of the active principle, and have no particular function in the final composition. Alternatively, such solvents if present may function to maintain the active principle in a dissolved state (in solution) within the oil phase or to facilitate dispersion, egress etc. In other embodiments, the solvent may have partly or fully evaporated during processing and therefore be present in only minor quantities if at all. In a related embodiment, the solvent, particularly when a solvent which is both oil and water-soluble is used, may be partly or completely present in the aqueous phase of the composition according to the invention. An example of such a solvent is ethanol. Another example is Transcutol which is already mentioned as a co-solvent.

It will be appreciated, therefore, that the invention provides inter alia a bead or minibead comprising a water-soluble polymer matrix material in which are dispersed droplets of oil, the composition comprising an active principle and the oil comprising a combination of a high HLB compound, e.g. a surfactant, and a low HLB compound, e.g. an oil, and optionally including a co-solvent.

The oil droplets in the aqueous phase in its wet state during manufacture may be small enough (e.g. <100 nm) not to refract light, hence forming a transparent dispersion. This is termed a microemulsion, as is well known in the art.

The Dispersed Phase: The Micelle Phase

As an alternative to an oil or wax phase as described above, the dispersed phase of the colloidal formulations of the invention may comprise micelles, vesicles, liposomes or nanoparticles, or at least the structures which result from drying aqueous colloids of such types. The invention in particular includes formulations in which the dispersed phase is micellar, i.e. formed of micelles and/or promicelles. The term "promicelle" refers to a part of a formulation which will form a micelle upon contact with water, e.g. gastrointestinal contents.

A micelle-forming surfactant is present as micelles dispersed within the hydrogel-forming polymer in a "wet" (not yet dried) composition made as an intermediate in the manufacturing process described herein. It is believed also to be present as micelles in the dried composition but observability of micelles or micelle-like structures in the dried composition is not a requirement of the invention. It is mentioned at this point that the presence of a surfactant in micelle form does not require that the entire surfactant content of a composition is in micelle form as it is considered more probable that a portion of the surfactant will be outside the micelles. Thus in the "wet" composition, whether the hydrogel-forming polymer is in the gel state or the sol (liquid) state may comprise the micelle-forming surfactant at a concentration above the critical micelle concentration.

The diameter of the dispersed micelles may be between 0.5 nm and 200 nm, 1 nm and 50 nm, or 5 nm and 25 nm. The size of the micelles may be determined by dynamic light scattering or diffusion NMR techniques known within the art. Although the size of the micelles is given as a diameter this does not imply that the micelles must be purely spherical species only that they may possess some approximately circular dimension.

The surfactant may be a non-ionic surfactant. The surfactant may be a polyoxyethylated surfactant. The surfactant has a hydrophilic head which may be a hydrophilic chain, for example a polyoxyethylene chain or a polyhydroxylated chain.

The surfactant of course has a hydrophobic part and in particular a hydrophobic chain. The hydrophobic chain may be a hydrocarbon chain, for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ hydrocarbon chains. It may be an alkyl chain, e.g. having a number of carbon atoms just mentioned. It may be an alkenyl chain comprising one or more carbon-carbon double bonds, e.g. having a number of carbon atoms just mentioned. The surfactant may comprise a hydrocarbon chain, e.g. alkyl chain or alkenyl chain, that is substituted provided that it maintains a hydrophobic characteristic. There may for example be one or two substituents, for example a single substituent, e.g. selected from halogen (e.g. F or Cl), hydroxy, thiol oxo, nitro, cyano; hydroxy or thiol substituents may be esterified by for example a fatty acid. One class of surfactants comprise a hydrocarbon monosubstituted by hydroxy; optionally, at least a portion of the hydroxy groups of an aliquot of surfactant, e.g. of the surfactant in a bead, may be esterified by a fatty acid or mono-hydroxy fatty acid as disclosed herein or etherified by a fatty alcohol for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ fatty alcohols.

The hydrophobic chain may be part of an esterified fatty acid $R^1$—COON or of an etherified or esterified fatty ether $R^1$—COH where $R^1$ is the hydrophobic chain, e.g. as mentioned in the preceding paragraph. The ester-forming or, as the case may be, ether-forming group will typically comprise a hydrophilic chain.

As mentioned, the surfactant may have a hydrophilic chain and may be a non-ionic surfactant, and may satisfy both requirements. The hydrophilic chain may be a poly (ethyleneglycol), also known as poly(oxyethylene) or macrogol. The hydrophilic chain may be of the formula —(O—$CH_2$—$CH_2$)$_n$—OR where n is 5 or 6 to 50 and R is H or alkyl, e.g. ethyl or methyl. The invention includes implementations in which n is from 6 to 40, e.g. from 6 to 35. In some embodiments, n is from 6 to 25 and optionally is from 8 to 25 or from 8 to 15. In other embodiments, n is from 8 to 50 or from 8 to 40, e.g. is from 10 to 50, 10 to 40 or 10 to 35. In a particular embodiment, n is 15. For all hydrophilic chains of the formula —(O—$CH_2$—$CH_2$)$_n$—OR, in one class of embodiments R is H.

The hydrophilic chain may be a polyhydroxylated chain (for example a $C_5$-$C_{20}$ e.g. $C_5$-$C_{10}$ chain), e.g. having a hydroxy group on the carbon atoms of the chain, for example a glucamide.

The micelle-forming surfactant may comprise a combination of a hydrophobic chain as described above and a hydrophilic chain as described above. It may therefore be, or comprise, a macrogol ester of a fatty acid as described herein or a macrogol ether of a fatty alcohol as described herein.

Micelle-forming surfactants comprising a hydrophobic chain and a hydrophilic chain can be selected from the group consisting of: macrogol esters; macrogol ethers; diblock copolymers; triblock copolymers; and amphiphilic polymers. In certain embodiments of the invention any combinations of the group are included within the invention.

Examples of macrogol esters which are suitable for use in the present invention are macrogol esters of fatty acids having at least 6 carbon atoms and optionally at least 10 carbon atoms, and particularly of at least 12 carbon atoms; some fatty acids have no more than 22 carbon atoms, for example $C_{10}$-$C_{20}$, $C_{12}$-$C_{20}$ or $C_{15}$-$C_{20}$ fatty acids. The fatty acids may be saturated or unsaturated but are in particular saturated. To be mentioned are macrogol 25 cetostearyl ether (Cremophor® A25); macrogol 6 cetostearyl ether (Cremophor® A6); macrogol glycerol ricinoleate 35 (Cremophor® EL); macrogol-glycerol hydroxystearate 40 (Cremophor® RH 40); macrogol-15-hydroxystearate (Solutol® HS 15). Examples of macrogol ethers which are suitable for use in the present invention are macrogol ethers of fatty alcohols having at least 6 carbon atoms and optionally at least 10 carbon atoms, and particularly of at least 12 carbon atoms; some fatty alcohols have no more than 22 carbon atoms, for example $C_{10}$-$C_{20}$, $C_{12}$-$C_{20}$ or $C_{15}$-$C_{20}$ fatty alcohols. The fatty alcohols may be saturate or unsaturated but are in one embodiment saturated.

Examples of amphiphilic polymers which are suitable for use in the present invention are: alkyl glucamides; fatty alcohol poly(ethoxyl)ates also known as polyethoxylated alkyl ethers; poly(ethoxyl)ated fatty acid esters (Myrj or Solutol); fatty amide polyethoxylate; fatty amine ethoxylate; alkylphenol ethoxylate; polyethoxylated sorbitan esters (polysorbates); polyethoxylated glycerides; or poly-glycerol esters.

Examples of copolymers, which are suitable for use in the present invention are: pluronics(poloxamers); polyvinylpyrrolidone-polyvinylacetate (Plasdone S630); aminoalkyl methacrylate copolymer (Eudragit EPO); methacrylic acid-methyl methacrylate copolymer (Eudragit S100, L100); polycaprolactone-PEG; polycaprolactone-methoxy-PEG; poly(aspartic acid)-PEG; poly(benzyl-L-glutamate)-PEG; poly(D,L-lactide)methoxy-PEG; poly(benzyl-L-aspartate-PEG; or poly(L-lysine)-PEG In a preferred embodiment the micelle-forming surfactant cis a macrogol ester, more preferably a macrogol ester that conforms to the European Pharmacopoeia monograph number 2052 macrogol-15-hydroxystearate, such as Solutol® HS 15 marketed by BASF.

Suitable surfactants comprise those which during manufacture combine with the aqueous phase (including hydrogel-forming polymer) in an amount above their CMC to form a clear liquid. Solutol® HS 15 is such a surfactant.

In certain embodiments the weight ratio of the micelle-forming surfactant to the antigen is from 10:1 to 100:1, optionally from 50:1 to 100:1. In some embodiments, the ratio is from 80:1 to 90:1. In particular embodiments, the ratio is from 50:1 to 60:1.

In particular embodiments, the compositions of the invention comprise a combination of micelle-forming compounds. Such a combination of micelle-forming compounds may consist of two or more surfactants as mentioned in the preceding section of this specification. Alternatively, a surfactant may be combined with one or more other compounds at least potentially able to form micelles with the surfactant, optionally selected from cationic lipids and glycolipids, amongst others. As an additional option, a composition may comprise a plurality of surfactants as mentioned in the preceding section of this specification and one or more other compounds at least potentially able to form micelles with the surfactant, optionally selected from cationic lipids and glycolipids, amongst others.

The invention therefore includes compositions as described herein which comprise:
two or more micelle-forming surfactants, e.g. two or more surfactants having a hydrophobic chain and a hydrophilic chain
a compound, e.g. a single compound or two or more compounds, selected from cationic lipids and glycolipids
two or more micelle-forming surfactants and a compound, e.g. a single compound or two or more compounds, selected from cationic lipids and glycolipids The Aqueous Phase The principal component of the aqueous phase of the colloided formulations according to the invention (preferably between 20% and 70%, more preferably between 30% and 60%, still more preferably between 35% and 55%, by dry weight thereof) is a water-soluble polymer matrix material although other components may also be included as described below. The inclusion of too little of the water-soluble polymer matrix material can for certain active principles lead to non-incorporation or leaching of the active out of the composition, particularly when in the form of minibeads. For certain embodiments, for example micellar compositions, e.g. comprising Solutol®, or those comprising a retardant (see below), it is preferred that the aqueous phase comprise from 55% and 65% of the dry weight of the composition.

In the case of non-colloidal formulations, a minibead may comprise only an aqueous phase (i.e. matrix phase) and optional coating(s).

While mixtures of water-soluble polymer matrix materials are contemplated by the invention, preferably the composition of the present invention comprises a matrix material which is substantially a single material or type of material among those described herein and/or a matrix which can be solidified without inclusion of specific additional polymeric components in the aqueous phase. However, mixtures may be preferred to achieve certain performance characteristics. Thus it may be desired to incorporate certain constraining or retarding substances (retardants) into the water-soluble polymer matrix. In certain embodiments, such incorporation permits a coat (or coating) to be dispensed with. In other embodiments where a constraining or retarding agent is included into the water-soluble polymer matrix, a coat (or coating) may be present and desirable. For example, incorporation of a retarding agent which is insoluble in acid milieu (such as the stomach) is selected to prevent or retard release in the stomach and a coating may not be needed i.e. the composition may be free of a coat/coating. Alternatively, incorporation of a retarding agent which is soluble in acid media may be selected to retard release in the intestine distal to the stomach. Again a coating may not be needed i.e. the composition may be free of a coat/coating. However, a composition according to the invention which incorporates a retarding agent soluble in acid media may optionally be coated e.g. with an acid-resistant polymer to achieve particular advantage. Such a composition is protected from (complete) gastric release (or gastric release is retarded) owing to the effect of the acid-resistant polymer coat. Distal to the stomach, following loss of the coat, the acid-soluble agent retards release because the milieu of the small and large intestine is no longer acid. Retarding or constraining agents insoluble in acid milieu include polymers whose solubility is pH-dependent i.e. soluble at higher pH. Such polymers are described in detail in the section below entitled "Coating" and such polymers may be used either as coats/coatings or as retarding agents incorporated into the water-soluble polymer matrix. An example of a suitable retarding agent mentioned in the section below entitled "Coating" is HPMCP (hydroxy-propyl-methyl-cellulose-phthalate also known as hypromellose phthalate) which is used to prevent release in the gastric environment since it is soluble above pH 5.5—see that section for other examples of polymers soluble in non-acid (basic) media. HPMCP may also be used as a pore-former. Retarding or constraining agents soluble in acid milieu include polymers whose solubility is pH-dependent i.e. soluble at lower pH. Such polymers include cationic polymers such as for example copolymers based on dimethylaminoethyl methacrylate, butyl methacrylate, and methyl methacrylate. An example of such a cationic copolymer which may be used according to the invention is Eudragit E PO commercially available from Evonik Industries.

In one embodiment, the water-soluble polymer matrix material may be of one or more of those selected from gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, hydroxypropylmethyl cellulose, polymerisates of acrylic or methacrylic esters and polyvinylacetate-phthalate and any derivative of any of the foregoing. Mixtures of one or more water-soluble polymers comprising the matrix are also contemplated. In specific embodiments binary or tertiary etc combinations of any of the above substances are foreseen. An unexpected advantage of combining certain water-soluble polymers to form the matrix is that it allows for a reduction in the total amount of water-soluble polymer employed. This may have cost advantages or may allow greater loading of other materials such as, for example, one or more active principles. Inclusion of (addition of) a second water-soluble polymer to form the matrix may also give more strength to the composition of the invention e.g. beads.

In a preferred embodiment, the polymer matrix material is a hydrocolloid i.e. a colloid system wherein the colloid particles are dispersed in water and depending on the quantity of water available can take on different states, e.g., gel or sol (liquid). It is preferred to use reversible hydrocolloids (e.g. agar, gelatin etc) as opposed to irreversible (single-state) hydrocolloids. Thermotropic hydrocolloids (also known as thermoreversable hydrocolloids) can exist in a gel and sol state, and alternate between states with the addition or elimination of heat. Gelatin is a thermo-reversible, rehydratable colloid and is particularly preferred. Gelatin derivatives such as, for example, succinated or phthalated gelatins are also contemplated. Hydrocolloids which may be used according to the invention include those derived from natural sources such as, for example, carrageenan (extracted from seaweed), gelatin (extracted from bovine, porcine, fish or vegetal sources), agar (from seaweed) and pectin (extracted from citrus peel, apple and other fruits). A non-animal based hydrocolloid may be preferred for certain applications e.g. administration to vegetarians or to individuals not wishing to ingest animal products for religious or health reasons. In relation to the use of carrageenan, reference is made to US patent application 2006/0029660 A1 (Fonkwe et al), the entirety of which is incorporated herein by reference.

The immobilized aqueous phase of the composition according to one embodiment of the invention is preferably a gel i.e. a substantially dilute crosslinked system, which exhibits no flow when in the steady-state. The internal network structure of the solidified aqueous phase may result from physical or chemical bonds, as well as crystallites or other junctions that remain intact within an extending fluid e.g. water.

In an alternative preferred embodiment, the polymer matrix is a non-hydrocolloid gum. Examples are the cross-linked salts of alginic acid. For example, aqueous solutions of sodium alginate gums extracted from the walls of brown algae have the well known property of gelling when exposed to di- and trivalent cations. A typical divalent cation is calcium, often in the form of aqueous calcium chloride solution. It is preferred in this embodiment that the cross-linking or gelling have arisen through reaction with such a multivalent cation, particularly calcium.

In an alternative preferred embodiment, the polymer matrix is chitosan which can exist in the form of biogels with or without additives as described e.g. in U.S. Pat. No. 4,659,700 (Johnson & Johnson); by Kumar Majeti N. V. Ravi in Reactive and Functional Polymers, 46, 1, 2000; and by Paul et al. in ST.P. Pharma Science, 10, 5, 2000 the entirety of all 3 of which is incorporated herein by reference. Chitosan derivatives e.g. thiolated entities are also contemplated.

In the embodiment in which gelatin is the polymer matrix of the invention, reference is hereby made to "bloom strength", a measure of the strength of a gel or gelatin developed in 1925 by 0. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

According to the invention, where gelatin is the polymer matrix, it is preferred to use gelatin with bloom strength between 200 and 300, preferably between 210 and 280.

According to the invention, where gelatin is the water-soluble polymer matrix material, the gelatin may be sourced by a variety of means. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for minibead manufacture.

Commercially gelatin can be obtained from the Sigma Chemical Company, St. Louis, Mo. USA or from Nitta (http://www.nitta-gelatin.com).

Lower temperature gelatin (or gelatin derivatives or mixtures of gelatins with melting point reducers) or other polymer matrices able to be solidified at lower temperatures (e.g. sodium alginate described above) are preferred for example when the active principle to be incorporated in the composition of the invention is temperature-labile or whose activity may be affected by exposure to higher temperatures.

According to the invention, where gelatin is the polymer, the starting gelatin material is preferably modified before manufacture to produce "soft gelatin" by the addition of a plasticizer or softener to the gelatin to adjust the hardness of the composition of the invention. The addition of plasticizer achieves enhanced softness and flexibility as may be desirable to optimise dissolution and/or further processing such as, for example, coating. Useful plasticizers of the present invention include glycerin (1,2,3-propanetriol), D-sorbitol (D-glucitol), sorbitol BP (a non-crystallizing sorbitol solution) or an aqueous solution of D-sorbitol and sorbitans (e.g. Andidriborb 85/70). Other or similar low molecular weight polyols are also contemplated. Polyethylene glycol may also be used although this is less preferred and indeed particularly preferred compositions of the invention are free or substantially free of PEG or derivatives thereof. Glycerin and D-sorbitol may be obtained from the Sigma Chemical Company, St. Louis, Mo. USA or Roquette, France.

As noted above, some constituents of the present invention may play more than one role. For example when one of the active principles (see below) is ibuprofen, it may also act as a plasticiser owing to its particular physico-chemical properties. Choice of ibuprofen has particular advantages in relation to higher loading as "conventional" plasticiser, for example dibutyl sebacate or DBS, may be reduced in quantity. Alternatively it is contemplated that the surfactants discussed above may be selected for their plasticiser characteristics to achieve particular advantage.

Softeners, if utilized, can be ideally incorporated in a proportion rising to 30%, preferably up to 20% and more preferably up to 10% by dry weight of the composition of the invention, even more preferably between 3 and 8%, and most preferably between 4% and 6%.

As noted in more detail above in the section on surfactants, it is preferred to include one or more surfactants in the aqueous phase. Certain surfactants may also act as plasticisers or softeners or vice versa.

Although not essential, the aqueous phase may also optionally contain a disintegrant where it is particularly desired to enhance the rate of disintegration of the composition of the invention.

Examples of disintegrants which may be included are alginic acid, croscarmellose sodium, crospovidone, low-substituted hydroxypropyl cellulose and sodium starch glycolate.

A crystallisation inhibitor (e.g. approximately 1% by dry weight of the composition) may also be included in the composition of the invention, preferably in the aqueous phase. An example is hydroxy propyl/methyl cellulose (HMC or HPMC, hypromellose etc) which may play other roles such as, for example, emulsifier (see above). In addition, the aqueous phase may include some or all of a solvent used during processing to dissolve, or facilitate dissolution of, an active principle e.g. an active principle comprised in the oil phase. An example is ethanol (see discussion above on use of solvents in oil phase).

The invention includes compositions comprising a solid phase comprising a water-soluble polymer matrix material and an oil phase dispersed in the solid phase.

Non-Colloidal Formulations

Where the or each active ingredient is water soluble, a single-phase formulation may be used consisting of a water-soluble polymer matrix containing dissolved active ingredient(s) and optional coating(s). The preceding section headed "Aqueous Phase" applies to the matrix phase of such single-phase formulations. The polymer matrix may be formulated as minibeads by ejecting it through a beading nozzle as described above.

Shape, Size and Geometry of Dried Colloidal Formulations

The dried colloidal compositions (i.e. those obtainable by drying a colloid) and dried single phase compositions can be formed into a limitless number of shapes and sizes. In the section below describing the process for making the composition, various methods are given including pouring or introducing a fluid emulsion into a mould where it hardens or can be caused to harden. Thus the composition can be created in whichever form is desired by creating an appropriate mould (e.g. in the shape of a disc, pill or tablet). However, it is not essential to use a mould. For example, the composition may be in the form of a sheet e.g. resulting from pouring a fluid emulsion onto a flat surface where it hardens or can be caused to harden.

Alternatively, the composition may be in the form of spheres or spherical-like shapes made as described below. Preferably, the composition of the invention is in the form of substantially spherical, seamless beads, especially minibeads. The absence of seams on the minibead surface is an advantage e.g. in further processing, for example coating, since it allows more consistent coating, flowability etc. The absence of seams on the minibeads also enhances consistency of dissolution of the minibeads.

The preferred size or diameter range of minibeads according to the invention can be chosen to avoid retention in the stomach upon oral administration of the minibeads. Larger dosage forms are retained for variable periods in the stomach and pass the pyloric sphincter only with food whereas smaller particles pass the pylorus independently of food. Selection of the appropriate size range (see below) thus makes the prediction of therapeutic effect post-dosing more accurate. Compared to a single large monolithic oral format such as, for example, a traditional compressed tablet, a plurality of minibeads released into the GI tract (as foreseen by the present invention) permits greater intestinal lumen dispersion so enhancing absorption via exposure to greater epithelial area, prevents irritation (e.g. as otherwise seen with NSAIDs) and achieves greater topical coating (e.g. as may be desired for local drug effect in certain parts of the GI tract for example the colon). Reduction of residence time in the ileo-caecal junction is another advantage.

The dried colloidal or non-colloidal composition is preferably monolithic meaning internally (i.e. cross-sectionally) homogeneous. This is particularly preferred for the minibead embodiment.

The minibeads mentioned herein generally range in diameter from 0.5 mm to 10 mm with the upper limit preferably 5 mm, e.g. 2.5 mm. A particularly convenient upper limit is 2 mm with 1.7 mm being particularly preferred. The lower limit can preferably be 1 mm, e.g. 1.2 mm, more preferably from 1.3 mm, most preferably from 1.4 mm. In one embodiment the diameter is from 0.5 to 2.5 mm, for example from 1 mm to 2 mm.

In embodiments, the minibeads are monodisperse. In other embodiments, the minibeads are not monodisperse. By "monodisperse" is meant that for a plurality of minibeads (e.g. at least 100, more preferably at least 1000) the minibeads have a coefficient of variation (CV) of their diameters of 35% or less, optionally 25% or less, for example 15% or less, such as e.g. of 10% or less and optionally of 8% or less, e.g. 5% or less. A particular class of polymer minibeads has a CV of 25% or less. CV when referred to in this specification is defined as 100 times (standard deviation) divided by average where "average" is mean particle diameter and standard deviation is standard deviation in particle size. Such a determination of CV is performable using a sieve.

The minibeads may have a CV of 35% and a mean diameter of 1 mm to 2 mm, e.g. 1.5 mm. The minibeads may have a CV of 20% and a mean diameter of 1 mm to 2 mm, e.g. 1.5 mm, e.g. a CV of 10% and a mean diameter of 1 mm to 2 mm, e.g. 1.5 mm. In one class of embodiments, 90% of beads have a diameter of from 0.5 mm to 2.5 mm, e.g. of from 1 mm to 2 mm.

Another possible form of the composition is as hemispherical beads two of which may optionally be joined at the flat face to create a single minibead with two distinct halves, each having a distinct composition, if that is desired, e.g. each containing different active principles or the same active principles but different excipients e.g. to achieve differing permeability, solubilization or release profiles as between the two hemispheres.

The embodiment in which the composition takes the form of minibeads can be further developed to create a larger mass of minibeads e.g. via compression (with appropriate oil or powder-based binder and/or filler known to persons skilled in the art of pharmaceutical formulation) and with the option of including additional quantities of the same active ingredient as in the composition of the invention or a different active ingredient. For example, the composition of the invention may take the form of beads which comprise an active agent or combination of active agents as disclosed herein and the binder or filler comprises MMF, mycophenolate mofetil, an immunosuppressant). A compressed mass of minibeads may disintegrate at a different rate in different conditions than a unitary moulded form of the same shape. The larger (e.g. compressed) mass may itself take a variety of shapes including pill shapes, tablet shapes, capsule shapes etc. A particular problem which this version of the minibead embodiment solves is the "dead space" (above the settled particulate contents) and/or "void space" (between the particulate content elements) typically found in hard gel capsules filled with powders or pellets. In such pellet- or powder-filled capsules with dead/void space, a patient is required to swallow a larger capsule than would be necessary if the capsules contained no such dead space. The minibeads of this embodiment of the invention may readily be compressed into a capsule to adopt the inner form of whichever capsule or shell may be desired leaving much reduced, e.g. essentially no, dead/void space. Alternatively the dead or void space can be used to advantage by suspending minibeads in a vehicle such as, for example, an oil which may be inert or may have functional properties such as, for example, permeability enhancement or enhanced dissolution or may comprise an active ingredient being the same or different from any active ingredients in the bead. For example, hard gelatin capsules may be filled with a liquid medium combined with uncoated and/or coated beads. The liquid medium may be or comprise one or more of the oil phase constituents described herein or it may be one or more surfactants. Particularly preferred but non-limiting examples are corn oil and the commercial products known as Span 85, Labrafac, Transcutol P and Tween 80.

Another possible form of the dried colloidal compositions is as a capsule in which the core of the composition is a solid (e.g. gastro-retentive float material such as, for example, bicarbonate salts) or a fluid (a gas or a liquid). If the core is a liquid, it may contain an active principle and/or excipients which may be the same or different from those described above. Like the hemispherical beads described above, such capsules may have two halves of different constitution and sealed hermetically to retain the internal fluid. An internal layer e.g. internal film layer of non-aqueous material on the inner face of the sphere, may be included if it is desired that the core be an aqueous liquid such that the internal layer prevents the aqueous core from coming into contact with the inner surface of the capsule. With or without an intermediate layer, the core may be a variant of the dried colloidal compositions so that the composition of the invention, in the minibead embodiment, comprises a core made from a first composition according to the invention and a capsule made from a second composition according to the invention.

The minibead embodiment of the invention, while by itself offering a range of solutions to the issues identified above, may also be used as a starting point for creation of further e.g. pharmaceutical or forms for example by using the minibead as a nonpareil seed on which additional layers of material can be applied as is well known to a person skilled in the art e.g. of pharmaceutical science. The material of the additional layers may comprise the same or different active principle and/or the same or different excipients as are described in this document. Such variants allow differential release of the same or different active principles and facilitate inclusion of multiple fixed-dose combination products as for example discussed in connection with the popularly termed "polypill" which denotes a single pill comprising more than one active principle in a fixed dose combination.

The formulations, whether or not dried colloidal formulations, may have a coat of additional material on its outer surface. This coat may be applied in a number of ways, including drug layering, as described more particularly in the section below entitled "coating". In one such embodiment, the formulation comprises an acid within the formulation, for example within a bead, e.g. included within the water soluble polymer matrix or as a liquid core in minibead format and bicarbonate applied as a coat e.g. by drug layering. If the formulation, e.g. minibead, has a polymeric coat, e.g. to control release into the colon, the bicarbonate may optionally or additionally be included in or be absent from the coating polymer. This composition is intended to release carbon dioxide in the GI tract e.g. to reduce pain or to reduce inflammation. The formulation may comprise an acid to enhance the solubility of active principles of various pKa (acid dissociation constant) in the small intestine or colon. Alternatively, the formulation may comprise a base to enhance the solubility of active principles of various pKa in the stomach.

Other Characteristics of Dried Colloidal and Non-Colloidal Formulations

The colloidal compositions, in certain embodiments, comprises one or more elements, components, excipients, structural features, functional features or other aspects of the prior art described above.

To summarise a limited number of embodiments of the invention, the composition as described above and elsewhere herein may additionally be one or more of the following: substantially water-free, in a gel state, in a solid state, undissolved, non-powdered, formed, shaped, and not in solution.

Unless geometrically designed to comprise inner aqueous compartments (e.g. w/o/w format or capsular format with liquid core), it is desirable that the colloidal formulations of the invention are essentially or substantially dry, e.g. contains less than 5%, preferably less than 1% of free water by weight. Minibeads are preferably homogeneous although processing conditions may be varied (see below) to achieve for example heterogeneity such as, for example, a harder skin and softer core with less than complete immobilization of oil droplets towards the core as opposed to the surface of the bead. Larger (e.g. non-beaded) forms or shapes of the composition according to the invention may particularly be engineered to embody such heterogeneity.

The low free-water content is a distinguishing feature of certain embodiments of the colloidal compositions i.e. dried colloidal compositions. The free-water content can be measured using thermogravimetic analysis (TGA), for example with commercially available instrumentation, e.g. using a TGA Q 500 of TA Q series instrument. TGA measures changes in weight in relation to a change in temperature. For example, a TGA method can comprise a temperature scan, e.g. from 20 to 400° C. at 20° C. per minute, where the moisture content is obtained from the sample weight loss at about 100 degrees Celsius.

In one embodiment, the dispersed phase, e.g. oil droplets is homogeneously dispersed in the solidified aqueous phase (or in some embodiments the water-soluble polymer matrix material) with substantial absence of coalescence between adjacent oil droplets. Thus the colloid is preferably maintained during solidification. Coalescence of neighbouring oil droplets or micelles, preferably only does so, if at all, on rehydration of the composition of the invention.

Depending on process parameters, oil droplet size can vary broadly e.g. from 10 nm to 10 µm (diameter). However, the inventors/applicants have found that it is beneficial to maintain droplet size in the range from 100 nm to 1 µm, e.g. from 300-700 nm. The term "emulsion" therefore includes microemulsions and nanoemulsions.

The colloidal compositions generally comprise multiple oil drops or droplets within a moulded or shaped form e.g. a minibead which might typically contain many hundreds or thousands of droplets or micelles as distinct from a powder which generally derives from micron-sized particles incorporating a single or a small number of oil droplets often following coalescence of smaller droplets during spray-drying. While powder embodiments are not excluded, the composition of the invention, if particulate, preferably comprises particles larger than powder particles such that the composition is in a non-powdered form.

Where the formulation is in the form of minibeads, a plurality of minibeads may be presented in a single format e.g. contained in a single hard gel capsule which releases the minibeads e.g. in the stomach. Alternatively the minibeads may be presented in a sachet or other container which permits the minibeads to be sprinkled onto food or into a drink or to be administered via a feeding tube for example a naso-gastric tube or a duodenal feeding tube. Alternatively, the minibeads may be administered as a tablet for example if a plurality of minibeads are compressed into a single tablet as described elsewhere herein. Alternatively, the minibeads may be filled e.g. compressed into a specialist bottle cap or otherwise fill a space in a specialised bottle cap or other element of a sealed container (or container to be sealed) such that e.g. on twisting the bottle cap, the minibeads are released into a fluid or other contents of the bottle or vial such that the beads are dispersed (or dissolve) with or without agitation in such contents. An example is the Smart Delivery Cap manufactured by Humana Pharma International (HPI) S.p.A., Milan, Italy. A related or similar approach is also contemplated for e.g. timed release of mini-capsules into a reactor, feeding environment e.g. tank, incubator etc.

The minibeads so-presented may be of a single type (or population) or may be of multiple types (or populations) differing between populations in relation to one or more features described herein e.g. different API or different excipients or different physical geometry, coated, multiply coated, uncoated etc.

In one embodiment, the invention allows for minibeads having immediate release (IR) characteristics e.g. bearing no coat, enteric-only coat or coat designed to prevent release and/or dissolution of the bead only for a limited time or lacking a retardant in the aqueous phase. In another embodiment, the invention allows for minibeads having delayed or sustained release (SR) characteristics e.g. bearing a coat (or more than one coat) as described in more detail elsewhere herein, particularly in the section entitled "coating". The invention also provides for an embodiment in which immediate release minibeads are produced in combination with a Sustained Release or Controlled Release (CR) minibeads in varying ratios of IR:SR/CR. The immediate release minibeads can be combined with a Sustained or Controlled release minibead component in the following ratios (w/w by potency) e.g. 10% Immediate Release (IR)+90% Sustained (SR)/Controlled Release (CR) minibeads; 20% IR+80% SR/CR; 30% IR+70% SR/CR; 40% IR+60% SR/CR and 50% IR+50% SR/CR.

Other Formulation Formats

The invention is not limited to colloidal formulations and optionally coated matrix phase-only formulations as extensively discussed herein. Insofar as any embodiment permits, an alternative solid oral formulation may be used. For example, two-layer and three-layer seamless minibeads are contemplated, which may be formed by ejecting through a central orifice of a bead-forming nozzle a liquid core material and simultaneously ejecting surrounding layers through one or two orifices arranged concentrically around the central orifice. The outer layer is typically a water-soluble polymer matrix as described herein. The internal phase of a two-layer minibead may have the same constitution as a hydrophobic phase described elsewhere herein.

Those compositions which comprise a macrolide immunosuppressant preferably include a hydrophobic phase in which the immunosuppressant is dissolved. The hydrophobic phase may be a solution, therefore.

Active agents which are more readily water soluble, e.g. the hydroxylase inhibitor hydralazine, may be incorporated in a hydrophilic phase (e.g. a water soluble polymer) in dissolved or particulate form.

Solid dosage forms for oral administration include capsules, minicapsules, beads, powders and granules. In such solid dosage forms, the active compound is typically mixed with at least one inert, pharmaceutically acceptable excipient or carrier such as sodium citrate or dicalcium phosphate and/or one or more: a) fillers or externders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, the formulations contain a dissolution aid. The dissolution aid is not limited as to its identity so long as it is pharmaceutically acceptable. Examples include non-ionic surfactants; ionic surfactants; and amphoteric surfactants.

The solid dosage forms can be prepared with coatings and shells as well known in the pharmaceutical formulating art and described elsewhere herein. They may optionally contain opacifying agents and may also be of a composition such that they release the active ingredient(s) only, or preferentially, in a certain part of the intestinal tract, and/or in delayed fashion.

A solid dosage form may comprise a waxy phase in which one or more active agents are dissolved. Suitable waxy materials are described elsewhere herein.

Active Ingredients

The active agents which may be used in the various aspects of the invention are described under the heading "Brief Summary of the Disclosure" and in the claims. In many cases, the products, methods and uses of the disclosure comprise or involve, or may comprise or involve, a hydroxylase inhibitor. The hydroxylase inhibitor may inhibit an asparaginyl hydroxylase; it may inhibit a prolyl hydroxylase; it may inhibit both. The hydroxylase inhibitor may be selected from, or comprise, DMOG, hydralazine, FG-4497, FG4095, AGN-2979, metirosine, 3-iodotyrosine, aquayamycin, bulbocapnine, oudenone, TM 6008, TM 6089, siRNAs against hydroxylases and antisense therapeutics against hydroxylases, e.g. against PHD1, and combinations thereof. In any event, two or more hydroxylase inhibitors may be used.

In many cases, the products, methods and uses of the disclosure comprise or involve, or may comprise or involve, an immunosuppressant. The identity of the immunosuppressant is not critical. It may be, or comprise, any one or more of: a calcineurin inhibitor, cyclosporin A (ciclosporin); mTOR inhibitors, eg. sirolimus (rapamycin), sirolimus derivatives for example everolimus, 32-deoxorapamycin; a mycophenolate, eg. mycophenolic acid; methotrexate; azathioprine or mercaptopurine; mitoxantrone; cyclophosphamide; macrolide immunosuppressant, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

Some aspects and implementations of the invention involve an active agent selected from calcineurin inhibitors, macrolide antibiotics and mTOR inhibitors.

Exemplary calcineurin inhibitors are cyclosporins, tacrolimus, and pimecrolimus.

For examples of mTOR inhibitors useful in the invention the reader is referred to WO2007/068462, which is incorporated herein by reference in its entirety. Particular examples are rapamycin, 40-O-(2-hydroxy)-ethyl-rapamycin, 32-deoxorapamycin, 40-[3-hydroxy-2-(hydroxymethyl)-2-methylpropanoate]-rapamycin, ABT578 and AP23573.

As examples of macrolide immunosuppressants may be mentioned tacrolimus, ascomycins, sirolimus, cyclosporin, pimecrolimus.

An active agent may be water soluble and dissolved in a water-soluble polymer, e.g. a hydrogel-forming polymer, comprised in the formulation. The polymer may constitute the polymer matrix of a colloidal formulation as extensively described herein.

An active agent may be hydrophobic and dissolved in a hydrophobic medium, e.g. an oil, a wax or the interior of a micelle. The oil, wax or micelle may form the dispersed phase of a colloidal formulation as extensively described herein.

The active agent(s) are usually in solution in a liquid (e.g. an oil or a micelle) or in a solid or semi-solid medium (e.g. a wax or a water-soluble polymer). The second aspect of the invention demands that its minibeads comprise an active agent in solution. It will be recalled in this respect that an active agent may be dissolved in a liquid medium to form a solution which is clear to the human eye prior to manufacturing of the formulation, and the invention includes a formulation obtainable by, i.e. having the characteristics of a formulation obtained by, incorporating such a solution in a minibead or other solid formulation and optionally drying and cooling the minibead or other formulation.

The minibeads of the disclosure provide a hydrophilic environment (the water-soluble polymer) for hydrophilic drugs and a hydrophobic environment (the dispersed phase) for hydrophobic drugs. Hydrophobic drugs are typically in solution in the dispersed phase but suspensions are not excluded. Hydrophilic drugs are often also in solution, in the matrix phase, but may be particulate, e.g. as nanoparticles, in the matrix phase.

The active agents may be used in combination therapy with any other active pharmaceutical ingredient. For example the other ingredient may be an anti-fibrotic agent, for example selected from caspase inhibitors, peroxisome proliferator-activated receptor-g (PPAR-g) agonists such as pioglitazone, TGF-b blockers, colchicines, relaxin, adiponectin, endothelin A, angiotensin receptor blockers, cannabinoids and agents altering the MMP-TIMP balance, and wound healing agent (Ilodecakin, Mannose-6-Phosphate). This is particularly the case in the context of fibrotic disorders of the GIT and their treatment as described herein.

Where two or more actives are use in combination therapy they may be in a combination formulation, e.g. two or more actives may be included in a single population of minibeads or a composition (e.g. capsule or other container) may comprise two or more different populations of minibead, the minibeads of each population having one or more actives not found in the other population. Alternatively, any two actives which are co-administered may be administered in separate formulations, e.g. simultaneously, separately or sequentially and often simultaneously.

As noted above, more than one active principle may be incorporated in a single minibead and/or in distinct populations of minibeads within a single dosage form, e.g. hard gel capsule. The composition of the invention lends itself to fixed dose combinations of particular drugs, e.g. comprising an active agent as described herein with acetylsalicylic acid (ASA)

The present invention also provides methods of treatment of one or more of the above diseases using the composition described herein.

Other Active Excipients

The heading of this section is for convenience only and does not imply strict categorisation. For example, a category, substance or active principle described within this "other active excipients" may also be considered to fall within another section or category in this patent application. One (non-limiting) example is the group of substances known as phospholipids which, according to the invention may be excipients, permeability enhancers or active principles (e.g. phosphatidylcholine which is useful for instance in the treatment of inflammatory bowel disease).

However, in general terms, the invention foresees optional incorporation into the formulation of one or more of the following substances or categories of substances in addition to the primary active agent. For example, the composition may contain a protectant such as, for example, a proteolytic enzyme inhibitor or a protector against acid degradation or both (e.g. an alkali for example sodium hydroxide); an adhesive entity such as, for example, a muco- or bio-adhesive; excipients to maximize solubility of active pharmaceutical compound(s); an antigen(s) and/or an adjuvant(s) to induce an intestinal mucosal or a systemic immune response.

The composition may further comprise excipients to enhance the therapeutic potential of active agents in the ileum and colon including, but not limited to absorption limiters, essential oils such as, for example, omega 3 oils, natural plant extracts such as, for example, neem, ion-exchange resins, bacteria degradable conjugation linkers such as, for example, azo bonds, polysaccharides such as, for example, amylose, guar gum, pectin, chitosan, inulin, cyclodextrins, chondroitin sulphate, dextrans, guar gum and locust bean gum, nuclear factor kappa B inhibitors, acids such as, for example, fumeric acid, citric acid and others, as well as modifications thereof.

The composition may further comprise excipients to reduce systemic side effects associated with absorption in the small intestine including, but not limited to, antioxidants, such as, for example, curcuminoids, flavanoids or more specifically including curcumin, beta-carotene, α-tocopherol, ascorbate or lazaroid.

The composition may further or separately comprise antioxidants (such as, for example, ascorbic acid or BHT-butyl hydroxy toluene) taste-masking or photosensitive components or photoprotective components. Antioxidants may be incorporated in the aqueous phase (e.g. hydrophilic antioxidants) or in the oil phase (e.g. hydrophobic antioxidants such as, for example, vitamin E) for example up to 1% by weight, preferably between 0.01 and 0.50% by weight, more preferably between 0.10 to 0.20% by weight.

Process for Making Colloidal Formulations

The reader is notified that it is important to refer to this section in relation to the Examples.

A basic method for making colloidal formulations is to mix a fluid form (preferably a solution) of the polymer (or mixture of polymers) chosen to be the water-soluble polymer matrix material (e.g. gelatin, gum, alginate etc as described more generally elsewhere herein and in any event optionally in admixture with other components described above) with a dispersed phase material, e.g. a surfactant phase or an oil phase, to form homogeneous fluid emulsion. Taking account of the final composition required (as described elsewhere herein), the dispersed phase and the aqueous phase may be mixed in a proportion in the range 1:6-10, particularly approximately 1:7 or 1:8 for an oily disperse phase or 1:1 to 1:4 for a surfactant (micellar) dispersed phase. In general, only gentle stirring of the components is required using a magnetic or mechanical system e.g. overhead stirrer as would be familiar to a person skilled in the art to achieve emulsification. Continuous stirring is preferred. Any appropriate laboratory stirring apparatus or industrial scale mixer may be utilized for this purpose for example the Magnetic Stirrer (manufactured by Stuart) or Overhead Stirrer (by KNF or Fisher). It is preferred to set up the equipment in such a way as to minimise evaporation of contents such as, for example, water. In one embodiment of the process of the invention, it is preferred to utilise a closed system for stirring in order to achieve this aim.

Where the polymer matrix is substantially constituted by gelatin with the addition of sorbitol, the aqueous phase of polymer matrix is prepared by adding the appropriate quantities of sorbitol (and surfactant and/or active agent, if desired) to water, heating to approximately 60-75° C. until in solution and then adding gelatin although the precise order and timing of addition is not critical. A typical "gelatin solution" comprises 15-25% (preferably 17-18%) gelatin; 75%-85% (preferably 77-82%) of water plus from 1-5% (preferably 1.5 to 3%) sorbitol.

The choice of temperature at which the colloid is formed depends however on various factors include the temperature lability of the active pharmaceutical ingredient and the amount of plasticiser included in the gelatin, the type of gelatin, as well as other factors. Generally however, the gelatin solution (especially in the case of standard or normal gelatin) is maintained at 60° C.-70° C. to maintain it in a fluid state.

The processing temperature can be reduced to a desirable target temperature e.g. 37° C. by use of lower melting-point gelatin (or gelatin derivatives or mixtures of gelatins with melting point reducers) or other polymer matrix material such as, for example, sodium alginate for example when the active principle to be incorporated in the composition of the invention is temperature-labile. Alternatively, temperature-labile active principles may be processed at higher temperatures by using appropriate apparatus or machinery which limits the time during which the temperature-labile active principle is in contact with the higher temperature medium. For example, if gelatin droplets are being formed by machine extrusion and immediately cooled e.g. in a cooling bath, additional appropriate inlet tubing can be used to introduce temperature-sensitive active principle into the fluid gelatin solution (and the mixture can be immediately homogenized) very shortly before ejection from a beading nozzle or other droppletting process such that the duration of exposure of the active principle to the higher temperature gelatin is limited so reducing the degree of any heat-dependent degradation of the active principle. This process may use any appropriate device such as, for example, a homogenizer, e.g. a screw homogenizer, in conjunction with an extrusion-type apparatus as described for example in WO 2008/132707 (Sigmoid Pharma) the entirety of which is incorporated herein by reference.

Hydrophobic surfactant, if included, is added to the aqueous phase conveniently at the same time the other components are added e.g. polymer matrix material and plasticiser if included e.g. at the beginning of the processing session. The physical form of the surfactant at the point of introduction into the aqueous phase during preparation may play a role in the ease of manufacture of the composition according to the invention. As such, although liquid surfactants can be employed, it is preferred to utilize a surfactant which is in solid form (e.g. crystalline or powder) at room temperature, particularly when the aqueous phase comprises gelatin. Surfactant is added in the appropriate amount required to achieve the proportion desired and as described above. In general this leads to presence of surfactant in an amount between 0.8% and 1% (by weight) of the aqueous phase.

The dispersed phase material need not be heated unless it is (semi-)solid at ambient temperature and any active principle and in this case other dispersed phase components are usually added at ambient temperature with stirring until clear. These other components may include a volatile (or non-volatile) solvent in addition to the solvent and/or surfactant if selected. The appropriate amount of oil phase active principle (if any) is added to achieve the target proportion. Stirring can continue for a few minutes to a few hours, even overnight, depending on the active principle (for example, an active may take several hours to be fully dissolved). Where it is desired to include an oil e.g. a wax oil which is not liquid or fully liquid at room temperature (e.g. Solutol or Cremophor RH40) in the dispersed phase, slight warming e.g. to 40-50° C. is appropriate.

The colloid may be formed by addition of the dispersed phase to the heated aqueous phase with stirring as described above. The resultant colloid then has the composition of the solidified minibeads described above but with water still present.

The colloid is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading without delay.

Alternatively to moulding, specialised machinery can be employed for example to create the hemispherical beads described above (see section above entitled "Shape, Size and Geometry") in which the invention takes the form of hemispherical beads. It is possible to manufacture a single bead made from joining two such hemispheres (i.e. a single bead having two distinct halves) by using specialist apparatus in which two tubes through which two different emulsions are flowing, normally of circular cross section, are joined shortly before an extrusion point or nozzle (which may be vibrating) into a single dual lumen tube with a flat wall separating the two emulsion flows and which prevents the two emulsions from coming into contact until the point of extrusion. The cross-section of the joined dual-lumen tube up to the point of extrusion therefore appears as two semi-circles. In operation, the two hemispherical emulsion flows combine to form a single, substantially spherical, bead on extrusion such that normal droplets are ejected/extruded for solidification.

Solidification can occur in a variety of ways depending on the polymer of the matrix, for example by changing the temperature around the mould, vessel, sheet, droplet/bead etc or by applying a solidification fluid or hardening solution so that the moulded shape is gelled or solidified. In certain embodiments both temperature change and application of a solidifying fluid or hardening solution are employed together or simultaneously.

In the preferred embodiment in which the composition of the invention takes the form of minibeads, the minibeads may be formed for example by dropping the liquid colloid dropwise into a fluid which effects solidification. Where the viscosity of the colloid to be beaded reaches a certain point, drop formation becomes more difficult and specialised apparatus is then preferred.

In the case where solidification can be achieved by raising or reducing temperature, the temperature of the solidification fluid can be adapted to achieve solidification at the desired rate. For example, when gelatin is used as the polymer matrix, the solidification fluid is at a lower temperature than the temperature of the emulsion thus causing solidification of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as, for example, calcium chloride) able to induce cross-linking of the alginate and consequent solidification. Alternatively, the same or similar calcium-containing entity may be included (e.g. dispersed) in the aqueous phase of the liquid colloid prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the minibead by control of calcium ion availability (concentration) and other physical conditions (notably temperature). The solidification fluid may be a gas (for example air) or a liquid or both. For example, when gelatin is used as the polymer matrix, the solidification fluid can be initially gaseous (e.g. droplets passing through cooling air) and then subsequently liquid (e.g. droplets passing into a cooling liquid). The reverse sequence may also be applied while gaseous or liquid cooling fluids alone may also be used. Alternatively, the fluid may be spray-cooled in which the colloid is sprayed into a cooling gas to effect solidification.

In the case of gelatin or other water-soluble polymer destined to form the immobilization matrix, it is preferred that the solidification fluid be a non-aqueous liquid (such as, for example, medium chain triglycerides, mineral oil or similar preferably with low HLB to ensure minimal wetting) which can conveniently be placed in a bath (cooling bath) to receive the droplets of emulsion as they solidify to form beads. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the polymer matrix. If a triglyceride is chosen as the cooling fluid in the cooling bath, a preferred example is Miglyol 810 from Sasol.

If gelatin is selected as the polymer matrix, respect for appropriate temperature ranges ensures solidification of the gelatin at an appropriate rate to avoid destruction e.g. of tertiary protein structure in the case where the active principle is a protein.

If alginate is selected as the polymer matrix, a typical method of making minibeads involves dropwise addition of a 3% sodium alginate solution in which oil droplets are dispersed as described above into a 4° C. crosslinking bath containing 0.1 M calcium chloride to produce calcium alginate (this method can be referred to as "diffusion setting" because the calcium is believed to diffuse into the minibeads to effect cross-linking or setting). Using a syringe pump, or Inotech machine, droplets can be generated or extruded (e.g. at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed minibeads can then be stirred in the calcium chloride bath for up to an hour. If carrageenan is used as the polymer matrix both salt and reduction in temperature e.g. by dropping into cooling oil may be used to obtain solidification.

An alternative approach when using alginate is internal gelation in which the calcium ions are dispersed in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Following shape-forming, moulding or beading, the resultant shapes or forms may be washed then dried if appropriate. In the case of minibeads solidified in a solidification fluid, an optional final step in the method of production described above therefore comprises removal of the solidified minibeads from the solidification fluid. This may be achieved e.g. by collection in a mesh basket through which the solidification fluid (e.g. MCT) is drained and the beads retained and is preferably conducted without delay e.g. as soon as the beads have formed or within 5, 10, 15, 20, 25or 30 minutes of their formation. Excess solidification fluid may then be removed using a centrifuge (or other apparatus or machine adapted to remove excess fluid) followed by drying of the beads to remove water or free water and/or removal of some or all of any additional solvent e.g. ethanol or isopropyl alcohol used to dissolve or facilitate dissolution of the active principle in preceding steps optionally followed by washing (e.g. using ethyl acetate) and a subsequent "drying" step to remove excess solvent (e.g. ethyl acetate). Isopropyl alcohol is an example of a solvent which is preferably removed later in processing to reduce residues in the oil or aqueous phase. Drying can be achieved by any suitable process known in the art such as use of a drum drier (e.g. Freund Drum dryer which may be part of the Spherex equipment train if used) with warm air at between 15° C. and 25° C., preferably around 20° C. leading to evaporation or entrainment of the water by the air. Use of gelatin as the polymer matrix (e.g. as principal constituent of the aqueous immobilisation phase) in most cases requires a drying step and for minibeads this is preferably achieved by drying in air as above described. The resultant composition (the composition of the invention) is essentially dry as described in more detail above.

In terms of the way in which colloid droplets may be formed in the first step of the beading process described above, variations of the above described method are possible including introducing droplets into a variety of solidification fluids.

In general, the minibeads may be generated by the application of surface tension between the fluid colloid having an aqueous continuous phase and an appropriate solidification fluid such as, for example, gas or liquid in order to create the spherical or substantially spherical shape of the ultimate beads.

Alternatively, the minibeads may be produced through ejection or extrusion of the liquid colloid through an orifice or nozzle with a certain diameter and optionally subject to selected vibrational frequencies and/or gravitational flow. Examples of machines which may be used are the Freund Spherex, ITAS/Lambo, Globex or Inotech processing equipment. Operation of the Spherex machine manufactured by Freund as may be desired to manufacture minibeads according to the present invention is described in U.S. Pat. No. 5,882,680 (Freund), the entire contents of which are incorporated herein by reference. It is preferred to select a vibrational frequency in the region of 10-15 RPM although the ultimate choice (and separately the amplitude of vibration selected) depends on the viscosity of the colloid to be beaded. If the polymer matrix is chosen to solidify at lower temperature, it may be appropriate to maintain the lines to the orifice/nozzle at a certain temperature to maintain the fluidity of the solution.

The Spherex machine (and others) may be adapted to make use of a dual concentric lumen nozzle to ensure simultaneous extrusion of two fluids, the fluid in the inner lumen forming a core and the fluid of the outer lumen forming a capsule. The fluid forming the capsule is solidified according to one of the methods described. It may or may not be desirable for the fluid forming the core to be susceptible of solidification to yield a particular embodiment of the composition of the invention. The machinery adapted in this way can be used to manufacture the composition of the invention in the form of a capsule in which the core of the composition is filled with a fluid (a gas or a liquid) as described in the section above entitled "Shape, Size and Geometry" (noting that the core, like the capsular material, may be a composition, albeit optionally a distinct composition, according to the invention i.e. susceptible of solidification according to one of the methods described above). A three-lumen nozzle and appropriate tubing may be employed if it is desired to include an intermediate internal layer e.g. internal film layer of non-aqueous material on the inner face of the sphere with the intermediate layer conveniently being solid at room temperature. Thus, in terms of the softness/hardness of successive layers, the composition may for example be described as solid:solid in the case of two layers or solid:solid:solid in the case of 3 layers or liquid/semi-liquid:solid:solid in the case of 3 layers.

The preceding paragraphs describe the formation of uncoated beads. It is a preferred embodiment of the present invention to have coated beads which are described in more detail elsewhere herein. Such coatings may be single or multiple and may be applied in a number of ways (see separate section).

With regard to one of the methods described above (ejection of colloid through an optionally vibrating nozzle) with two concentric orifices (centre and outer), the outer fluid may form a coat (outside the minibead) of e.g. polymeric material (polymeric coating) which may contain an active principle or may impart controlled release characteristics to the minibead and the inner layer (core) may be a colloid as described herein. The Spherex machine manufactured by Freund (see U.S. Pat. No. 5,882,680 to Freund) is preferably used (the entire contents of this patent is incorporated herein by reference).

Use of the Spherex machine achieves very high monodispersity. For example, in a typical 100 g, batch 97 g of minibeads were between 1.4 to 2 mm diameter or between 1 and 2 mm. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to coat the minibeads (if smaller, the spray of the coating machine may bypass the minibead; if too large hard, the beads may be harder to fluidise which is necessary to achieve consistent coating).

The minibeads are preferably internally (i.e. cross-sectionally) homogeneous i.e. monolithic although processing conditions may be varied for example by altering the temperature of the liquid colloid, the solidification fluid and the concentration of components in these fluids and the time allowed for certain processing steps to occur including drying. Although not currently preferred, such variations may be applied in the case of minibead manufacture to achieve heterogeneity such as, for example, a harder skin and softer core with less than complete immobilization of oil droplets towards the core as opposed to the surface of the bead. Larger (e.g. non-beaded) forms or shapes of the composition according to the invention may particularly be engineered to embody such heterogeneity. However, it is currently preferred to have internally homogenous compositions and, within the minibead embodiment, this can be favoured by conducting the beading/droppletting using a homogeneous medium e.g. a well dispersed colloid. Such homogeneity in the emulsion to be beaded can help avoid the drying conditions affecting symmetry.

The oral composition may be used for a number of applications as discussed elsewhere herein. The active principle(s) may be released immediately (immediate release profile) or be released after some delay and/or over an extended period (delayed and/or extended release profile). For immediate release, the minibeads or other formats may be uncoated or coated enterically to protect against stomach acid for immediate release in the small intestine.

Alternatively, if controlled release is desired (i.e. delayed, extended or site-targeted release etc), or if medium-independent release is desired, it is possible, according to the invention to apply a coat to the minibeads or other formats. Application of the appropriate coat may, for example if colonic release is required, allow for say less than 10% of the active principle to be dissolved (in dissolution medium) at 4 hours and then a burst (sudden release) towards a maximum dissolution (approaching 100%) in the subsequent 24 hours. Many alternative target profiles are possible and this example is purely for illustration.

Thus, the composition may be in the form of minibeads at least some of which bear a coat (i.e. are coated) in order to control release of active principle from the minibead. In one embodiment, the coat is a film and in another embodiment, it is a membrane. The coat, film or membrane comprises one or more substances preferably of a polymeric nature (e.g. methacrylates etc; polysaccharides etc as described in more detail below) or combination of more than one such substance, optionally including other excipients or active principles, such as, for example, plasticizers, described e.g. in the sections above on active principles. Preferred plasticizers, if they are used, include hydrophilic plasticizers for example triethyl citrate (TEC) which is particularly preferred when using the Eudragit family of polymers as coatings as described below. Another preferred plasticiser, described in more detail below in relation to coating with ethyl cellulose, is DBS. Alternative or additional optionally included excipients are glidants. A glidant is a substance that is added to a powder or other medium to improve its flowability. A typical glidant is talc which is preferred when using the Eudragit family of polymers as coatings.

Non-Colloidal Formulations

In the case of non-colloidal formulations comprising a water-soluble polymer matrix, the same methods may be followed as just described for colloidal formulations but without the involvement of a dispersed phase.

Coating

In the case of combinations of polymers, combinations may be selected in order to achieve the desired delay (or other change) in the release of the drug and/or poration of the coating and/or exposure of the minibead or other format within the coating to allow egress of drug and/or dissolution of the immobilization matrix. In one embodiment, two types of polymers are combined into the same polymeric material, or provided as separate coats that are applied to the minibeads.

It has previously been stated that the formulations may comprise more than one population of minibeads. Within the coating embodiment, the differences between populations may lie in the coat i.e. two (or more) populations of minibeads may differ in a number of respects one of which is the coating.

The coat may be applied as described below and may vary as to thickness and density. The amount of coat is defined by the additional weight added to (gained by) the dried composition (e.g. minibead) of the invention. Weight gain is preferably in the range 0.1% to 50%, preferably from 1% to 15% of the dry weight of the bead, more preferably in the range 3% to 10% or in the range 5-12% or in the range 8-12%.

The polymeric coating material may comprise methacrylic acid co-polymers, ammonio methacrylate co-polymers, or mixtures thereof. Methacrylic acid co-polymers such as, for example, EUDRAGIT™ S and EUDRAGIT™ L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a variety of pH levels, e.g. between the pHs at which EUDRAGIT™ L and EUDRAGIT™ S are separately soluble.

The trademark "EUDRAGIT" is used hereinafter to refer to methacrylic acid copolymers, in particular those sold under the EUDRAGIT™ by Evonik.

The coating can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as, for example, EUDRAGIT™ RS and EUDRAGIT™ RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCl) groups in the polymer. For example, those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability. A particularly preferred diffusion-controlled pH-independent polymer in this family is RS 30 D which is a copolymer of ethyl acrylate, methyl methacrylate and a low content of methacrylic acid ester with quaternary ammonium groups present as salts to make the polymer permeable. RS 30 D is available as an aqueous dispersion.

The amino methacrylate co-polymers can be combined in any desired ratio, and the ratio can be modified to modify the rate of drug release. For example, a ratio of EUDRAGIT™ RS: EUDRAGIT™ RL of 90:10 can be used. Alternatively, the ratio of EUDRAGIT™ RS: EUDRAGIT™ RL can be about 100:0 to about 80:20, or about 100:0 to about 90:10, or any ratio in between. In such formulations, the less permeable polymer EUDRAGIT™ RS generally comprises the majority of the polymeric material with the more soluble RL, when it dissolves, permitting gaps to be formed through which solutes can come into contact with the minibead allowing pre-dissolved pharmaceutical actives to escape in a controlled manner.

The amino methacrylate co-polymers can be combined with the methacrylic acid co-polymers within the polymeric material in order to achieve the desired delay in the release of the drug and/or poration of the coating and/or exposure of the minibead within the coating to allow egress of drug and/or dissolution of the immobilization or water-soluble polymer matrix. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the minibeads.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. A further example is EUDRAGIT® L 30D-55 which is an aqueous dispersion of anionic polymers with methacrylic acid as a functional group. It is available as a 30% aqueous dispersion.

In addition to the EUDRAGIT™ polymers described above, a number of other such copolymers can be used to control drug release. These include methacrylate ester co-polymers such as, for example, the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114 the entirety of which is incorporated herein by reference.

Several derivatives of hydroxypropyl methylcellulose (HPMC) also exhibit pH dependent solubility and may be used in the invention for coating. These include hydroxypropyl methylcellulose phthalate (HPMCP), which rapidly dissolves in the upper intestinal tract and hydroxypropyl methylcellulose acetate succinate (HPMCAS) in which the presence of ionizable carboxyl groups causes the polymer to solubilize at high pH (>5.5 for the LF grade and >6.8 for the HF grade). These polymers are commercially available from Shin-Etsu Chemical Co. Ltd. As with other polymers described herein as useful for coatings, HPMC and derivatives may be combined with other polymers e.g. EUDRAGIT RL-30 D.

It is particularly preferred according to the invention to use a polymeric coating substance which is pH-independent in its dissolution profile and/or in its ability to release active principles incorporated in the minibeads of the invention. Examples have already been given (e.g., Eudragit RS and RL). Another example of a pH-independent polymeric coating substance is ethylcellulose, in particular a dispersion of ethylcellulose in a sub-micron to micron particle size range, e.g. from about 0.1 to 10 microns in size, homogeneously suspended in water with the aid of an emulsification agent, e.g. ammonium oleate. The ethylcellulose dispersion may optionally and preferably contain a plasticizer, for example dibutyl sebacate (DBS) or medium chain triglycerides. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark Surelease®, by Colorcon of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "Surelease®" is used hereinafter to refer to ethylcellulose coating materials, for example a dispersion of ethylcellulose in a sub-micron to micron particle size range, e.g. from about 0.1 to 10 microns in size, homogeneously suspended in water with the aid of an emulsification agent, e.g. ammonium oleate. In particular, the trademark "Surelease®" is used herein to refer to the product marketed by Colorcon under the Surelease® trademark.

Surelease® dispersion is an example of a combination of film-forming polymer, plasticizer and stabilizers which may be used as a coating to adjust rates of active principle release with reproducible profiles that are relatively insensitive to pH. The principal means of drug release is by diffusion through the Surelease® dispersion membrane and is directly controlled by film thickness. Use of Surelease® is particularly preferred and it is possible to increase or decrease the quantity of Surelease® applied as coating in order to modify the dissolution of the coated minibead. Unless otherwise stipulated, use of the term "Surelease" may apply to Surelease E-7-19020, E-7-19030, E-7-19040 or E-7-19050. E-7-19020 comprises ethylcellulose blended with oleic acid and dibutyl sebacate, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. E-7-19030 additionally comprises colloidal anhydrous silica dispersed into the material. E-7-19040 is like E-7-19020 except that it comprises medium chain triglycerides instead of dibutyl sebacate. E-7-19050 derives from blending ethylcellulose with oleic acid before melting and extrusion. The molten plasticized ethylcellulose is then directly emulsified in ammoniated water in a high shear mixing device under pressure. Ammonium oleate is formed in situ to stabilize and form the dispersion of plasticized ethylcellulose particles. However, E-7-19040 is preferred.

The invention also contemplates using combinations of Surelease with other coating components, for example sodium alginate, e.g. sodium alginate available under the trade name Nutrateric™.

In addition to the EUDRAGIT™ and Surelease® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as, for example, sodium lauryl sulfate and polysorbates, organic acids such as, for example, acetic acid, adipic acid, citric acid, fumaric acid, glutaric acid, malic acid, succinic acid, and tartaric acid, sugars such as, for example, dextrose, fructose, glucose, lactose, and sucrose, sugar alcohols such as, for example, lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 all of which are incorporated herein by reference in their entirety.

As noted above, Surelease is a particularly preferred polymer coating owing to its pH-independent dissolution character. However, the inventors/applicants have found that it is difficult to select the appropriate amount (weight gain) of Surelease to achieve optimal dissolution. It has been found that too much Surelease leads to incomplete (or over slow) dissolution while too little leads to over fast dissolution.

The inventors/applicants have found that addition to Surelease™ of a second polymer (e.g. a polysaccharide, especially a heteropolysaccharide) which is normally degraded by bacterial enzymes but not by digestive enzymes, e.g. human digestive enzymes, resolves this problem and provides flexibility in modulating the amount of polymer added to the minibeads of the invention in order to achieve optimal dissolution profiles. In general terms, therefore, the disclosure includes formulations as described herein which comprise a coating comprising a combination of a delayed release material, for example an erodible polymer e.g. ethylcellulose, and a polymer susceptible of degradation by bacterial enzymes in the colon, e.g. a polysaccharide and particularly a water soluble polysaccharide, particularly a pectin.

The disclosure therefore includes a coating for compositions intended to release their active payload in the colon which is a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan etc and derivatives of any of the foregoing. Chitosan is particularly preferred in connection with obtaining a colon-specific release profile. The disclosure also includes a composition comprising a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon; the composition may include a liquid vehicle, e.g. water.

The use of polysaccharides by themselves for coating purposes has been tried with limited success. Most of the non-starch polysaccharides suffer from the drawback of lacking good film forming properties. Also, they tend to swell in the GI tract and become porous, resulting in the early release of the drug. Even amorphous amylose, which is resistant to degradation by pancreatic alpha amylase but capable of degradation by colonic bacterial enzymes has the disadvantage of swelling in aqueous media although this can be controlled by incorporating insoluble polymers like, ethyl cellulose and acrylates into the amylose film. Amylose however is not water-soluble and although water-soluble polysaccharides are not excluded, the present inventors have found that use of a water-soluble polysaccharide (WSP) susceptible of bacterial enzymic degradation brings particularly advantageous results when used as a coating in accordance with this embodiment of the present invention. A particularly preferred polysaccharide in this embodiment of the present invention is pectin. Various kinds of pectin may be used including pectin of different grades available i.e. with differing degrees of methylation (DM), i.e. percentage of carbonyl groups esterified with methanol, for example pectins with a DM of more than 50%, known as High Methoxy (HM) Pectins or Low Methoxy (LM) pectins, or a pectin combination comprising an HM pectin and an LM pectin. It is also possible in this embodiment to use pectins having various degrees of acetylation (DAc). Taken together, the DM and DAc or the degree of substitution is known as Degree of Esterification (DE). Pectins of various DE's may be used according to the invention. As an alternative to pectin, sodium alginate may be used as a polysaccharide according to an embodiment of the invention. However, other embodiments may conveniently include amylose and/or starch which contains amylose. Various grades of starch, containing different percentages of amylose may be used including for example Hylon V (National Starch Food Innovation) which has an amylose percentage of 56% or Hylon VII which has an amylose percentage of 70%. The remaining percentage is amylopectin. The polysaccharides pectin, amylose and sodium alginate are particularly preferred for achieving colon delivery i.e. for compositions intended to release active principles in the colon.

It has been found that pectin can act as a former of pores in the coating otherwise provided by ethylcellulose (preferably Surelease). By "pores" is not meant shaft-like holes from the surface to the core of the minibead, rather areas of weakness or absence of coating occurring stochastically on and within the coating of the invention.

Pore formers have been described before in connection with Surelease (see e.g. US 2005/0220878) but in relation to "gastro-insoluble" substances such as, for example, alginate.

Where the water-soluble polysaccharide (WSP) is pectin, the proportion of ethylcellulose or Surelease™ to pectin is ideally in the range 90:10 to 99:1, preferably, 95:5 to 99:1, more preferably 98:2 to 99:1.

In this particularly preferred combination (ethylcellulose or Surelease™+ WSP e.g. pectin) the weight gain and ratio between ethylcellulose or Surelease™ and WSP can be varied to refine the behaviour of the coating and the composition of the invention when it bears such a coat. Thus to the inventors/applicant's surprise, the advantages of this preferred combination of coating polymers were further pronounced by selecting a weight gain in the range 0 to 30% (preferably 5 to 10%) and a weight ratio of ethylcellulose or Surelease to pectin in the range 95:5 to 99.5:0.5 preferably 97:3 to 99:1 inclusive. Particularly favoured weight gains using ethylcellulose or Surelease are those in the range 5-12% or in the range 8-12%.

Although the focus above has been on extending and/or sustaining release of active principles from minibeads or other formats, also contemplated are uncoated or simple enteric coated minibeads or other formats providing early, small intestinal API release with sufficient enteric coating merely to protect the minibeads from dissolution in the stomach.

It is preferred to dry the minibeads before they are coated with a suitable polymeric coat (as described in more detail above/below). It is also preferred, in certain embodiments to apply a first coat before applying a second. In general the first coat and the second coat may be of the same or different materials and be chosen from any of the classes of coating material described herein. In specific embodiments, the first coat optionally protects the core (bead) from interaction with the second coat and/or prevents leaching of bead contents into the second coat. For example, the first coat may comprise or consist of a mixture of hypromellose, titanium dioxide and polyethylene glycol; the second (outer) coat in this instance may comprise, or consist of, a mixture of ethylcellulose and pectin or another polymer, e.g. water-soluble polysaccharide, susceptible to degradation by bacterial enzymes in the colon, and in particular may be the Surelease®-pectin mixture described above. If it is desired for the first coat to use a mixture of hypromellose, titanium dioxide and polyethylene glycol, commercial products corresponding to such mixtures are available including Opadry® White, a product commercialised by Colorcon. More generally, various products commercialised under the trade name Opadry and Opadry II. Further nonlimiting examples include Opadry YS-1-7706-G white, Opadry Yellow 03B92357, Opadry Blue 03B90842). These compositions are available as dry film coating compositions that can be diluted in water shortly before use. Opadry and Opadry II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable OPADRY or OPADRY II formulations may comprise a plasticizer and one or more of maltodextrin, and polydextrose (including but not limited to a) triacetin and polydextrose or maltodextrin or lactose, or b) polyethylene glycol and polydextrose or maltodextrin). Particularly preferred commercial products are Opadry White (HPMC/HPC-based) and Opadry II White (PVA/PEG-based). Alternative (non-Opadry) products for initial protective coats include polyvinyl alcohol-polyethylene glycol graft copolymers such as is available commercially under the name Kollicoat IR and methyl methacrylate ammonium-based copolymers such as are available commercially under the name Eudragit E. Another preferred example is low molecular weight HPMC. The optional inner coat is applied in the same manner as is the outer (or sole) coat (or coating layer).

The coating process can be carried out by any suitable means such as, for example, by use of a coating machine which applies a solution of a polymer coat (as described above in particular) to the minibeads. Polymers for coating are either provided by the manufacturer in ready-made solutions for direct use or can be made up before use following manufacturers' instructions.

Appropriate coating machines are known to persons skilled in the art and include, for example, a perforated pan or fluidized-bed system for example the GLATT, Vector (e.g. CF 360 EX), ACCELACOTA, Diosna, O'Hara and/or HICOATER processing equipment. Most preferred is the MFL/01 Fluid Bed Coater (Freund) used in the "Bottom Spray" configuration.

Typical coating conditions are as follows:

| Process Parameter | Values |
| --- | --- |
| Fluidising airflow (m3/h) | 20-60 (preferably 30-60) |
| Inlet air temperature (° C.) | 20-65 |
| Exhaust air temperature (° C.) | 38-42 |
| Product temperature (° C.) | 38-42 |
| Atomizing air pressure (bar) | Up to 1.4 e.g. 0.8-1.2 |
| Spray rate (g/min) | 2-10 and 3-25 RPM |

Whether as part of the polymeric coat or independently thereof, the minibeads of the invention may be coated with additional drug layers using methods conventional in the art of pharmaceutical science (such as for example using coating machines as just described) to produce a composition having one or more layer(s), each layer containing one or more active pharmaceutical or other ingredient/excipient as described elsewhere herein. Drug layering means the deposition of at least one or successive layers of drug entities from solution, suspension or dry powder on nuclei e.g. minibeads as described herein. Drug layering includes solution/suspension layering, powder layering and powder drug layering. In solution/suspension layering, drug particles are dissolved or suspended in a binding liquid. In powder layering, complete dissolution does not occur, due to low liquid saturation, irrespective of the solubility of the active agent in the binding liquid. In powder drug layering, a binder solution is first sprayed onto previously prepared inert seeds e.g. minibeads as described herein, followed by the addition of powder. Conventional pan coaters may be used as described above for polymer coating although modified forms of pan coaters are preferred including fluidised-bed and centrifugal rotary granulators. Examples of suitable granulators include the Rotor granulator. (Glatt), the Rotor-processor (Aeromatic), the Spir-a-Flow (Freund) and the CF-granulator (Freund). In applying a drug layer, the drug to be layered onto the minibead may optionally first be admixed with appropriate excipients such as, for example, binders as described elsewhere herein. A particularly preferred binder in this context is polyvinyl pyrrolidone (also spelt polyvinylpyrrolidone and also known as PVP or povidone). PVPs of various K-values may be used. The K-value of PVP is a function of its average molecular weight, the degree of polymerization, and the intrinsic viscosity. It is particularly preferred to use PVP K-32. Up to 5% of the dry weight of the composition of the invention in this embodiment may be made up of such binders. Approximately 1% or less is preferred. Other suitable binders which may be used in drug-layering include gelatin, carboxymethyl cellulose, hydroxypropyl methylcellulose and hydrolysed starches e.g. maltodextrins. Compositions embodying drug layering may also optionally be coated with a polymer coating, or include a polymer layer, to control release as described more generally above including the option to include the same or a different active principle in this polymer coat.

The layered bead or minibead may have a plurality of layers, e.g. 2, 3, 4 or 5 layers, comprising an active principle, wherein the active principle of each layer is selected independently from the active principle of each other layer. In one embodiment, each layer comprises the same active principle as each other layer; in another embodiment, no two layers comprise the same active principle. The term "active principle" in this paragraph embraces both a single active entity and a combination of active entities. The layered bead or minibead may comprise one or more polymer layers, to control release as described more generally above. Such a polymer layer may contain an active principle and therefore constitute a drug layer as well as a release control layer. Alternatively, a polymer layer may be free of active principle. A polymer layer, whether or not it contains an active principle, may be located between the core and a drug layer outside the polymer layer, or between two drug layers, or may form an outer layer.

The polymer layer may be located between the core and the active principle layer. The polymer layer may be located externally of the active principle layer. The layered bead or minibead may comprise a plurality of active principle layers and, additionally or alternatively, it may comprise a plurality of polymer layers. In some embodiments, there is at least one active principle layer which comprises a release-controlling polymer. In some embodiments, the outermost layer comprises a release-controlling polymer, which may contain an active principle or, in another implementation, be free of active principle.

The optionally coated minibeads of the invention may be formulated directly following their manufacture in the ways described above. In an alternative embodiment, it may be desired to impart different properties to the minibeads and/or to a final solid dosage product. One way of achieving this according to the invention is through granulation e.g. to improve the flow of powder mixtures of minibeads with other components as e.g. described above in relation to binders. Granules of intact or broken minibeads may be obtained by adding liquids (e.g. binder or solvent solutions) and effecting a granulating step as described in the prior art. Larger quantities of granulating liquid produce a narrower particle size range and coarser and harder granules, i.e. the proportion of fine granulate particles decreases. The optimal quantity of liquid needed to get a given particle size may be chosen in order to minimise batch-to-batch variations. According to this embodiment, wet granulation is used to improve flow, compressibility, bio-availability, homogeneity, electrostatic properties, and stability of the composition of the invention presented as a solid dosage form. The particle size of the granulate is determined by the quantity and feeding rate of granulating liquid. Wet granulation may be used to improve flow, compressibility, bio-availability, and homogeneity of low dose blends, electrostatic properties of powders, and stability of dosage forms. A wet granulation process according to this embodiment may employ low or high shear mixing devices in which a low viscosity liquid (preferably water) is added to a powder blend containing binder previously dry mixed with the rest of the formulation including minibeads. Alternative granulation approaches which may be utilized include high-shear, extrusion and conventional wet granulation.

The invention further includes the subject matter of the following clauses:

1. A pharmaceutical composition for oral administration, comprising a unit solid which comprises a water-soluble polymer matrix material in which matrix material are dispersed a water-insoluble active ingredient selected from calcineurin inhibitors, mTor inhibitors and macrolide immunosuppressants; droplets of water-immiscible liquid in which the water-insoluble active ingredient is soluble; and a hydrophilic surfactant having an HLB value of at least 10, the composition being adapted to release water-insoluble active ingredient in at least the colon and the water-insoluble active ingredient being for therapeutic use in combination therapy with a hydroxylase inhibitor.
2. A composition of clause 1 which comprises gelatin as the water-soluble polymer.
3. A composition of clause 2 in which gelatin is substantially the only water-soluble polymer.
4. A composition of any preceding clause wherein the water-soluble matrix material is selected from a hydrocolloid, a non-hydrocolloid gum and chitosan and derivatives thereof.
5. A composition of any preceding clause wherein the unit solid is a minibead having a diameter of not more than 10 mm, e.g. of not more than 5 mm, the composition optionally comprising a plurality of said minibeads.
6. A composition of clause 5 wherein the minibead is monolithic, optionally with layers thereon.
7. A composition of clause 5 or clause 6 wherein the one or more minibeads comprise a controlled-release polymer.
8. A composition of clause 7 wherein the controlled-release polymer is an extended release polymer or an enteric polymer.
9. A composition of clause 7 or clause 8 in which the minibead has a coat which comprises the controlled release polymer and optionally a polymer susceptible of degradation by bacterial enzymes.
10. A composition of clause 7 wherein the controlled-release polymer is ethylcellulose comprised in a coating on the minibead and optionally in association with an emulsification agent, for example ammonium oleate.
11. A composition of clause 10 wherein the ethylcellulose is also in association with a plasticizer, e.g. dibutyl sebacate or medium chain triglycerides.
12. A composition of clause 10 or clause 11 wherein the coating further comprises polymer susceptible of degradation by bacterial enzymes.
13. A composition of clause 12 wherein the polymer susceptible of degradation by bacterial enzymes is water-soluble, preferably pectin.
14. A composition of any preceding clause wherein the hydrophilic surfactant has an HLB value of at least 15, and optionally of at least 18.
15. A composition of any preceding clause wherein the hydrophilic surfactant is an anionic surfactant.
16. A composition of clause 15 wherein the anionic surfactant has an HLB value of at least 30.
17. A composition of clause 15, wherein the anionic surfactant comprises or is an alkyl sulfate salt.
18. A composition of clause 16 in which the alkyl sulfate salt is sodium dodecyl sulfate (SDS)
19. A composition of any of clauses 15 to 18 in which the water-soluble polymer matrix material further contains a non-ionic surfactant having an HLB value of at least 10 but less than that of the hydrophilic surfactant.
20. A composition of clause 19 wherein the non-ionic surfactant comprises a poly(oxyethylene) group.

21. A composition of clause 20 wherein the non-ionic surfactant comprises a glycerol polyethylene glycol ricinoleate.
22. A composition of any preceding clause in which the water-immiscible liquid comprises a liquid lipid and a solvent miscible therewith, in which solvent the water-insoluble active ingredient is soluble.
23. A composition of clause 22 when dependent on any of clauses 19 to 21, in which the ratio of liquid lipid to non-ionic surfactant is in the range 1-4:1 by weight, optionally 1.2-3.0:1 by weight.
24. A composition of clause 22 or clause 23 in which the liquid lipid is a medium chain triglyceride composition, the medium chain triglyceride(s) being one or more triglycerides of at least one fatty acid selected from $C_6$-$C_{12}$ fatty acids.
25. A composition of clause 24 wherein the liquid lipid is a caprylic/capric triglyceride.
26. A composition of clauses 22 to 25 in which said solvent is miscible with both the liquid lipid and with water.
27. A composition of clause 26 in which the solvent is 2-(2-ethoxy)ethanol.
28. A composition of any preceding clause in which the water-immiscible phase (water-immiscible droplets) represent from 10-85% by dry weight of the composition.
29. A composition of any preceding clause in which the unit solid or minibead has a low water content.
30. A composition of any preceding clause wherein the hydroxylase inhibitor is comprised in a pharmaceutical formulation adapted to release the inhibitor in at least the colon.
31. A composition of clause 30 wherein the unit solid further comprises the hydroxylase inhibitor.
32. A pharmaceutical composition of clause 1 being a capsule comprising a population of minibeads which have a diameter of at most 10 mm and which comprise the water-soluble polymer matrix material and a coating on the matrix material, the water-soluble polymer matrix material further including the hydroxylase inhibitor, wherein the hydrophilic surfactant has an HLB value of at least 15, and wherein the coating comprises a controlled-release polymer, optionally wherein the coating is a barrier membrane for extended release of the water-insoluble active ingredient and of the hydroxylase inhibitor and/or is a coating which resists becoming degraded or becoming of increased permeability in the conditions of the GI tract above the colon but which becomes degraded or of increased permeability in the conditions of the colon.
33. A pharmaceutical composition of clause 32 wherein the minibeads further comprise in the polymer matrix part a non-ionic surfactant comprising a poly(oxyethylene) group and the hydrophilic surfactant is an anionic surfactant.
34. A composition of any preceding clause wherein the water-insoluble active ingredient is a macrolide immunosuppressant, and optionally is a cyclosporin, tacrolimus, an ascomycin or sirolimus, and particularly is ciclosporin.
35. A pharmaceutical composition of clause 31 or clause 32 which further includes the specific feature(s) recited in any one or a permitted combination of clauses 2 to 4 or 9 to 29.
36. A composition of any preceding clause wherein the hydroxylase inhibitor is selected from hydralazine, DMOG, FG-4497 and FG4095, and in particular is hydralazine.
37. A composition of any preceding clause which further comprises another active pharmaceutical ingredient.
38. A composition of any preceding clause which comprises a gelatin capsule containing a plurality of minibeads into which the water-soluble polymer matrix material is formed.
39. A product for use in manufacturing a composition of any preceding clause, the product being a water-soluble polymer matrix material formulated as a minibead having a diameter of no more than 10 mm, e.g. of not more than 5 mm, in which matrix material are a water-insoluble active ingredient selected from calcineurin inhibitors, mTor inhibitors and macrolide immunosuppressants; droplets of a water-immiscible liquid in which the water-insoluble active ingredient is soluble, and a hydrophilic surfactant having an HLB value of at least 10.
40. A pharmaceutical composition for oral administration, comprising a water-soluble polymer matrix material in which matrix material are dispersed a water-insoluble active ingredient selected from calcineurin inhibitors, mTor inhibitors and macrolide immunosuppressants; droplets of a water-immiscible liquid in which the water-insoluble active ingredient is soluble, wherein the composition is adapted to release the water-insoluble active ingredient in at least the colon and is for use in treating a disorder of, or at least suspected of being associated with, a leaky intestinal epithelial barrier.
41. A composition of clause 40 wherein the disorder is not inflammatory bowel disease, Crohn's disease, ulcerative colitis, GVHD, or GI-GVHD.
42. A composition of clause 40 or clause 41 wherein the disorder is selected from celiac disease, a rheumatic disorder, rheumatoid arthritis, temporomandibular joint syndrome, type I diabetes, multiple sclerosis, atopic dermatitis, psoriasis, a chronic pain syndrome, fibromyalgia, chronic fatigue syndrome, depressive disorders, affective disorders and attention disorders, gastroenteritis, duodenitis, jejunitis, ileitis, peptic ulcer, Curling's ulcer, appendicitis, colitis, pseudomembraneous colitis, irritable bowel syndrome e.g. irritable bowel syndrome-diarrhea predominant (IBS-D), irritable bowel syndrome-constipation predominant (IBS-C) or irritable bowel syndrome-mixed (IBS-M); diverticulosis, diverticulitis, endometriosis, colorectal carcinoma, adenocarcinoma, and chronic heart failure.
43. A composition of any of clauses 40 to 42 which further comprises, or is for use in combination therapy with, another therapeutically active agent, for example a hydroxylase inhibitor.
44. A composition of any of clauses 40 to 43 which comprises gelatin as the water-soluble polymer.
45. A composition of clause 44 in which gelatin is substantially the only water-soluble polymer.
46. A composition of any of clauses 40 to 45 wherein the water-soluble matrix material is selected from a hydrocolloid, a non-hydrocolloid gum and chitosan and derivatives thereof.
47. A composition of any of clauses 40 to 46 wherein the water-soluble polymer matrix material is in the form of a plurality of minibeads having a diameter of not more than 10 mm, e.g. of not more than 5 mm.
48. A composition of clause 47 wherein the minibeads are monolithic, optionally with layers thereon.
49. A composition of clause 47 or clause 48 wherein the minibeads comprise a controlled-release polymer.
50. A composition of clause 49 wherein the controlled-release polymer is an extended release polymer or an enteric polymer.

51. A composition of clause 47 or clause 48 in which the minibead has a coat which comprises the controlled release polymer and optionally a polymer susceptible to degradation by bacterial enzymes.

52. A composition of clause 49 wherein the controlled-release polymer is ethylcellulose comprised in a coating on the minibead and optionally in association with an emulsification agent, for example ammonium oleate.

53. A composition of clause 52 wherein the ethylcellulose is also in association with a plasticizer, e.g. dibutyl sebacate or medium chain triglycerides.

54. A composition of clause 52 or clause 53 wherein the coating further comprises polymer susceptible of degradation by bacterial enzymes.

55. A composition of clause 54 wherein the polymer susceptible of degradation by bacterial enzymes is water-soluble, preferably pectin.

56. A composition of any of clauses 40 to 55 wherein the water-soluble polymer matrix material further contains a hydrophilic surfactant having an HLB value of at least 10.

57. A composition of clause 56 wherein the hydrophilic surfactant has an HLB value of at least 15, and optionally of at least 18.

58. A composition of clause 56 or clause 57 wherein the hydrophilic surfactant is an anionic surfactant.

59. A composition of clause 58 wherein the anionic surfactant has an HLB value of at least 30.

60. A composition of clause 59, wherein the anionic surfactant comprises or is an alkyl sulfate salt.

61. A composition of clause 60 in which the alkyl sulfate salt is sodium dodecyl sulfate (SDS)

62. A composition of any of clauses 57 to 61 in which the water-soluble polymer matrix material further contains a non-ionic surfactant having an HLB value of at least 10 but less than that of the hydrophilic surfactant.

63. A composition of clause 62 wherein the non-ionic surfactant comprises a poly(oxyethylene) group.

64. A composition of clause 63 wherein the non-ionic surfactant comprises a glycerol polyethylene glycol ricinoleate.

65. A composition of any of clauses 40 to 64 which comprises a liquid lipid and a solvent miscible therewith, in which solvent the water-insoluble active ingredient is soluble.

66. A composition of clause 65 when dependent on any of clauses 62 to 64 in which the ratio of liquid lipid to non-ionic surfactant is in the range 1-4:1 by weight, optionally 1.2-3.0:1 by weight.

67. A composition of clause 65 or clause 66 in which the liquid lipid is a medium chain triglyceride composition, the medium chain triglyceride(s) being one or more triglycerides of at least one fatty acid selected from $C_6$-$C_{12}$ fatty acids.

68. A composition of clause 67 wherein the liquid lipid is a caprylic/capric triglyceride.

69. A composition of any of clauses 65 to 68 in which the oil phase (oil droplets) represents from 10-85% by dry weight of the composition.

70. A composition of any of clauses 65 to 69 in which said solvent is miscible with both the liquid lipid and with water.

71. A composition of any of clauses 69 to 70 in which the solvent is 2-(2-ethoxy)ethanol.

72. A composition of any of clauses 40 to 71 in which the unit solid or minibead has a low water content.

73. A composition of any of clauses 40 to 72 which is for combination therapy with a hydroxylase inhibitor comprised in a pharmaceutical formulation adapted to release the inhibitor in the colon.

74. A composition of clause 73 wherein the water-soluble polymer matrix material further comprises the hydroxylase inhibitor.

75. A pharmaceutical composition of clause 40 being a capsule comprising a population of minibeads which have a diameter of at most 10 mm and which comprise the water-soluble polymer matrix material and a coating on the matrix material, the water-soluble polymer matrix material further including a hydrophilic surfactant which has an HLB value of at least 15, and wherein the coating comprises a controlled-release polymer, optionally wherein the coating is a barrier membrane for extended release of the water-insoluble active ingredient and of the hydroxylase inhibitor and/or is a coating which resists becoming degraded or becoming of increased permeability in the conditions of the GI tract above the colon but which becomes degraded or of increased permeability in the conditions of the colon.

76. A pharmaceutical composition of clause 75 wherein the minibeads further comprise in the polymer matrix part a non-ionic surfactant comprising a poly(oxyethylene) group and the hydrophilic surfactant is an anionic surfactant.

77. A composition of any of clauses 40 to 76 wherein the water-insoluble active ingredient is a macrolide immunosuppressant and optionally is a cyclosporin, tacrolimus, an ascomycin or sirolimus, and particularly is ciclosporin.

78. A pharmaceutical composition of any of clauses 75 to 77 which further includes the specific feature(s) recited in any one or a permitted combination of clauses 2 to 4 or 10 to 28.

79. A method of making the composition of any preceding clause which comprises mixing an oil phase with an aqueous phase comprising a water soluble polymer matrix material to form an emulsion and then causing the emulsion to solidify.

80. A method of clause 79 in which the emulsion is formed into droplets which are then exposed to a solidification medium.

81. An emulsion for use in manufacturing a composition of clause 39, the emulsion comprising oil droplets dispersed in an aqueous phase characterised in that the aqueous phase comprises a water-soluble polymer matrix material and in that the emulsion comprises a water-insoluble active ingredient selected from calcineurin inhibitors, mTor inhibitors, and macrolide immunosuppressants, a hydroxylase inhibitor and a hydrophilic surfactant having an HLB value of at least 10.

82. A pharmaceutical composition for oral administration, obtainable by:

C) mixing together at least the following materials to form an emulsion:
  i) a water-insoluble active ingredient selected from calcineurin inhibitors, mTor inhibitors, and macrolide immunosuppressants;
  ii) an aqueous phase comprising water and a water-soluble polymer material;
  iii) a hydrophobic liquid;
  iv) a hydrophilic surfactant having an HLB value of at least 10;
  v) optionally one or more excipients which are miscible with or soluble in hydrophobic liquid to increase the solubility of the immunosuppressant in the liquid, wherein the water-insoluble active ingredient is soluble in the hydrophobic liquid when it is combined with any said one or more excipients; and D) formulating the emulsion into a pharmaceutical composition comprising a unit solid which comprises the emulsion in a dry state, wherein the composition is adapted to release the active ingredient at least into the colon and the active ingredient is for therapeutic use in combination therapy with a hydroxylase inhibitor.

83. A composition of clause 82 wherein the mixing together comprises forming a clear solution of the active ingredient in the hydrophobic liquid together with any said one or more excipients.

84. A composition of clause 82 or clause 83 wherein the formulating comprises ejecting the emulsion through a single-orifice nozzle, e.g. having a diameter of from 0.5-5 mm, to form drops which are then caused or allowed to fall into a cooling oil and allowed to harden to form minibeads, after which the minibeads are recovered from the cooling oil and dried.

85. A method for administering to a subject a water-insoluble active ingredient selected from calcineurin inhibitors, mTor inhibitors and macrolide immunosuppressants; and a hydroxylase inhibitor, the method comprising:
orally administering a pharmaceutical composition comprising a unit solid which comprises a water-soluble polymer matrix material in which matrix material are dispersed the active ingredient, droplets of water-immiscible liquid in which the active ingredient is soluble and a hydrophilic surfactant having an HLB value of at least 10, the composition being adapted to release the active ingredient in at least the colon; and
simultaneous, sequentially or separately administering a hydroxylase inhibitor to the subject.

86. A method of treating a disorder of, or at least suspected of being associated with, a leaky intestinal epithelial barrier, the method comprising orally administering an effective amount of a pharmaceutical composition comprising a water-soluble polymer matrix material in which are dispersed a water-insoluble active ingredient selected from calcineurin inhibitors, mTor inhibitors and macrolide immunosuppressants, and droplets of water-immiscible liquid in which the active ingredient is soluble, wherein the composition is adapted to release the active ingredient in at least the colon.

EXAMPLES

The following examples use a mouse model of colitis which is described next.

Example 1

Manufacturing of Minibeads 1.1 Hydralazine Beads
Preparation of Gelatin Phase.
Hydralazine (1.50% w/w), SDS (1.50%), D-Sorbitol (2.01%) and gelatin (17.50%) are added to water (77.49%) under constant stirring. The temperature is gradually increased to 60-70° C. to achieve complete dissolution of gelatin.
Preparation of Oil Phase.
Transcutol HP (54.96% w/w), Cremophor EL (30.01%) and Miglyol 810 N (15.04%) are stirred at room temperature until a clear solution is obtained.

Mixing of the Two Phases
Oil Phase and Gelatin Phase are mixed in a 1:9 weight ratio. The resulting solution is stirred at 60-70° C. to achieve a complete homogeneity, then the homogenous solution is ejected through a single orifice to form droplets which fall into a cooling oil medium (Miglyol 810N) at 8-10° C. The nozzle size (diameter) may be from 0.5 to 3.5 mm.
Filtering and Drying of Beads
After approximately 30 minutes, beads are recovered from the cooling oil, centrifuged to eliminate excess oil and then dried at room temperature.
1.2 Hydralazine/Cyclosporin A Combined Beads
1/Preparation of Gelatin Phase (Hydralazine Lower Concentration)
Hydralazine (1.51% w/w), SDS (1.50%), D-Sorbitol (2.01%) and gelatin (17.50%) are added to water (77.48%) under constant stirring. The temperature is gradually increased to 60-70° C. to achieve complete dissolution of gelatin.
2/Preparation of Gelatin Phase (Hydralazine higher concentration)
Hydralazine (2.99% w/w), SDS (1.51%), D-Sorbitol (1.99%) and gelatin (17.46%) are added to water (76.05%) under constant stirring. The temperature is gradually increased to 60-70° C. to achieve complete dissolution of gelatin.
1.3 Cyclosporin A Beads
The cyclosporin beads are prepared following the general procedure set out in section 1.2 immediately above but omitting the hydralazine, and following the general procedure of Example 5.
Preparation of Oil Phase.
Transcutol HP (40.71% w/w), Cremophor EL (22.22%) and Miglyol 810 N (11.13%) are stirred at room temperature until a clear solution is obtained. Cyclosporin is then slowly added (25.92%) and the oil phase is stirred at room temperature until all the Cyclosporin is dissolved
Mixing of the Two Phases
Oil Phase and Gelatin Phase are mixed in a 1:7 weight ratio. The resulting solution is stirred at 60-70° C. to achieve a complete homogeneity, then the homogenous solution is ejected through a single orifice to form droplets which fall into a cooling oil medium (Miglyol 810N) at 8-10° C. The nozzle size (diameter) may be from 0.5 to 3.5 mm.
Filtering and Drying of Beads
After approximately 30 minutes, beads are recovered from the cooling oil solution, centrifuged to eliminate excess oil and then dried at room temperature.
Mouse Model of Colitis
Summary of Procedures
The chosen animal model uses dextran sodium sulphate (DSS) to induce inflammation of the colon, and measures the effectiveness of test formulations on controlling clinical manifestations of disease. Inflammation of the colon is induced using 2.5% DSS in drinking water. The induction of colitis is quantified by determining the disease activity index (DAI). See Clinicopathologic study of dextran sulphate sodium experimental murine colitis, Lab Invest, 69, 238-49. Cooper, H. S., Murthy, S. N., Shah, R. S, and Sedergran, D. J. (1993).

TABLE 1

Scoring of disease activity index.

| Score | Weight loss | Stool consistency | Blood in feces |
|---|---|---|---|
| 0 | None | Normal | None |
| 1 | 1-5% | | |

TABLE 1-continued

| | Scoring of disease activity index. | | |
|---|---|---|---|
| Score | Weight loss | Stool consistency | Blood in feces |
| 2 | 5-10% | Loose | Hemoccult+ |
| 3 | 10-20% | | |
| 4 | >20% | Diarrhoea | Gross bleeding |

The disease activity index is calculated as the sum of scores of weight loss, stool consistency and blood in feces.

Normal stool=formed pellets loose stool=pasty and semiformed stool which do not stick to the anus diarrhoea=liquid stools that stick to the anus Procedures Carried Out DSS Colitis: DSS (Dextran sodium sulfate; 2.5%) is present in the drinking water of the mice for the duration of the experiment. This is a standard model for IBD, The Hydroxylase Inhibitor Dimethyloxalylglycine is Protective in a Murine Model of Colitis *Gastroenterology, Volume* 134, *Issue* 1, January 2008, Pages 156-165.e1. Eoin P. Cummins, Fergal Seeballuck, Stephen J. Keely, Niamh E. Mangan, John J. Callanan, Padraic G. Fallon, Cormac T. Taylor. At the end of the experiment, the mice are euthanized by standard cervical dislocation. To monitor disease progression, disease activity index (DAI) is determined as discussed above.

Administration of Mini-Beads: The Mini-beads are administered using a stainless steel oral gavage needle Two mini-beads are lodged into the free end of the gavage needle and are administered orally to the mice along with 0.1 ml saline using standard 1 ml syringe Example 2

Animal Study 1

Bead Formulations
Cyclosporin formulation (Formulation B)

| Component | % |
|---|---|
| Cyclosporine | 10.48 |
| Mygliol | 4.47 |
| Transcutol | 15.96 |
| Cremophor EL | 8.95 |
| Gelatin | 47.27 |
| SDS | 3.86 |
| D-Sorbitol | 5.44 |
| Surelease (solid content) | 3.50 |
| Pectin | 0.07 |

Cyclosporin/Hydralazine formulation (Formulation A & C)

Formulation A (high level of Hydralazine in the combination)

| Component | % |
|---|---|
| Cyclosporine | 9.30 |
| Hydralazine | 7.54 |
| Transcutol P | 14.61 |
| Miglyol 810N | 4.01 |
| Cremophor EL | 7.97 |
| Gelatin | 43.94 |
| D-Sorbitol | 5.01 |
| SDS | 3.79 |

-continued

| Component | % |
|---|---|
| Surelease (solid content) | 3.77 |
| Pectin | 0.08 |

Formulation C (low level of Hydralazine in the combination)

| Component | % |
|---|---|
| Cyclosporine | 9.69 |
| Hydralazine | 3.95 |
| Transcutol P | 15.21 |
| Miglyol 810N | 4.16 |
| Cremophor EL | 8.31 |
| Gelatin | 45.84 |
| D-Sorbitol | 5.25 |
| SDS | 3.93 |
| Surelease (solid content) | 3.59 |
| Pectin | 0.07 |

The following dosages were administered:

Formulation B: ~0.629 mg CyA per 2 bead dose

Formulation A: ~0.651 mg CyA and 0.528 mg HyA per 2 bead dose

Formulation C: ~0.678 mg CyA and 0.277 mg HyA per 2 bead dose.

In the "low HyA level" minibeads of formulation C, the weight ratio of HyA:CyA was about 0.4:1. In the "high HyA level" minibeads of formulation A, the weight ratio of HyA:CyA was about 0.8:1.

In the Dextran Sulphate Sodium (DSS) model of colitis, mice are exposed to DSS in their drinking water which induces a loss of intestinal barrier function with subsequent mucosal inflammation. Weight loss and disease activity index are used as a measure of disease progression.

Figure 2:
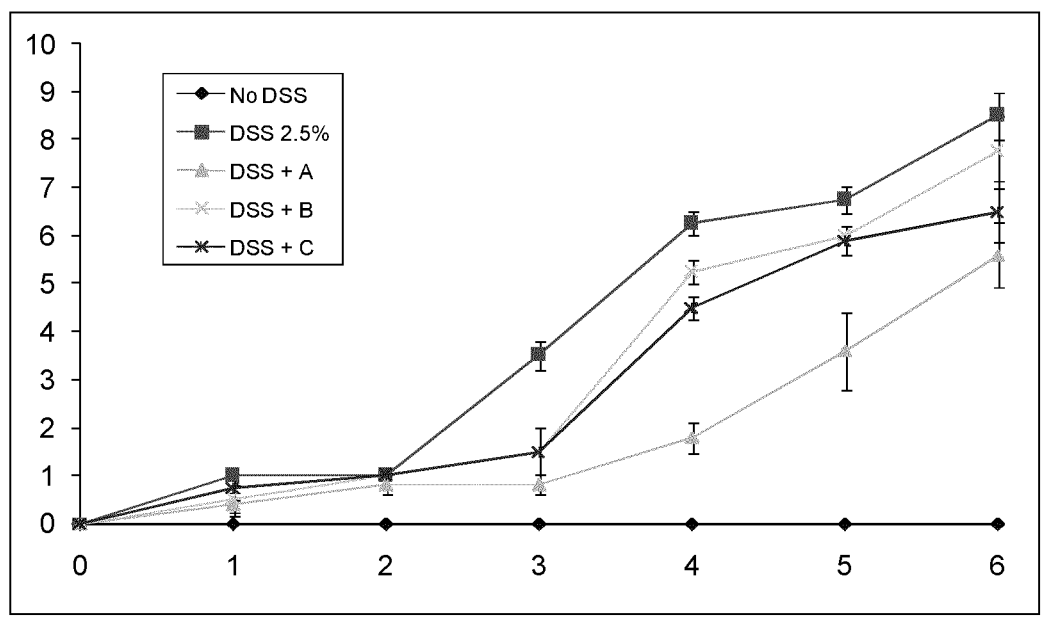
FIG. 2 is a Disease Activity Index (DAI) graph showing the effect of compositions of the invention (see Example 2)

The results are shown in FIGS. 1 and 2.

The weight loss and DAI suggest that:

Formulation A (high level of Hydralazine) shows the highest degree of protection in DSS induced colitis.

Formulation B is protective at the early stage until day 4 and then shows a downward trend.

Bead C is not protective at the early stage of induction of colitis.

Histology

Figure 3:
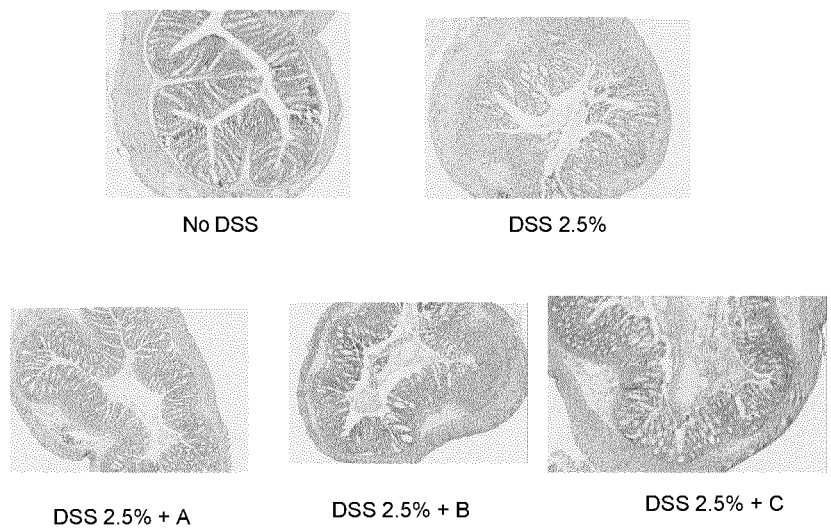
FIG. 3 is a set of histology slides showing the effect of compositions of the invention (see Example 2)

Colon sections of euthanized mice are stained and examined microscopically. Slides of the sections are shown in FIG. 3. The histology slides also show that Formulation A has the highest degree of protection in DSS induced colitis.

Example 3

Animal Study 2

Bead Formulations
Formulation A (3.8% wt. g Hydralazine beads)

| Component | % w/w |
|---|---|
| Hydralazine | 4.31 |
| Transcutol P | 17.44 |
| Miglyol 810N | 4.77 |
| Cremophor EL | 9.52 |
| Gelatin | 50.23 |
| D-Sorbitol | 5.76 |
| SDS | 4.31 |

-continued

| Component | % w/w |
|---|---|
| Surelease (Solid Content) | 3.59 |
| Pectin | 0.07 |

Formulation B (3.8% wt. g hydralazine/cyclosporin A beads)

| Component | % w/w |
|---|---|
| Cyclosporine | 9.69 |
| Hydralazine | 3.95 |
| Transcutol P | 15.21 |
| Miglyol 810N | 4.16 |
| Cremophor EL | 8.31 |
| Gelatin | 45.84 |
| D-Sorbitol | 5.25 |
| SDS | 3.93 |
| Surelease (Solid Content) | 3.59 |

Formulation C (Hydralazine uncoated beads)

| Component | % w/w |
|---|---|
| Hydralazine | 4.47 |
| Transcutol P | 18.10 |
| Miglyol 810N | 4.95 |
| Cremophor EL | 9.88 |
| Gelatin | 52.14 |
| D-Sorbitol | 5.97 |
| SDS | 4.47 |

Formulation D (10% wt. g HyA/CyA beads)

| Component | % w/w |
|---|---|
| Cyclosporine | 9.11 |
| Hydralazine | 3.71 |
| Transcutol P | 14.31 |
| Miglyol 810N | 3.91 |
| Cremophor EL | 7.81 |
| Gelatin | 43.11 |
| D-Sorbitol | 4.94 |
| SDS | 3.69 |
| Surelease (Solid Content) | 9.22 |
| Pectin | 0.19 |

Formulation E (8.7% wt. g Hydralazine beads)

| Component | % w/w |
|---|---|
| Hydralazine | 4.11 |
| Transcutol P | 16.65 |
| Miglyol 810N | 4.56 |
| Cremophor EL | 9.09 |
| Gelatin | 47.97 |
| D-Sorbitol | 5.50 |
| SDS | 4.12 |
| Surelease (Solid Content) | 7.84 |
| Pectin | 0.16 |

Formulation F (Uncoated HyA/CyA beads)

| Component | % w/w |
|---|---|
| Cyclosporine | 10.06 |
| Hydralazine | 4.10 |

-continued

| Component | % w/w |
|---|---|
| Transcutol P | 15.79 |
| Miglyol 810N | 4.32 |
| Cremophor EL | 8.62 |
| Gelatin | 47.58 |
| D-Sorbitol | 5.45 |
| SDS | 4.08 |

The following dosages were administered:
Formulation A: ~0.259 mg HyA per 2 bead dose
Formulation B: ~0.678 mg CyA and 0.277 mg HyA per 2 bead dose
Formulation C: ~0.268 mg HyA per 2 bead dose
Formulation D: ~0.638 mg CyA and 0.260 mg HyA per 2 bead dose
Formulation E: ~0.247 mg HyA per 2 bead dose
Formulation F: ~0.704 mg CyA and 0.287 mg HyA per 2 bead dose.

Figure 4:
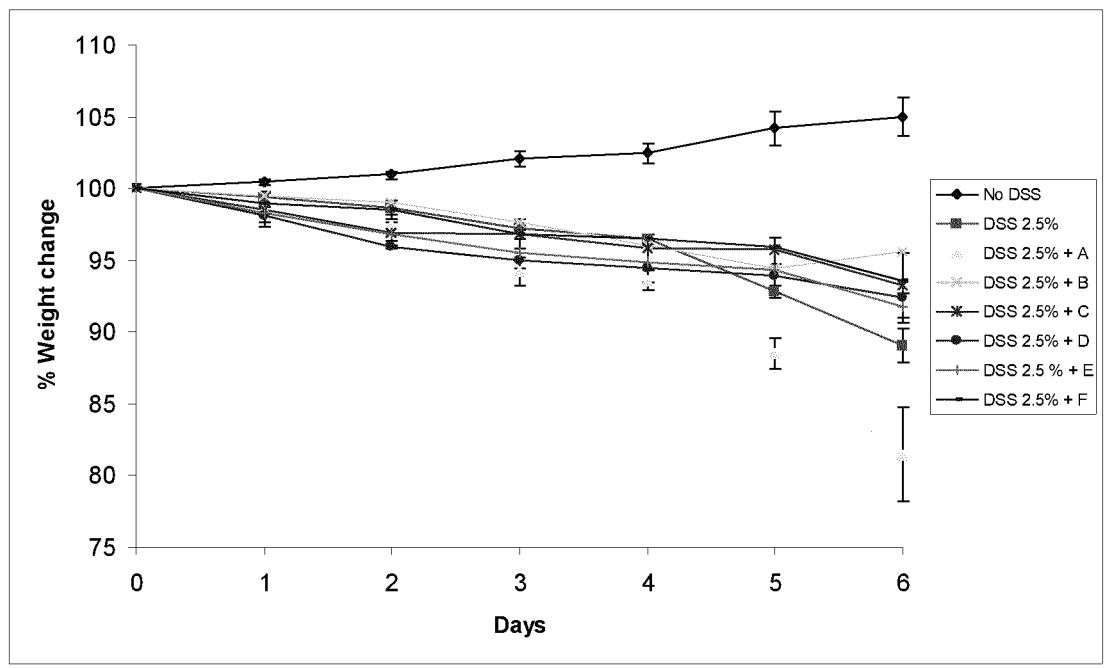
FIG. 4 is a second plot of weight loss change showing the effect of compositions of the invention (see Example 3)
Figure 5:
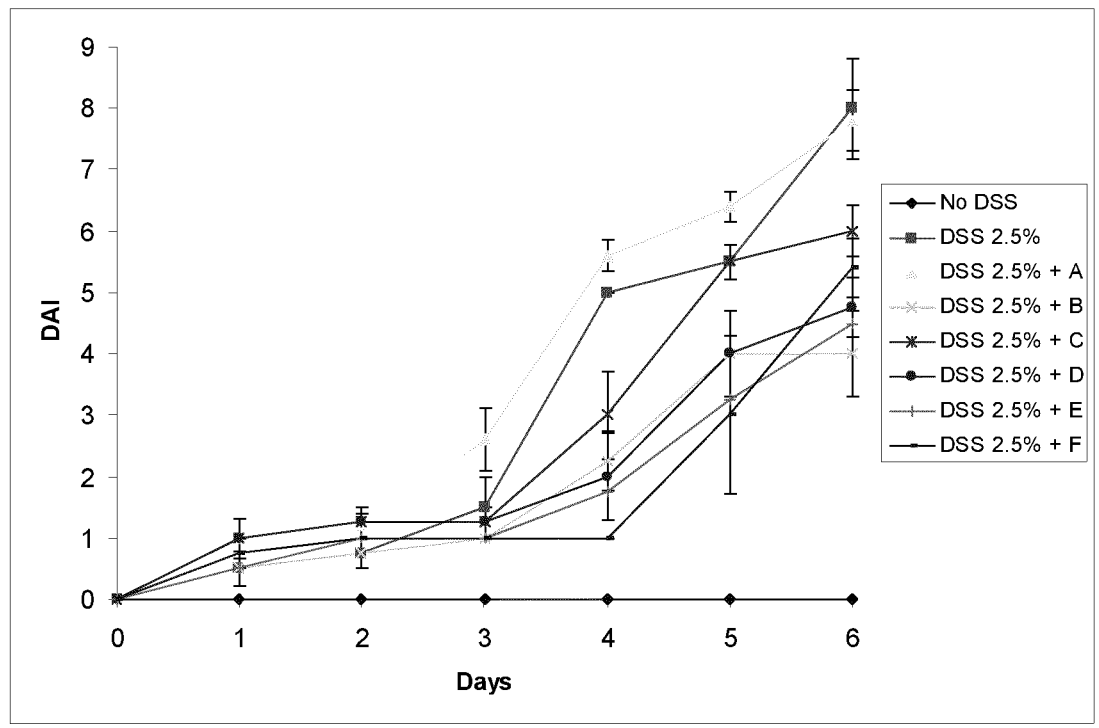
FIG. 5 is a second Disease Activity Index (DAI) graph showing the effect of compositions of the invention (see Example 3)

The weight loss change and disease activity index results are shown in FIGS. 4 and 5.

From the weight loss data and DAI bead B (3.8% wt. g HyA/CyA beads) has a better protective efficacy followed by D and E.

Figure 6:
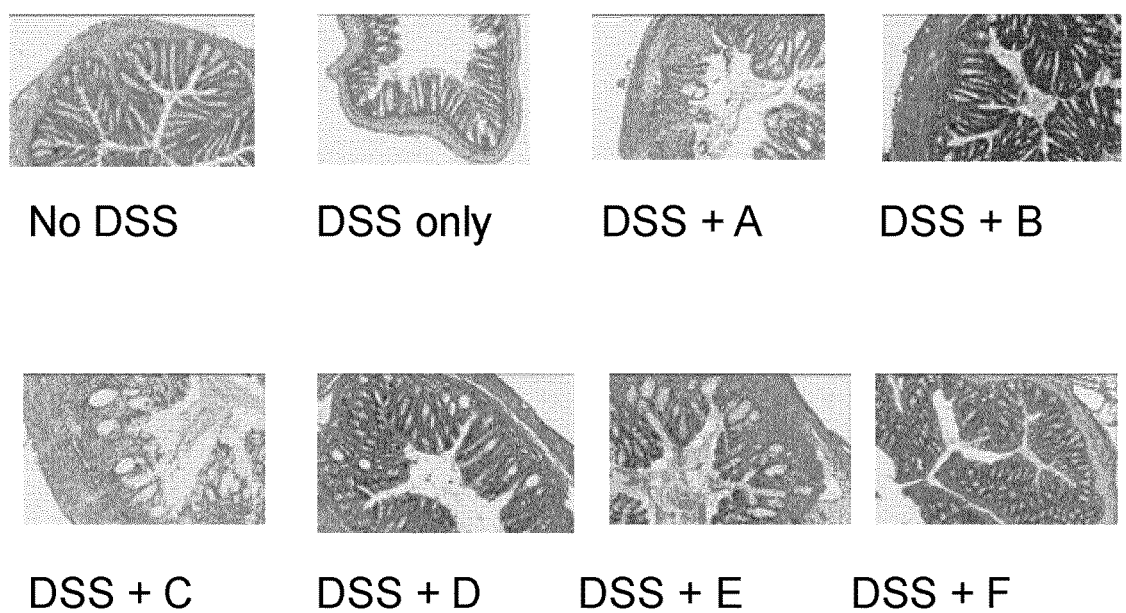
FIG. 6 is a second set of histology slides showing the effect of compositions of the invention (see Example 3)

Colon sections of euthanized mice are stained and examined microscopically. Slides of the sections are shown in FIG. 6. The histology slides show that Formulations B (3.8% wt. g. HyD/CyA beads) has the highest degree of protection in DSS induced colitis followed by D and E&F.

Comparative Example

Monotherapy with Hydralazine

Figure 7:
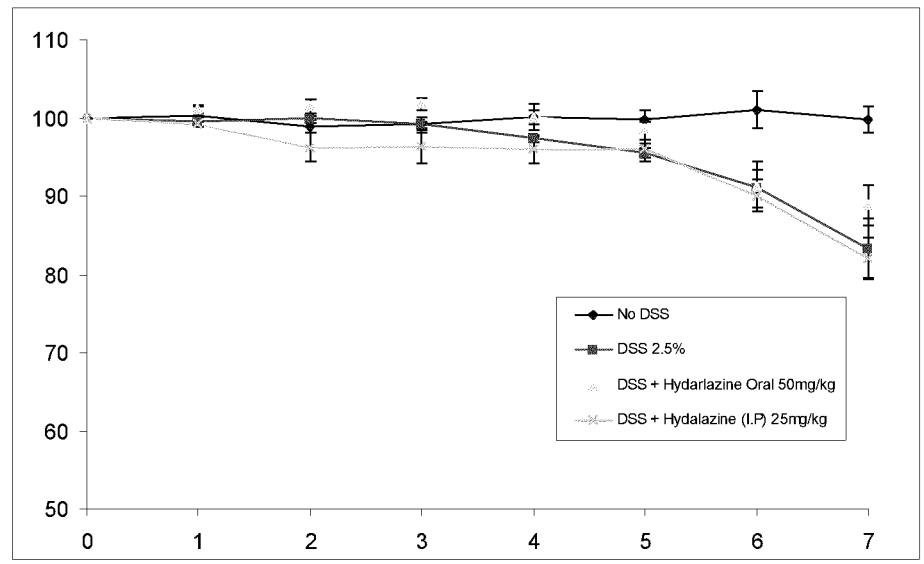
FIG. 7 is weight loss change graph relating to hydralazine administered orally or i.p. (see the comparative example)
Figure 8:
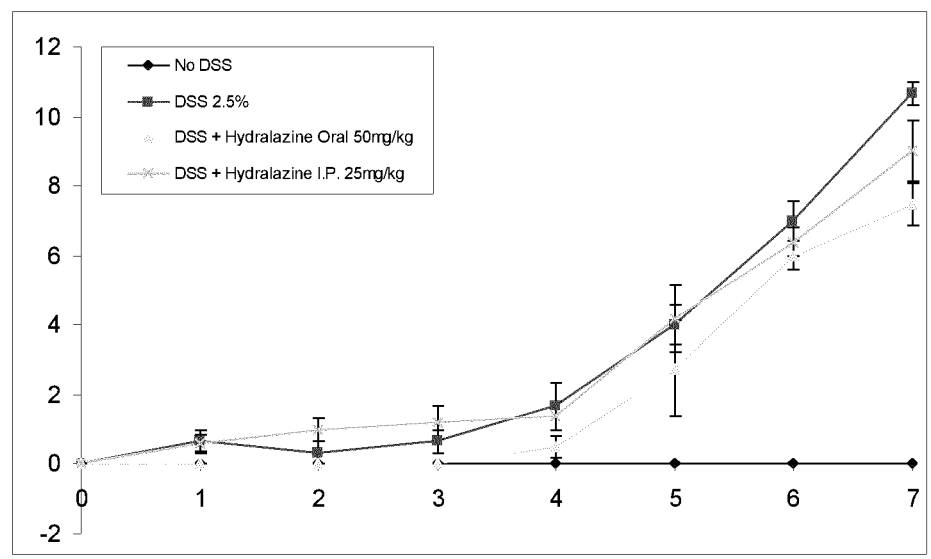
FIG. 8 is a Disease Activity Index (DAI) graph relating to hydralazine administered orally or i.p. (see the comparative example)

Hydralazine is administered to mice orally or i.p in the DSS colitis model and the results (weight change and DAD are shown in FIGS. 7 and 8.

The administration of Hydralazine API (oral and i.p. administration) did not lead to any improvement both in terms of DAI and weight loss in DSS model of colitis.

Example 4

Caco-2 Monolayer Tests

Figure 9:
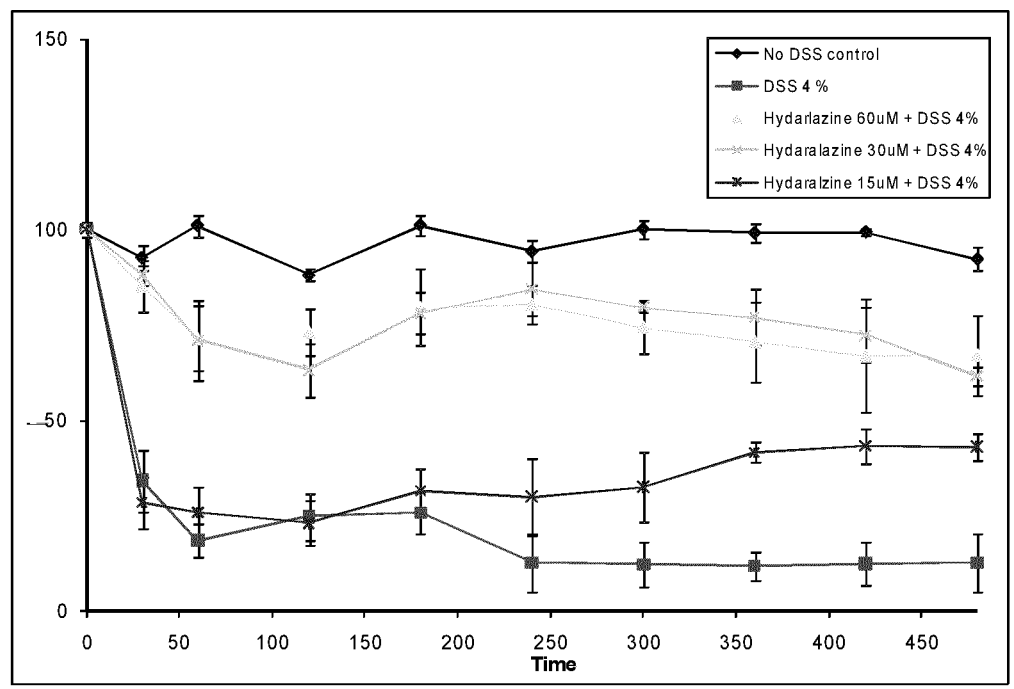
FIG. 9 is a graph of Transepithelial Electrical Resistance (TEER) showing the effects of hydralazine at different concentrations in aqueous solutions with DSS (dextran sodium sulphate) (see Example 4)

Transepithelial electrical resistance (TEER) is measured in 5 animal groups (see legend to FIG. 9) and the results are shown in FIG. 9.

As DSS is a chemical irritant which causes the disruption of the Caco-2 monolayer, the TEER values are lowest in the case of DSS 4%. TEER values for the DSS 4% alone receded to less that 20% indicating complete disintegration of the mono-layer.

Hydralazine 30 uM and 60 uM shows significant protection to barrier function to Caco-2 cells grown on permeable inserts in DSS induced in-vitro model of colitis.

Figure 10:
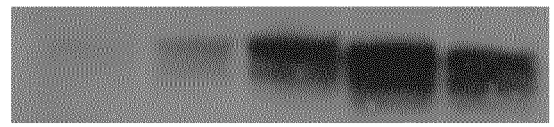
FIG. 10 comprises a photograph of a gel illustrating changes in HIF-1α expression using hydralazine in Caco-2 cells (see Example 4)
Figure 10:
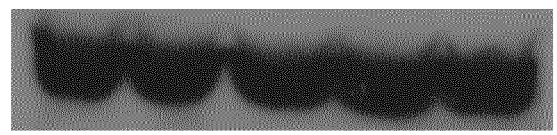
Figure 11:
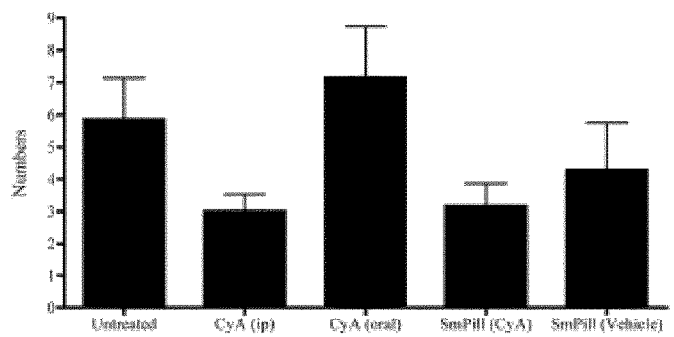
FIG. 11 is a bar chart showing the number of adenocarcinomas in colons of IL-10$^{-/-}$ mice administered various compositions and wherein "SmPill" designates a formulation of the invention and "CyA" means Cyclosporin A (also known as ciclosporin)

Also monitored are changes in HIF-1α expression in Caco-2 cells with dosage of different hydralazine concentrations. The results are shown in FIG. 10.

Example 5

Comparative Efficacy of Treatment with Cyclosporin A (Ciclosporin) Via Oral Minicapsules or i.p, Administration of the Same Dose of Cyclosporin A in a Spontaneous Mouse Model of Colitis In this example, the terms "Cyclosporin A" and "CyA" both refer to the drug whose international non-proprietary name is "ciclosporin". Also in this example, the term "SmPill" refers to a minicapsule formulation of the disclosure.

Manufacturing Materials

The materials used to make coated bead formulations are as follows:

| Ingredient | % Wt/Wt | Function | Chemical Composition |
|---|---|---|---|
| Ciclosporin | 10.59 | Active Ingredient | Cyclic polypeptide |
| Transcutol P | 16.07 | Solubiliser | 2-(2-ethoxyethoxy)ethanol |
| Cremophor EL | 8.96 | Non-ionic surfactant | Macrogolglycerol ricinoleate (polyethoxylated castor oil) |
| Miglyol 810N | 4.54 | Oil | Triglycerides of fractionated $C_8$ and $C_{10}$ plant fatty acids |
| D-Sorbitol | 5.47 | Plasticiser | A sugar alcohol |
| Sodium Dodecyl Sulphate | 3.84 | Anionic surfactant | Sodium Dodecyl Sulphate |
| Gelatin Type A Porcine | 47.61 | Bead shell-forming agent | Protein |
| COATING MATERIALS | | | |
| Surelease ® | 2.85 | Rate Controlling Release Polymer | Ethylcellulose |
| Pectin | 0.06 | Pore former | Polysaccharide |

Manufacturing Method

The method generally follows the procedure of Example 1 and may be summarised as follows:
1. Sodium dodecyl sulphate and D-sorbitol are mixed with purified water. Gelatin is then added to this solution and gentle heat applied (to increase the temperature to 60-70° C.) until the gelatin has dissolved. (Aqueous phase)
2. Transcutol P, Cremophor EL and Miglyol 810 are added together and mixed. Ciclosporin is then added and mixed until it a clear solution is obtained. (Oil phase)
3. The aqueous and oil phases are mixed to form an emulsion as described in Example 1.
4. The emulsion is then fed (via temperature controlled tubing) from the emulsion vessel through a vibrating single orifice nozzle. The nozzle size (diameter) is 3.4 mm.
5. Seamless beads are formed as the solution flows through the vibrating nozzle into a chamber of constantly flowing medium chain triglyceride (Miglyol 810) as a cooling oil. The cooling oil is at temperature of 8-10° C.
6. The minicapsules are then removed from the cooling oil and placed in a centrifuge to remove the excess oil.
7. Following centrifugation, Drying is initiated with a set refrigeration temperature. When the beads are rotating freely within the drum, they are considered to be dried.
8. The ethyl acetate is used to wash the minicapsules (remove any excess oil etc.). The beads are dried for a further 24 h.
9. The dried beads are then sieved to remove oversize and undersize beads. The beads after sieving are sized 1 mm-2 mm.
10. Pectin is added to purified water in a stainless steel vessel and mixed to obtain a solution. Once the pectin is fully dissolved, Surelease® is slowly added to the vessel whilst mixing is continued.
11. The beads are coated until a weight gain of 3% has been reached.

1. Experimental Methods
1.1 IL-10−/− Colitis Model.

Mice with a disruption in the Interleukin-10 gene (IL-10−/−) spontaneously develop chronic colitis and colorectal adenocarcinomas, with the age of onset and the severity of the disease in IL-10−/− mice being dependent on background mouse strain and the conditions that the animals are housed in. The progressive chronic enterocolitis in IL-10−/− mice can be partially ameliorated by treatment of young mice with exogenous IL-10, but once disease is established in adult animals the disease is not reversible by cytokine treatment with 100% of mice affected. IL-10−/− mice are routinely used as a model to test the efficacy of new drugs or treatment strategies for inflammatory bowel disease in humans for example, screening the efficacy of probiotics.

In this project, 5-6 week-old female IL-10−/− mice, on a C57BL/6J strain background, were purchased from Jackson Laboratories (USA). Mice were kept in individually ventilated and filtered cages under positive pressure. Mice were fed an irradiated diet and housed on irradiated bedding. Food and water were supplied ad libitum. Sentinel mice were screened to ensure SPF status. All animal experiments were performed in compliance with Irish Department of Health and Children regulations and were approved by an ethical review board.

The comparative efficacy of conventional delivery of a daily dose of Cyclosporin A, i.p. or orally, versus delivery of the same dose via incorporation into a minicapsule was tested in IL-10−/− mice on a C57BL/6J background. Drug treatments were administered to mice during the chronic progression from mild to moderate colitis. Drugs were delivered daily (a CyA daily dose of 0.75 mg), see Table 1, to 7-8 week-old IL-10−/− mice, coincident with the on-set of mild disease, with treatment continued for a further 6 weeks when overt moderate colitis, i.e. no mortalities but clinical sign of colitis, develop. Mice were checked daily for rectal prolapse and/or bleeding (blood in faeces) and mice were weighed weekly.

1.2 Cyclosporin A (CyA) Treatment Regime.

All drugs were provided by Sigmoid Pharma (Table 1). All compounds and experimental groups were randomly alphabetically labeled. Throughout experiments all data recording and analyses were performed in a blind manner. The codes on boxes/groups were not broken until after the data was collected.

1.3 Disease Activity Index (DAI).

To quantify the severity of colitis, a disease activity index (DAI) was determined based on previous studies of colitis in IL-10−/− mice (Danese, S., M. et al., 2007 Gut 56:855-862). DAI was calculated for individual mice weekly. The DAI was based on a score of 1 for each of ruffled fur, occult blood and soft stools. Animals with diarrhea or rectal prolapse that required humane killing of the animal had an additional score of 2 added. A score was given for each parameter, with the sum of the scores used as the DAI. The maximum potential score was 5.

41.4 Serum Amyloid A Analysis.

In Ulcerative colitis and Crohn's disease patients the levels of Serum Amyloid A (SAA) are correlative with clinical disease and histology scoring of colon inflammation (Niederau, C., F. Backmerhoff, and B. Schumacher. 1997. *Hepatogastroenterology* 44:90-107). In IL-10−/− mice SAA levels are also predictors of disease severity (Wei, X. et al.

2008. *Clin Immunol* 129:211-218). Blood from mice was recovered at termination and serum isolated. Sera from mice were tested by ELISA (Life Diagnostics Ltd) for SAA.

1.5 Spleen Cytokine Analysis.

To address effects of different methods of administration of CyA on systemic cell immunity, cytokine production from spleen cells was examined after ex vivo restimulation. Spleens were removed from 4 mice per group, 1-4 by code number, at termination. Single cell suspensions were cultured in vitro in media-alone or nonspecifically stimulated with 2.5 ng/ml Phorbal 12-myristate 13-acetate (PMA, Sigma, UK) and 250 ng/ml ionomycin (Sigma, UK). Tumour necrosis factor (TNF)-α, Interleukin (IL)-1β and IL-17 levels in supernatants were detected by ELISA using commercial kits (R&D Systems).

1.6 Colon Cytokines and Myeloperoxidase Detection.

In order to assess inflammatory immune responses at the site of disease, colons were removed from mice and after removal of tissue for histology, immediately snap frozen and stored at −80° C. Colons were homogenized and processed as described (Smith, P. et al. 2007. *J Immunol* 178:4557-4566).

Colon extracts were analysed for TNF-α, IL-1β and IL-17, as representative proinflammatory cytokines, using ELISA as described above. Myeloperoxidase (MPO) enzymatic activity in the colons was analysed as a marker of inflammation. Cytokines and MPO are expressed as pg, or units per mg colon protein, respectively.

1.7 Histopathological Analysis of Colons.

When mice were euthanised, a ~1 cm piece of the proximal colon was removed and fixed in 10% formaldehyde-saline. Sections were prepared and stained with haematoxylin and eosin, as described (Smith, P. et al. 2007. *J Immunol* 178:4557-4566). All histological scoring was performed in a blinded fashion by two observers independently. Colon sections from mice were graded using a histological index ranging from 0 to 4, based on a scoring system used in previous studies on IL-10−/− mice (McCarthy, J. et al. 2003. *Gut* 52:975-980). This index was based on the degree of epithelial layer erosion, goblet cell depletion, and inflammatory cell infiltrate (0=normal; 1=minimal evidence of inflammatory infiltrate; 2=significant evidence of inflammatory infiltrate (cryptitis, crypt abscesses); 3=significant evidence of inflammatory infiltrate with goblet cell depletion; 4=significant evidence of inflammatory infiltrate with erosion of the mucosa). The maximum possible score was 4.

1.8 Statistical Analysis.

Power calculations on data from our previous studies in IL-10−/− mice (3), determined a sample size of at least 7 will detect significant difference (P<0.05) between groups in the 6-week regime used. ANOVA and Tukey-Kramer Multiple Comparisons Test determined statistical differences between multiple groups. 2.

Results.

Testing Comparative Activity of Different Methods of Delivery of CyA in the IL-10−/− Mouse Model of Spontaneous Colitis.

Female IL-10−/− mice, all 5-6 weeks of age, were randomized into groups and housed for two weeks before drug treatment started. Groups of mice were treated as described in Table 1. Drugs were administered and mice monitored daily. Animals were weighed weekly.

TABLE 1

Experimental compounds administered. Cages of mice were labeled by random coding, with the researcher blinded to the code throughout the experiment. Mice were treated as indicated daily.

| | |
|---|---|
| SmPill ™ with CyA (0.25 mg CyA/bead) | ORAL<br>3 beads daily in 0.2 mls of PBS<br>0.75 mg CyA/daily |
| SmPill ™ without CyA (Vehicle) | ORAL<br>3 beads daily in 0.2 ml of PBS |
| CyA<br>Sandimmun ® (50 mg/ml solution) | INTRAPERITONEAL<br>0.2 ml per day<br>0.75 mg CyA/daily |
| CyA<br>Neoral ® (100 mg/ml oral solution) | ORAL<br>0.1 mls per day<br>0.75 mg CyA/daily |
| Untreated | — |

There was death of one mouse, in SmPll (CyA) group on day 21 of the experiment (This mouse was euthanized following tracheal damage as a result of drugadministration via gavage). There were no other mortalities during the course of the experiment. No adverse effects were seen in any animals.

Figure 12:
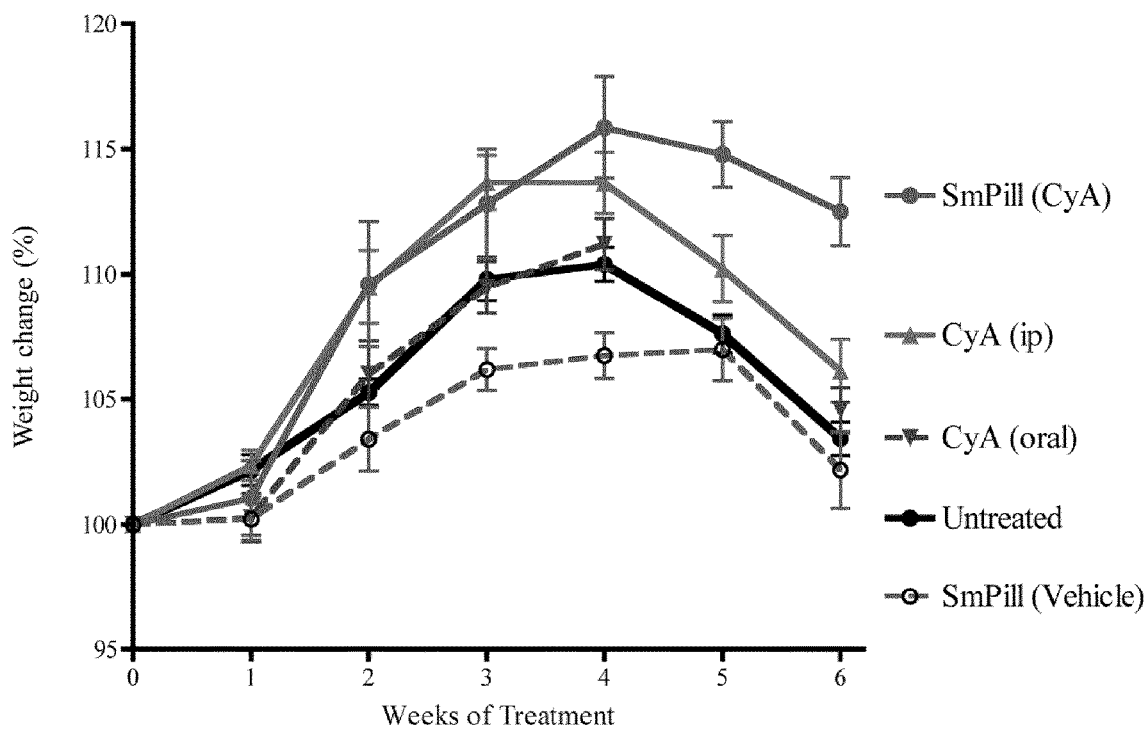
FIG. 12. is a graph showing the change in weight of IL-10-/- mice with different treatment regimes over 6 weeks (see Example 5)
Figure 13:
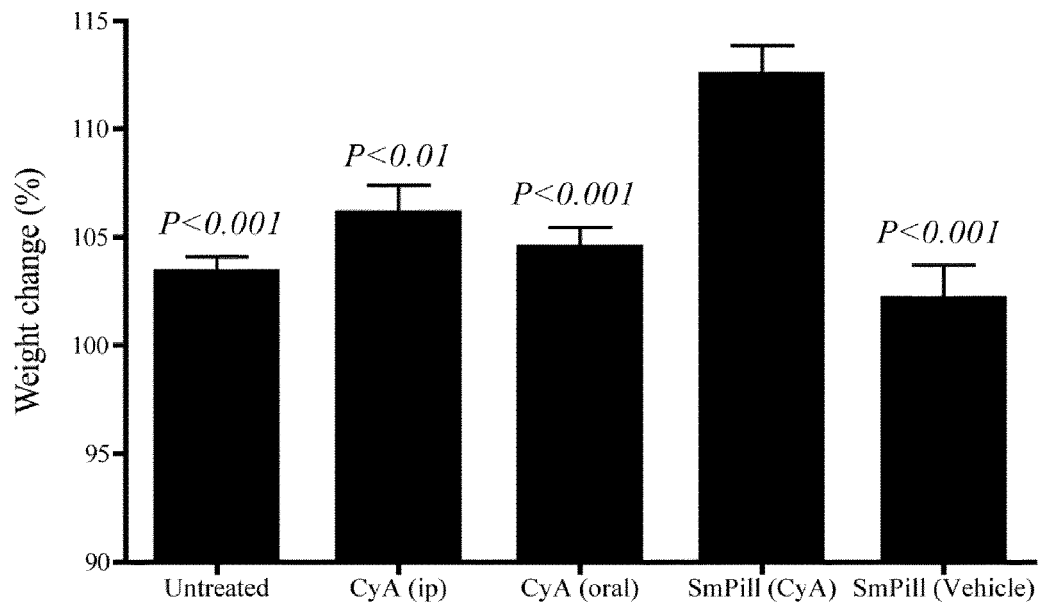
FIG. 13 is a bar chart showing the weight change of IL-10-/- mice with different treatment regimes on day of termination (day 42) as percentage weight change relative to starting weight (at week 0 of experiment) (see Example 5)

In all groups there was a progressive increase in weight gain of mice until the 4th-5th week of the treatment regime; thereafter all groups ceased to gain weight, or had weight loss (FIG. 12). At termination, week 6, a trend of relatively less weight loss in SmPill (CyA)-treated mice (FIG. 12) was evident, with these mice being significantly heavier (P<0.01-0.001) than all other groups (FIG. 13).

Figure 14:
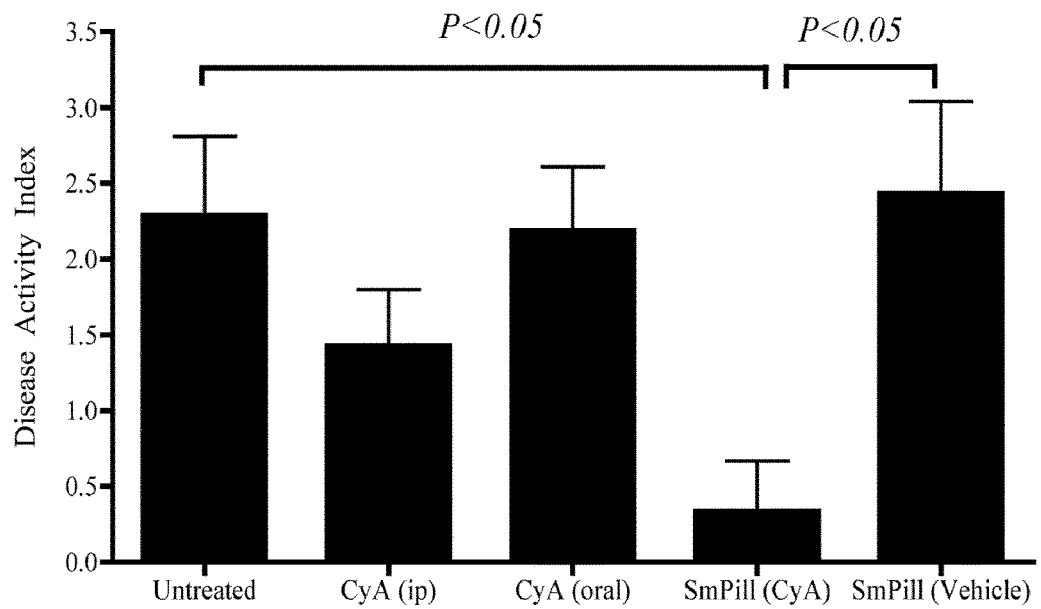
FIG. 14 is a bar chart showing the Disease Activity Index (DAI) in IL-10-/- mice with different treatment regimes on day of termination (see Example 5)

No animals developed overt morbidity, rectal prolapse or frank diarrhea during the 6-week treatment regime. However, from day 37 mice in the untreated and SmPill (Vehicle) groups had evidence of blood in their faeces. Based on DAI scoring on day 42 when mice were culled, the SmPill (CyA) had the lowest DAI scores (FIG. 14), relative to other groups, with these animals predominately having soft stools or occult faecal blood. SmPill (CyA)-treated mice had significantly (P<0.05) lower scores relative to untreated or SmPill (Vehicle) groups, with non-significantly lower DAI values then CyA (i.p.) or CyA (Oral) groups (FIG. 14).

Figure 15:
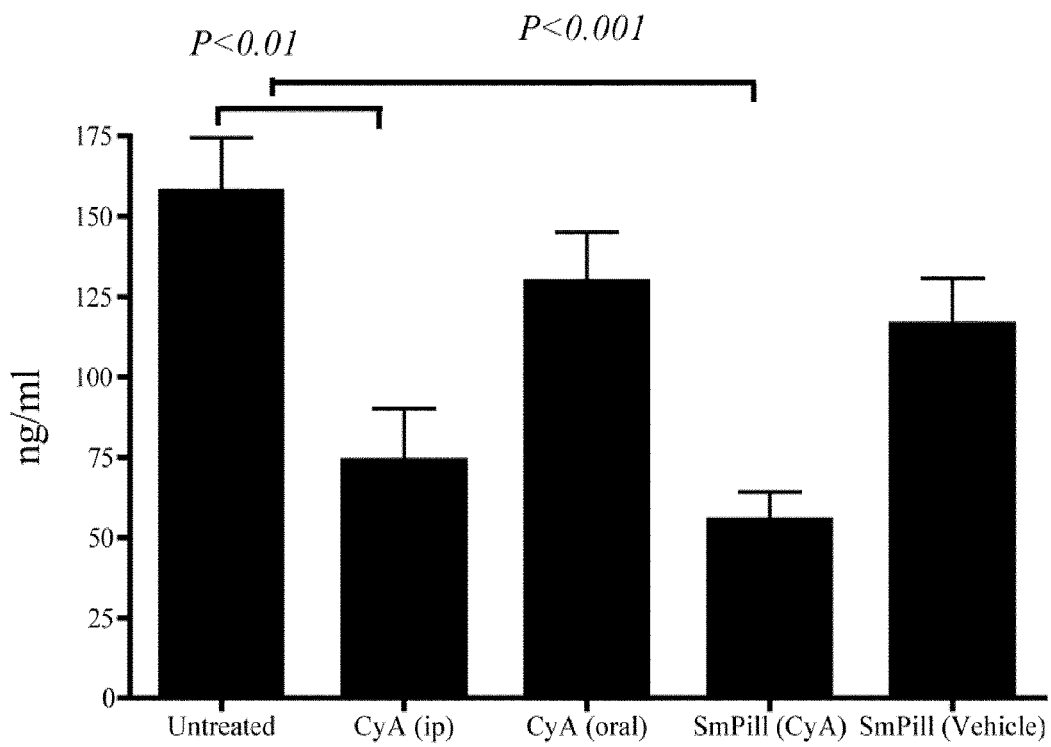
FIG. 15 is a bar chart showing the level of Serum Amyloid A (SAA) in IL-10-/- mice with different treatment regimes at the day of termination (see Example 5)

Levels of SAA were analysed in serum isolated at termination on day 42. The untreated group of mice had the highest SAA levels, with the lowest in SmPill (CyA)-treated mice and then CyA (i.p.)-treated mice (FIG. 15). The lower relative levels in CyA (i.p) and SmPill (CyA) groups were significant (P<0.01 and P<0.001, respectively) relative to untreated mice, but not other groups (FIG. 15).

Figure 16:
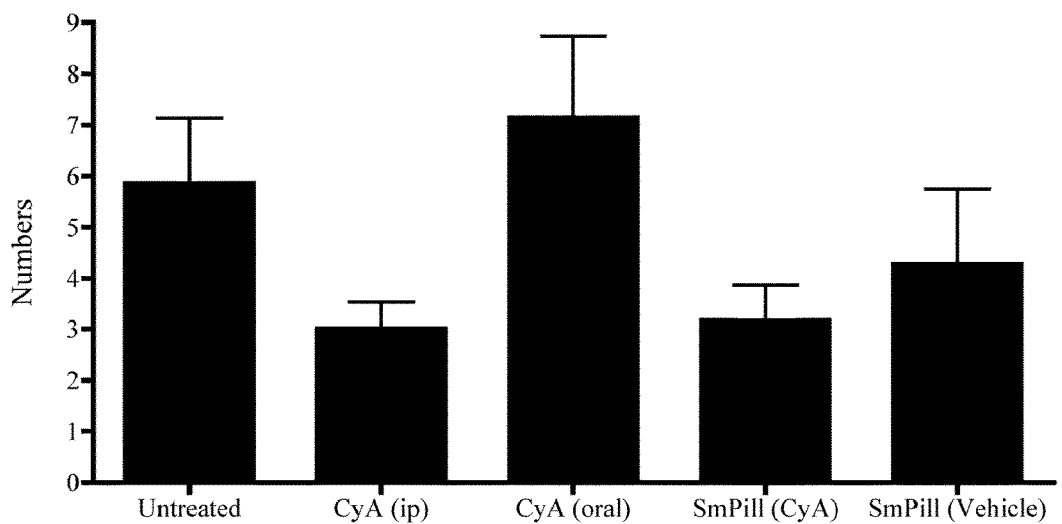
FIG. 16 is a bar chart showing the numbers of adenocarcinomas in colons of IL-10-/- mice with different treatment regimes at the day of termination (see Example 5)

As IL-10−/− mice develop colorectal adenocarcinomas the numbers of these were recorded at autopsy. While there were differences between groups in the mean number of adenocarcinomas detected in the colons, with CyA (i.p.) and SmPill (CyA) groups having relatively less, the difference was not statistically significant (FIG. 16). It was also noted that the adenocarcinomas seen in both these groups were smaller relative to those observed in the other three groups of mice; however, this was not formally quantified.

Figure 17:
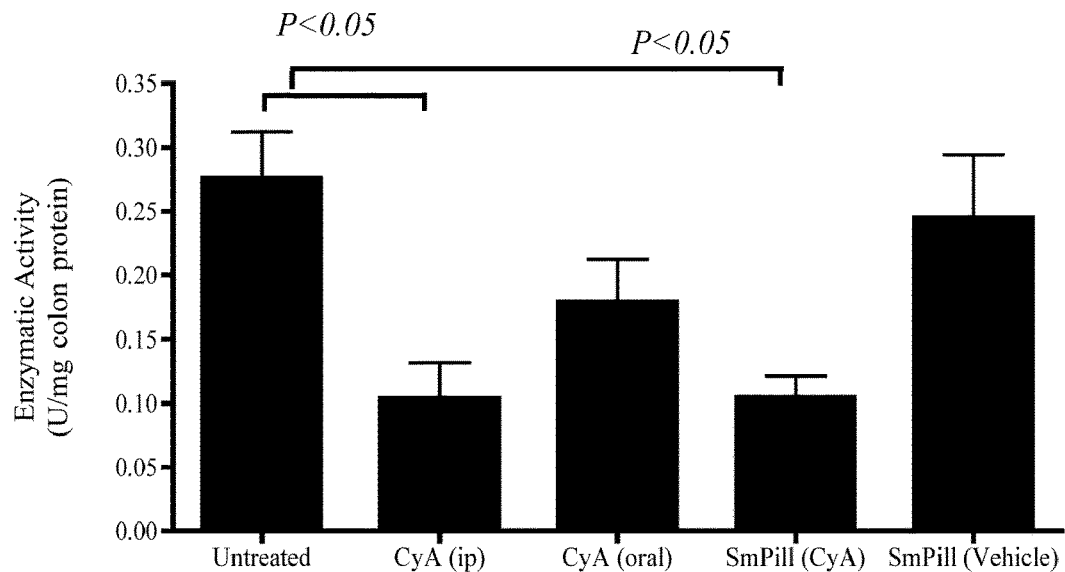
FIG. 17 is a bar chart showing myeloperoxidase (MPO) enzymatic activity in the colons of IL-10-/- mice with different treatment regimes (see Example 5)

At autopsy the entire colon, excluding tissue removed for histology, was removed and processed to quantify MPO enzymatic activity, as a marker of inflammation. Additionally, the levels of the pro-inflammatory cytokines, IL-1β, IL-17 and TNF-α were also quantified. The colons of the untreated and SmPill (Vehicle) mice had the highest MPO enzymatic activity, with non-significantly lower enzymatic activity in CyA (Oral)-treated mice (FIG. 17). There was statistically lower MPO activity in both CyA (i.p.) and SmPill (CyA) groups relative to untreated mice (P<0.05), but not with the other groups.

Figure 18A:
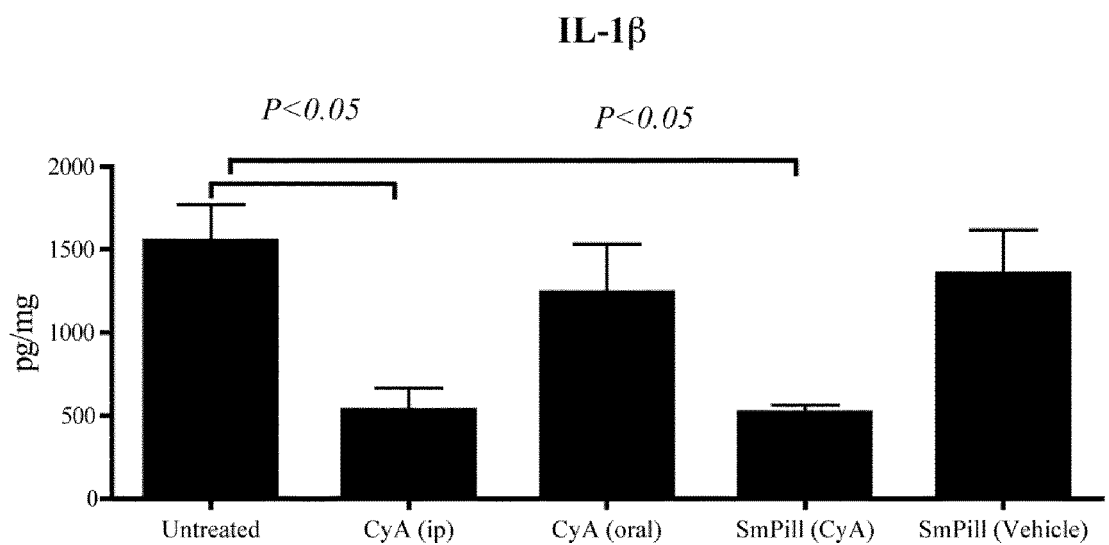
FIGS. 18A, 18B and 18C are bar charts showing the colon levels of cytokines IL-1β, TNF-α and IL-17 in IL-10-/- mice with different treatment regimes (see Example 5)
Figure 18B:
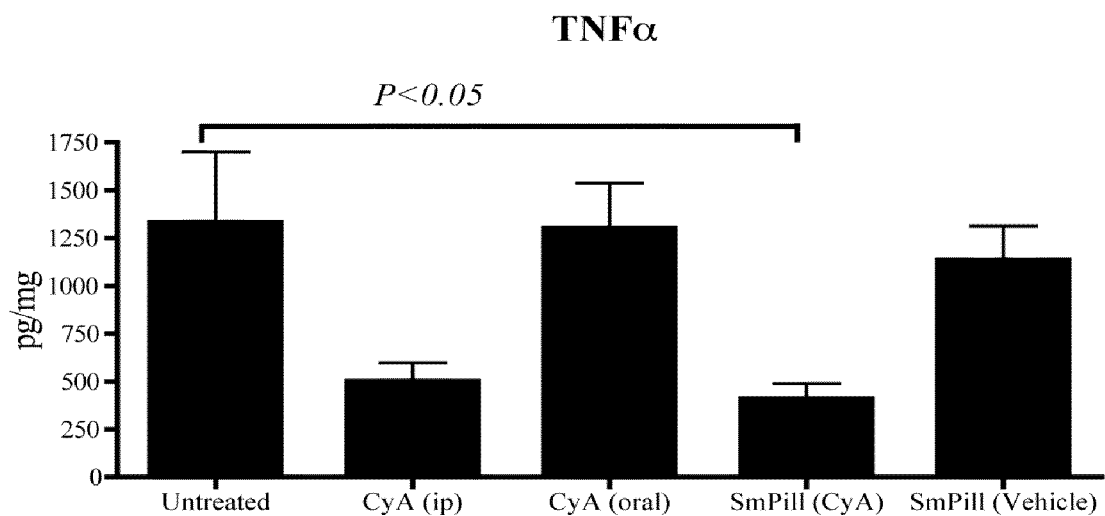
Figure 18C:
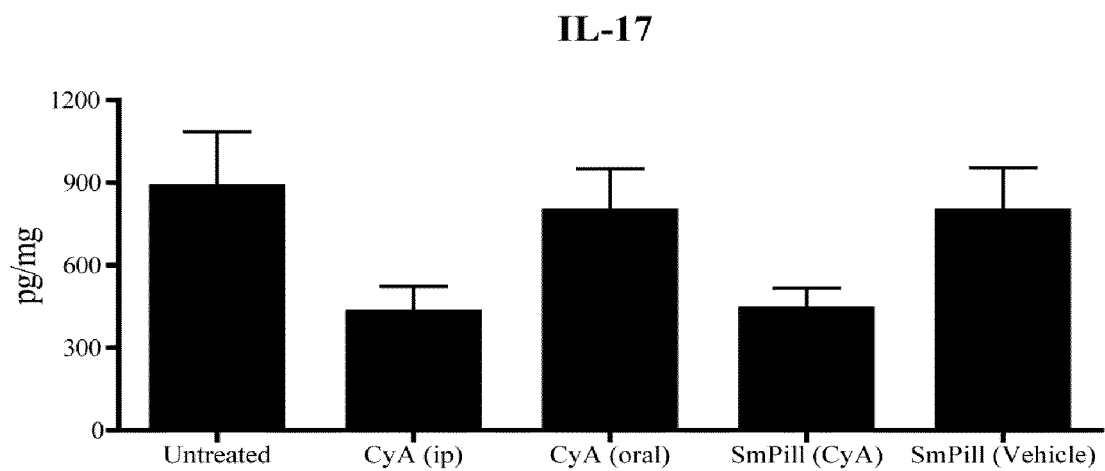

Consistent with reduced MPO levels in the colons of mice treated with CyA (i.p.) or SmPill (CyA), the levels of all three inflammatory cytokines in the colons of these mice were also reduced relative to other groups of animals (FIG. 18). Compared to the untreated animals, SmPill (CyA)-treated mice had a significant reduction in TNF-α and IL-1β (P<0.05), whereas treatment with CyA (i.p.) reduced the colon levels of IL-113 but not TNF-α (FIG. 18A, B). There was no statistical significant difference in IL-17 levels detected in the colons between groups (FIG. 18C).

Figure 19:
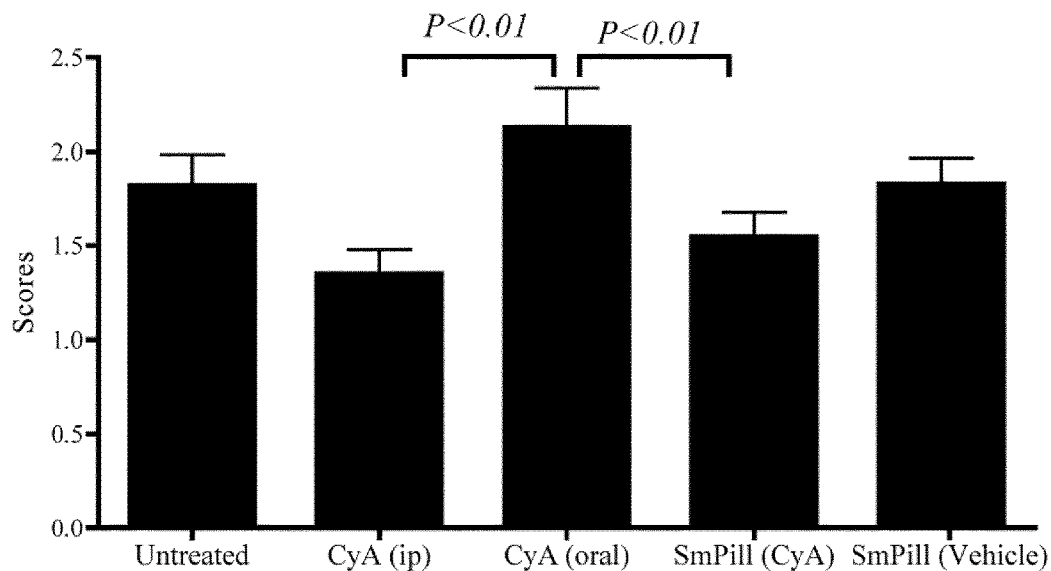
FIG. 19 is a bar chart showing histology scores of proximal colons of IL-10-/- mice with different treatment regimes (see Example 5)

The proximal colon was removed at termination and Haematoxylin and Eosin stained sections prepared. Scoring of colons demonstrated comparable degrees of mild inflammation in all groups, with CyA (Oral) having the greatest relative score (FIG. 19). CyA (i.p.) and SmPill (CyA) groups of mice had significantly lower (P<0.01) histology scores relative to CyA (Oral), but not other groups (FIG. 19)

Figure 20A:
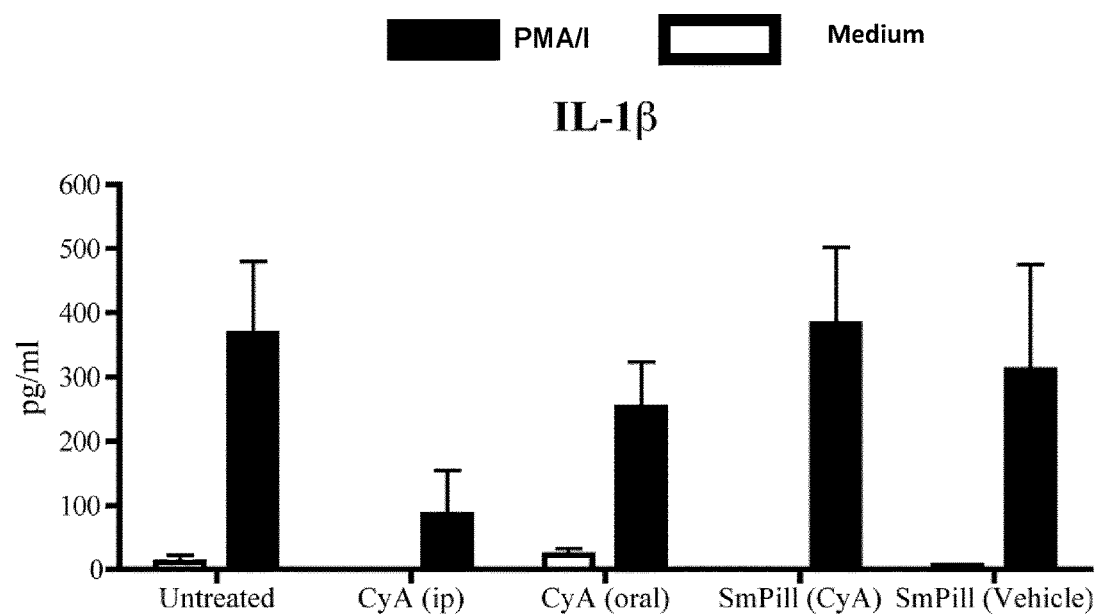
FIGS. 20A, 20B and 20C are bar charts showing the in vitro production of cytokines IL-1β, TNF-α and IL-17 by spleen cells from IL-10-/- mice with different treatment regimes (see Example 5)
Figure 20B:
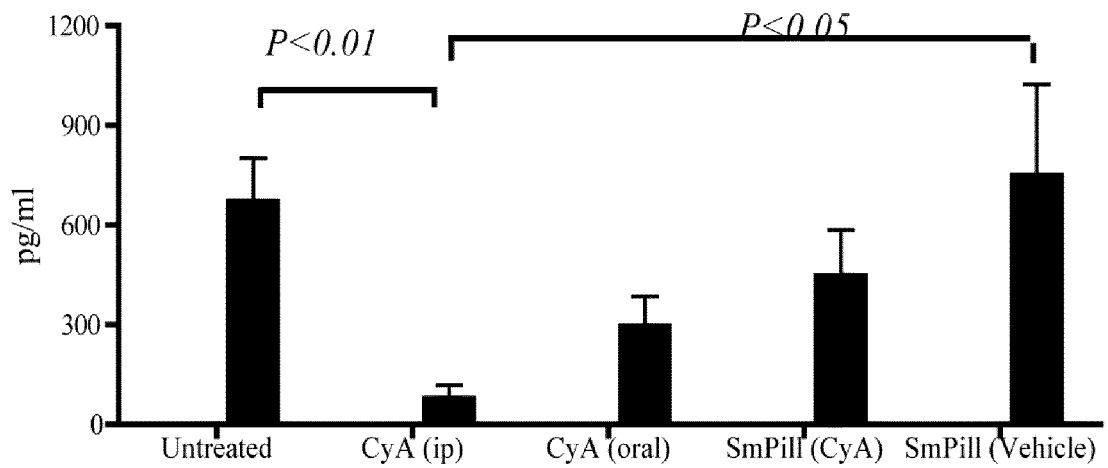
Figure 20C:
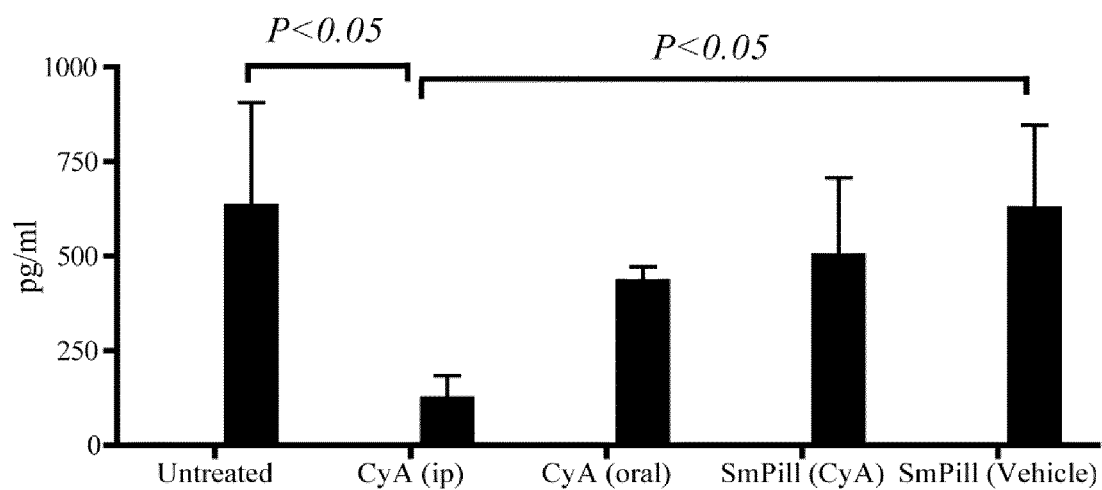

To address systemic effects of drug treatment in IL-10−/− mice, the spleens were removed at termination from 4 mice per group, selected 1-4 in order from the numeric coding system, and spleen cells were cultured in vitro. The production of the three cytokines that were measured in the colon (IL-1β, IL-17 and TNF-α) were assessed in spleen cells that were unstimulated (cultured in media) or non-specifically activated by PMA/I treatment. Following in vitro stimulation spleen cells from CyA (i.p.)-treated mice has significantly reduced production of TNF-α and IL-17 relative to cells from untreated and SmPill (Vehicle)-treated mice (FIG. 20). There were non-significant reductions in IL-17 and TNF-α release by cells from other CyA-treated groups. The trend for reduced cytokine release from CyA (i.p.)-treated mice was reflected in IL-1β production, but there were no statistical differences between groups (FIG. 20).

Example 6

Mouse Model of Fibrosis

The chosen animal model uses dextran sodium sulphate (DSS) to induce inflammation of the colon, followed by a recovery phase to allow the development of fibrosis. The mice are treated with various formulations during the recovery phase to evaluate the effectiveness of test formulations on controlling clinical manifestations of disease. Inflammation of the colon is induced using 2.5% DSS in drinking water.

Measurement of induction of inflammation is by determining the disease activity index (DAI). See Clinicopathologic study of dextran sulphate sodium experimental murine colitis, Lab Invest, 69, 238-49. Cooper, H. S., Murthy, S. N., Shah, R. S, and Sedergran, D. J. (1993).

TABLE 1

Scoring of disease activity index.

| Score | Weight loss | Stool consistency | Blood in feces |
|---|---|---|---|
| 0 | None | Normal | None |
| 1 | 1-5% | | |
| 2 | 5-10% | Loose | Hemoccult+ |
| 3 | 10-20% | | |
| 4 | >20% | Diarrhoea | Gross bleeding |

The disease activity index is calculated as the sum of scores of weight loss, stool consistency and blood in faeces.

Normal stool=formed pellets
loose stool=pasty and semiformed stool which do not stick to the anus
diarrhoea=liquid stools that stick to the anus.

Colon Weight: The colon is emptied of the fecal matter and weight of each colon is recorded.

Colon Length: The length of each colon is recorded.

Colon Histology: Approximately 10 mm of mid-colon is fixed in 10% buffered formaline and paraffin embedded. 4 μm sections were stained with Hematoxyline and Eosin stain to determine the degree of inflammation and Masson trichrome stain for evaluation of fibrosis. The stained sections were examined under light microscopy.

Procedures Carried Out

DSS Induced Fibrosis: DSS (Dextran sodium sulfate; 2.5%) is present in the drinking water of the mice for 5 days duration, on day 5 the DSS was stopped in drinking water and the treatment groups were treated with various test formulations for 14 days. A normal recovery group did not receive any drug.

This is a standard model for Fibrosis: Kenji Suzuki et al Pathology International 2011; 61: 228-238. At the end of the experiment, the mice are euthanized by standard cervical dislocation. To monitor disease progression, disease activity index (DAI) is determined as discussed above.

Administration of Minibeads: The minibeads are administered using a stainless steel oral gavage needle. Two minibeads are lodged into the free end of the gavage needle and are administered orally to the mice along with 0.1 ml saline using standard 1 ml syringe.

The following dosages were administered in beads similar to those of Example 2:

CyA formulation: ~0.629 mg CyA per 2 bead dose
HyA formulation: ~0.708 mg HyA per 2 bead dose
CyA/HyA formulation: ~0.710 mg CyA and ~0.780 mg HyA per 2 bead dose.

Figure 21:
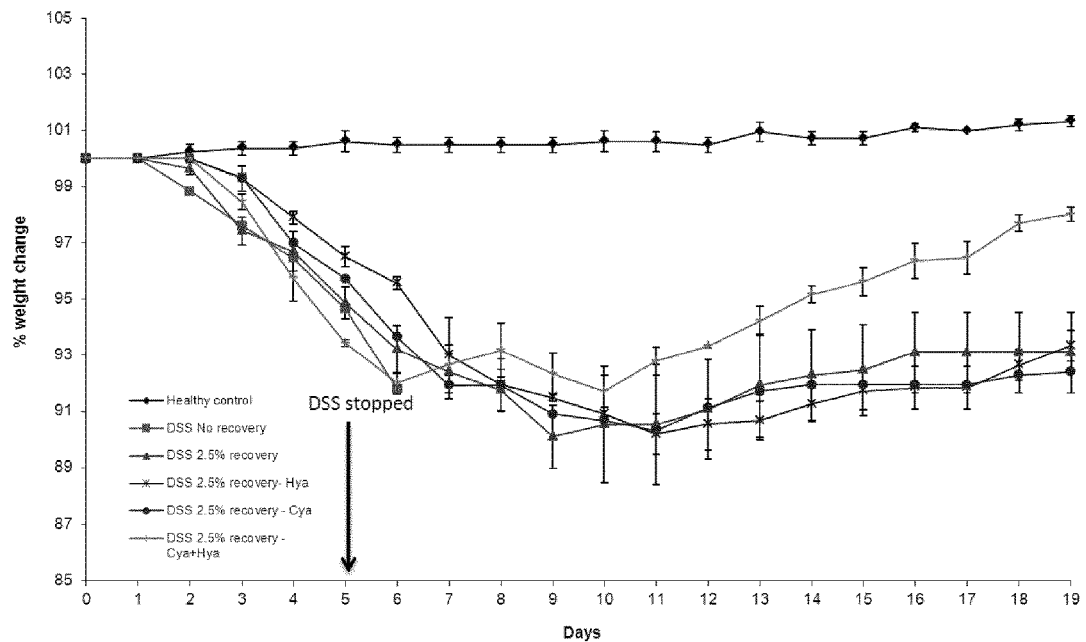
FIG. 21 is a graph showing % weight change resulting from different treatment regimes in a DSS model of intestinal fibrosis in mice (see Example 6)
Figure 22:
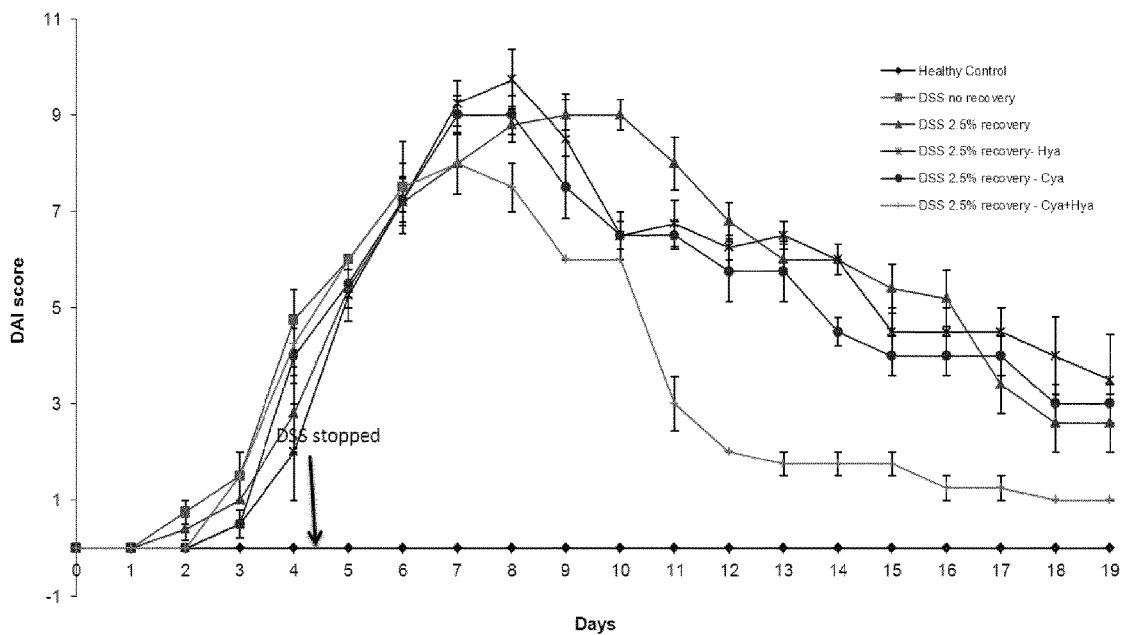
FIG. 22 is a graph showing change of DAI resulting from different treatment regimes in the DSS model of intestinal fibrosis in mice (see Example 6)
Figure 23:
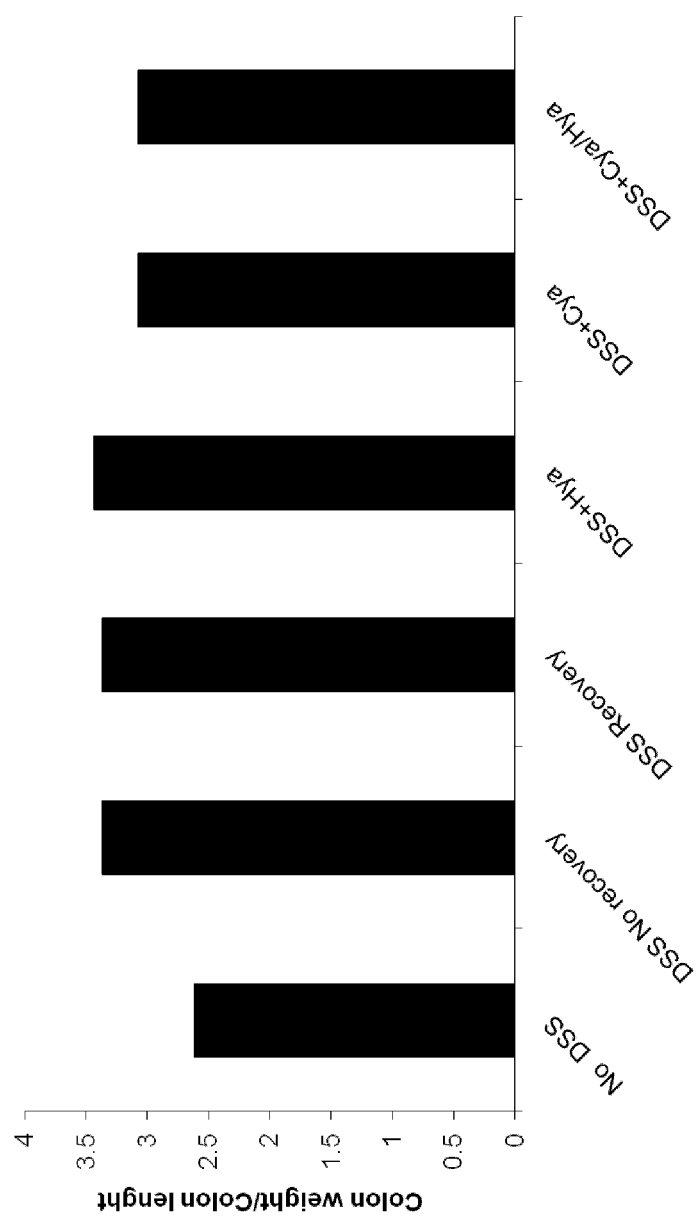
FIG. 23 is a bar chart showing the ratio of colon weight: colon length resulting from different treatment regimes in the DSS model of intestinal fibrosis in mice (see Example 6)
Figure 32:
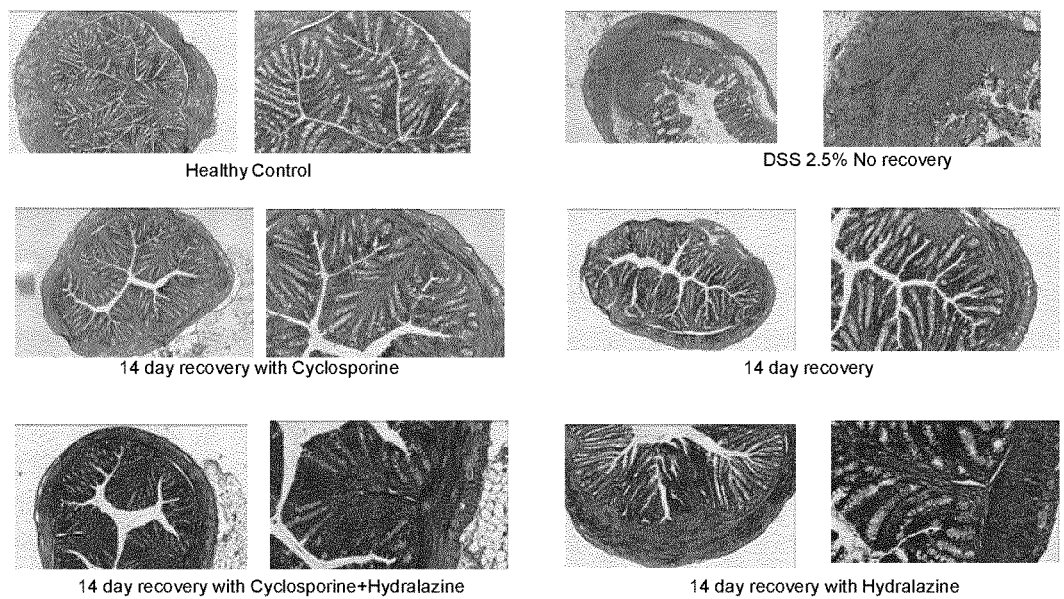
FIG. 32 comprises histology slides showing the effect of different treatment regimes in the DSS model of intestinal fibrosis in mice to which FIGS. 21-23 relate (see Example 6)

The results are shown in FIGS. 21-23. The histology of the colonic tissue shown in FIG. 32 suggests that the Hya+Cya formulation containing a high level of hydralazine is more protective in DSS-induced colitis than the formulation containing a low level of hydralazine.

Example 7

Mouse Model of Colitis with High and Low Ratio HyA:Cya Combinations

The same animal model is used and the same procedure followed as in Example 1.

The following combination dosages of hydralazine and cyclosporin A were administered in combination beads similar to those of Example 2:

Low level of HyA: ~0.730 mg CyA and ~0.550 mg HyA per 2 bead dose
High level of HyA: ~0.710 mg CyA and ~0.780 mg HyA per 2 bead dose.

Figure 24:
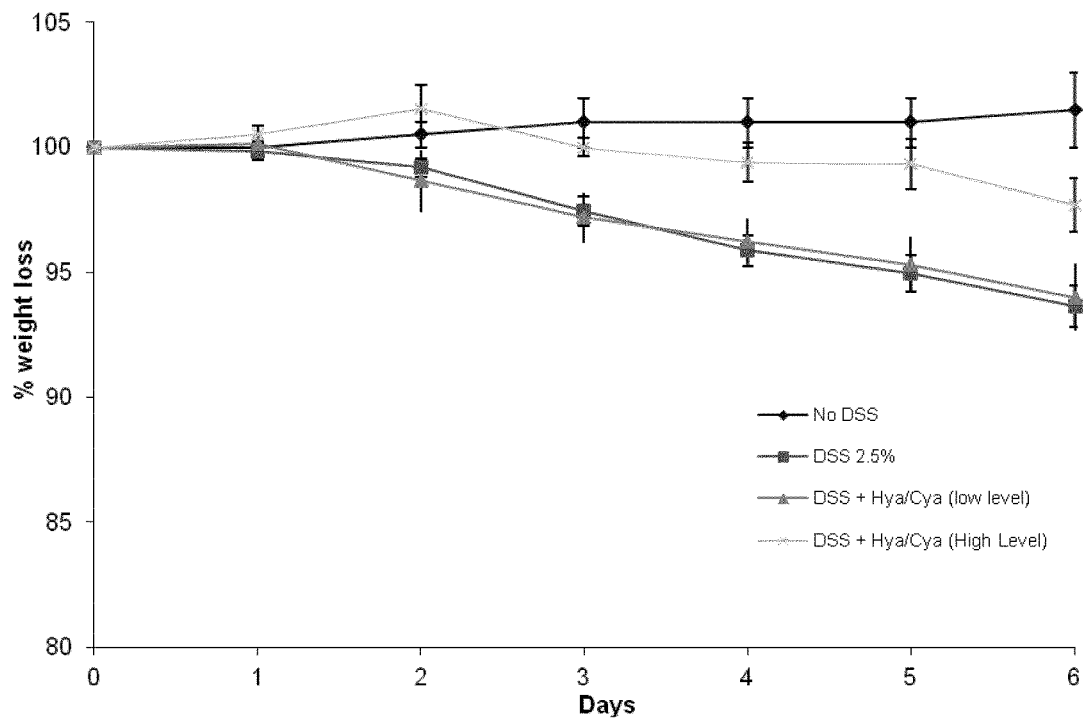
FIG. 24 is a graph showing % weight change resulting from treatment with formulations containing different proportions of hydralazine and ciclosporin in a DSS model of colitis in mice and wherein "Hya" means hydralazine and "Cya" means cyclosporin A (also known as ciclosporin) (see Example 7)
Figure 25:
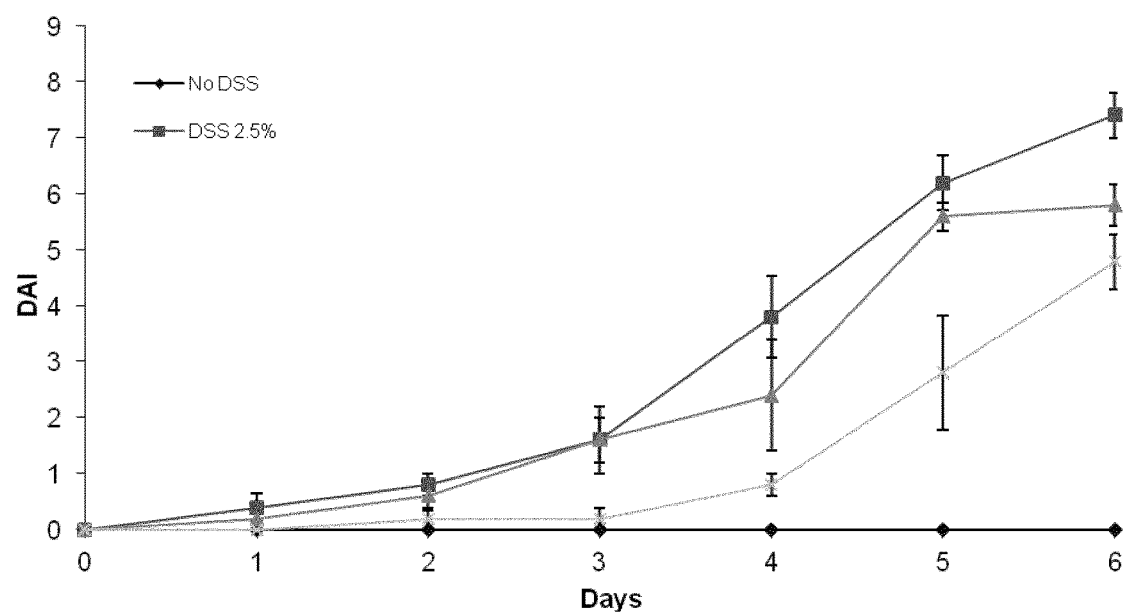
FIG. 25 is a bar chart showing change of DAI resulting from treatment with formulation containing different proportions of hydralazine and ciclosporin in the DSS model of colitis in mice and wherein "Hya" means hydralazine and "Cya" means cyclosporin A (see Example 7)
Figure 26:
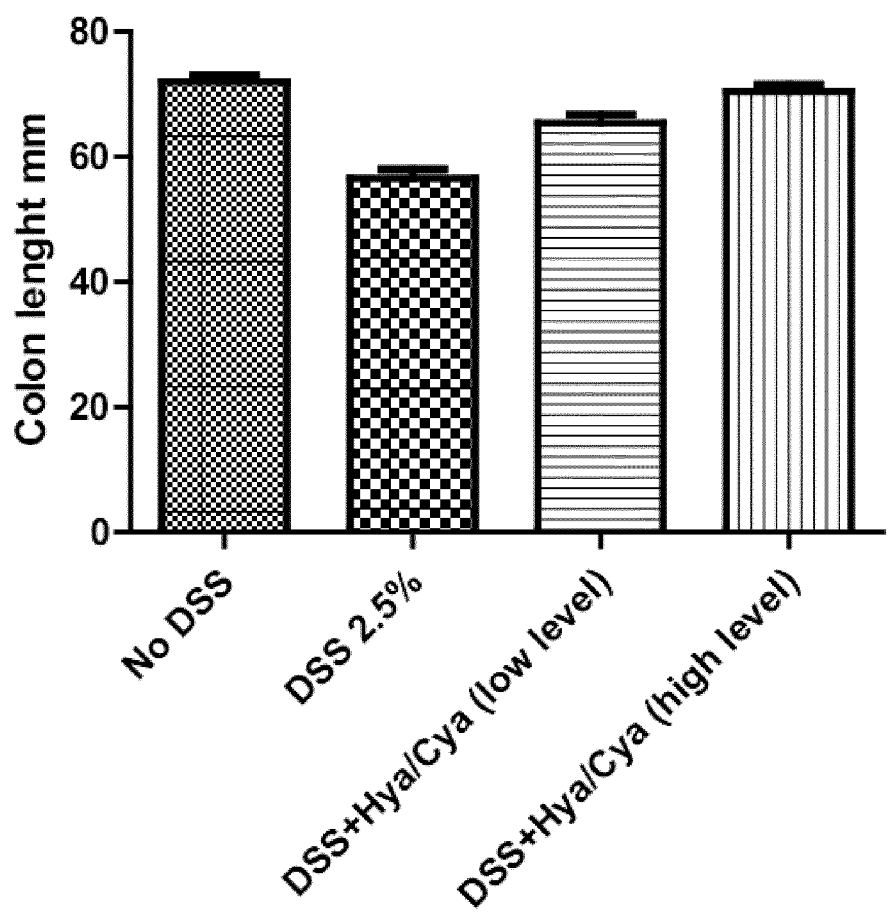
FIG. 26 is a bar chart showing the ratio of colon weight: colon length resulting from treatment with formulation containing different proportions of hydralazine and ciclosporin in the DSS model of colitis in mice and wherein "Hya" means hydralazine and "Cya" means cyclosporin A (see Example 7).
Figure 27:
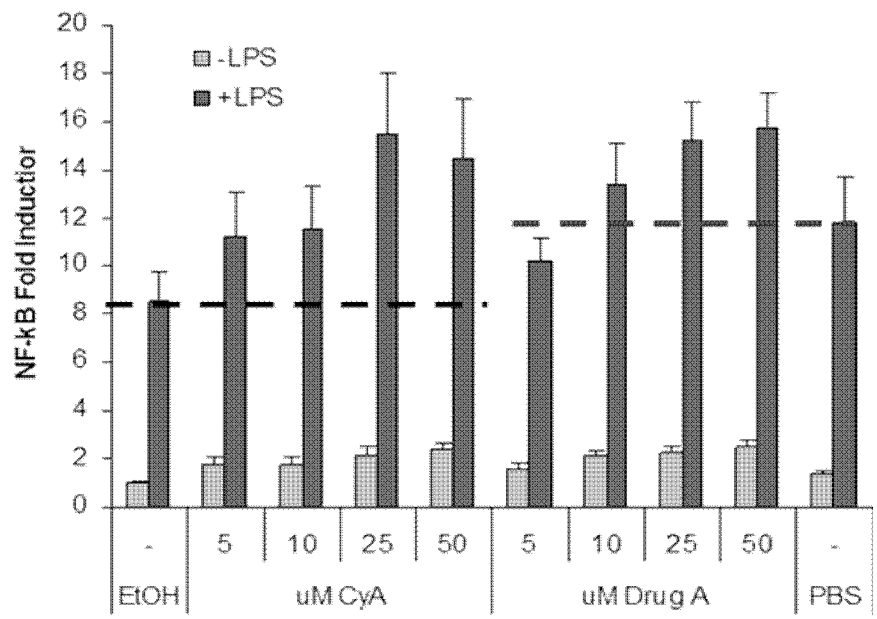
FIG. 27 shows the effects on LPS-induced activations of NFκB by cyclosporin A and hydralazine (drug A)
Figure 28:
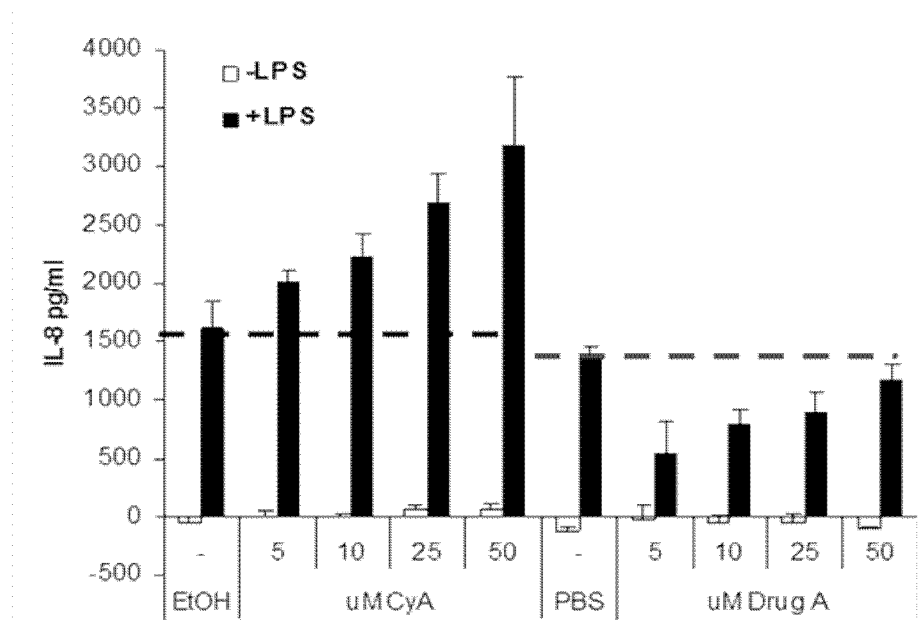
FIG. 28 shows the effects on LPS-induced activation of IL-8 by cyclosporin A, hydralazine (drug A)
Figure 33:
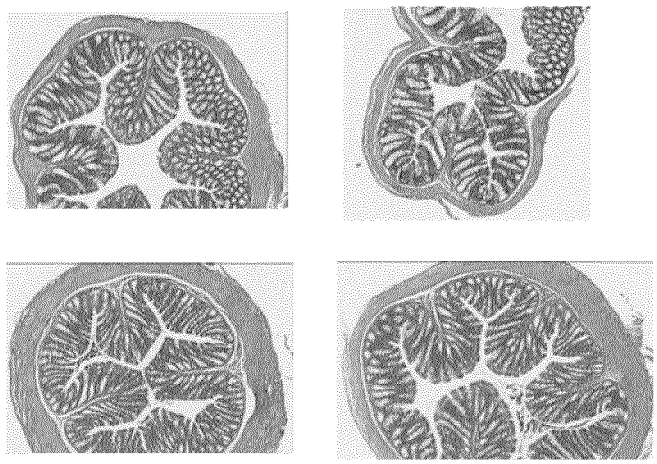
FIG. 33 comprises slides showing the histology of healthy control specimens of colonic tissue in the DSS model of colitis in mice to which FIGS. 24-26 relate (see Example 7)
Figure 34:
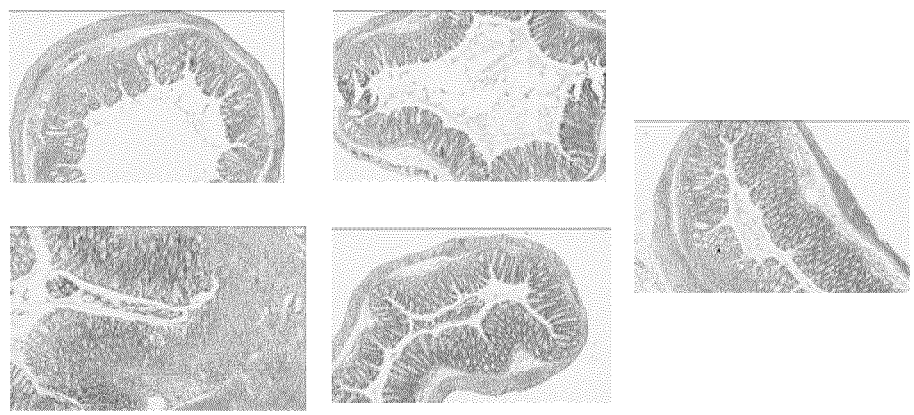
FIG. 34 comprises slides showing the histology of DSS control specimens of colonic tissue in the DSS model of colitis in mice to which FIGS. 24-26 relate (see Example 7)
Figure 35:
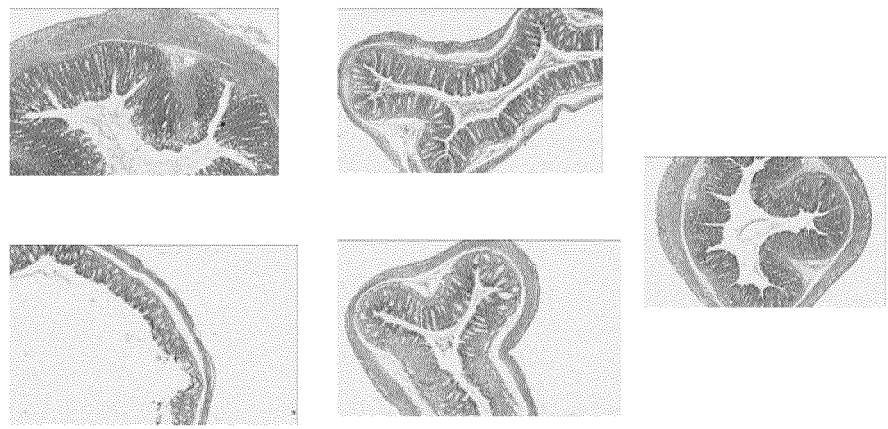
FIG. 35 comprises slides showing the histology of specimens of colonic tissue from mice treated with "low level" hydralazine/cyclosporin A combination minibeads in the DSS model of colitis in mice to which FIGS. 24-26 relate (see Example 7)
Figure 36:
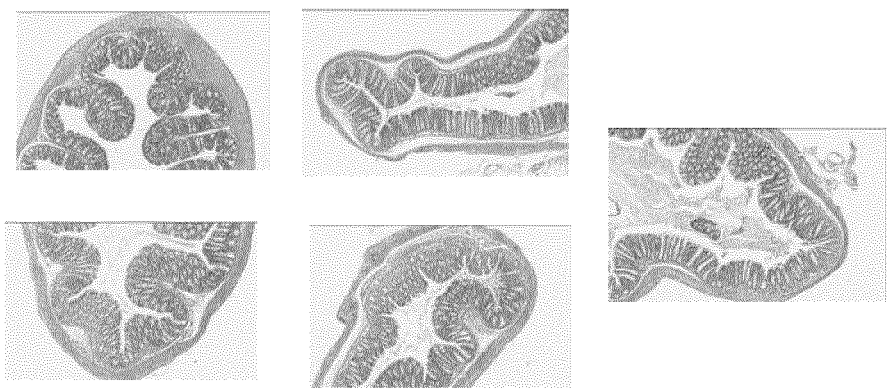
FIG. 36 comprises slides showing the histology of specimens of colonic tissue from mice treated with "high level" hydralazine/cyclosporin A combination minibeads in the DSS model of colitis in mice to which FIGS. 24-26 relate (see Example 7)

In the "low level" minibeads, the weight ratio of HyA:CyA was about 0.75:1. In the "high level" minibeads, the weight ratio of HyA:CyA was about 1.1:1. The results are shown in FIGS. 24-26. The histology of the colonic tissues in FIGS. 33-36 suggests that the Hya+Cya formulation containing a high level of hydralazine is more protective in DSS-induced colitis than the formulation containing a low level of hydralazine. FIG. 33 comprises slides showing the histology of healthy control specimens. FIG. 34 comprises slides showing the histology of DSS control specimens. FIG. 35 comprises slides showing the histology of specimens of colonic tissue from mice treated with "low level" hydralazine/cyclosporin A combination minibeads. FIG. 36 comprises slides showing the histology of specimens of colonic tissue from mice treated with "high level" hydralazine/cyclosporin A combination minibeads Example 8

The aim of the experiment is to prove the stability of Hydralazine HCl and Cyclosporin A formulated (minibead) form and determine a relation between dose of drugs and NFκB activation. The experiment was performed by comparing different formulated drug concentrations with equivalent concentrations of unformulated drug; activation of NFκB was measured through NRE-Luciferase in HeLa cells after drug treatment.

6 different concentrations for Hydralazine HCl and 6 different concentrations for Cyclosporin A were used. The following formulations were made according to the procedure of Example 1 and dissolved to provide solutions containing the 6 different concentrations of active HyA Formulation

| Component | % w/w |
|---|---|
| Hydralazine | 4.47 |
| Transcutol P | 18.10 |
| Miglyol 810N | 4.95 |
| Cremophor EL | 9.88 |
| Gelatin | 52.14 |
| D-Sorbitol | 5.98 |
| SDS | 4.47 |

CyA Formulation

| Component | % w/w |
|---|---|
| Cyclosporine | 10.87 |
| Miglyol 810N | 4.64 |
| Transcutol P | 16.55 |
| Cremophor EL | 9.28 |
| Gelatin | 49.02 |
| SDS | 4.00 |
| D-Sorbitol | 5.64 |

Combination

| Component | % w/w |
|---|---|
| Cyclosporine | 10.06 |
| Hydralazine | 4.10 |
| Transcutol P | 15.79 |
| Miglyol 810N | 4.32 |
| Cremophor EL | 8.63 |
| Gelatin | 47.58 |
| D-Sorbitol | 5.45 |
| SDS | 4.08 |

The solutions of formulated Hydralazine HCl and Cyclosporin A (Sigmoid Pharma) were diluted at different concentrations with complete DMEM medium (Dulbecco). Stock solutions of Hydralazine HCl and Cyclosporin A were prepared by dissolving drug powder. Hydralazine HCl was dissolved in complete DMEM medium (Dulbecco), 1600 µg/mL. Cyclosporin A was dissolved in ethanol, 100 mg/mL. The solutions were then filtered using a 0.2 µm microfilter and diluted with DMEM medium (Dulbecco) to equivalent concentrations of the formulated drug solutions.

HeLa cells were grown in 6-wells plates in order to have 60-70% confluent wells. Each cell well was then transfected with 200 ng NRE-Luc DNA plasmid and 100 ng β-Galactin DNA plasmid using Lipofectamine transfection. After 24 hours, to each well (1 mL) 1 mL of different Hydralzine HCl and Cyclosporin A solutions were added. The cells were incubated at 37° C. and 5% $CO_2$ for 5 hours.

After incubation, HeLa cells were washed with cold PBS and incubated for 5 minutes at RT with 1X luciferase lysis buffer (Promega). The lysate were then scraped from the well and resuspended into a 1.5 mL tube. The lysed cells were then centrifugated for 5 minutes at 12'000 rpm and RT. The supernatant was collected in a new tube. The lysate was then analyzed using an NRE Luciferase assay in order to quantify the NFκB expression. The measured RLU values were then normalized using the β-galactosidase assay.

The measurement of Luciferase was repeated 3 times per each sample in order to have a statistically significant result and the RLU values were represented in a column graphic with 95% confidential interval.

Figure 29:
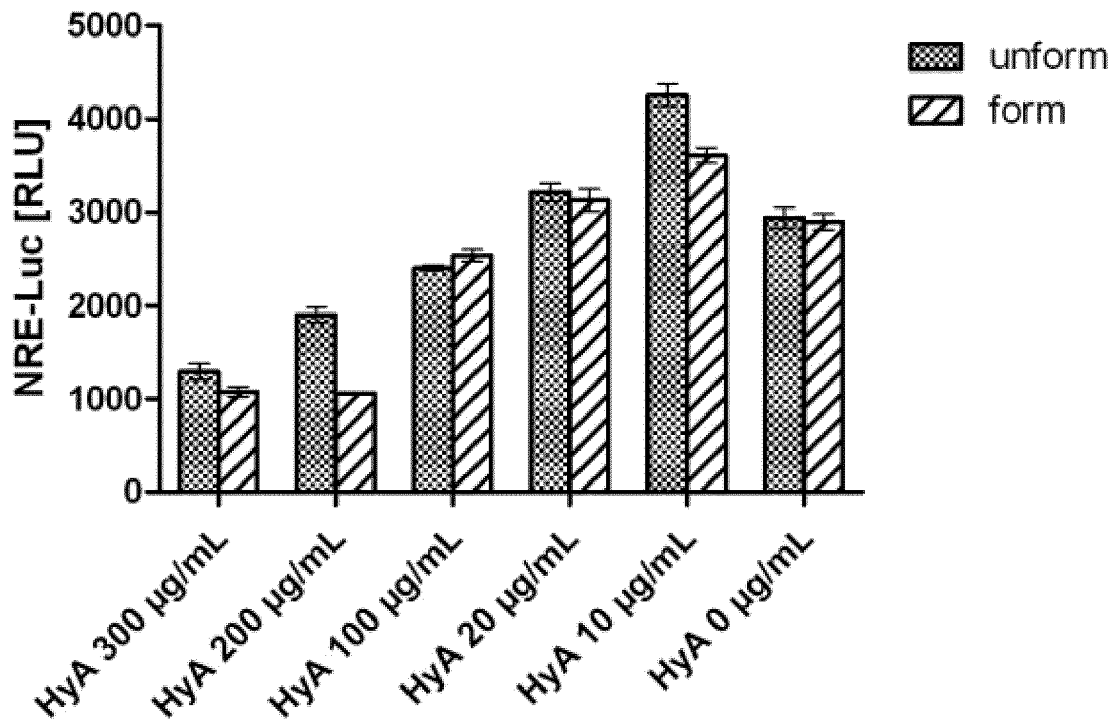
FIG. 29 is a bar chart showing normalised values of NFκB activation attained by formulated and unformulated hydralazine as measured using an NRE-luciferase assay.
Figure 30:
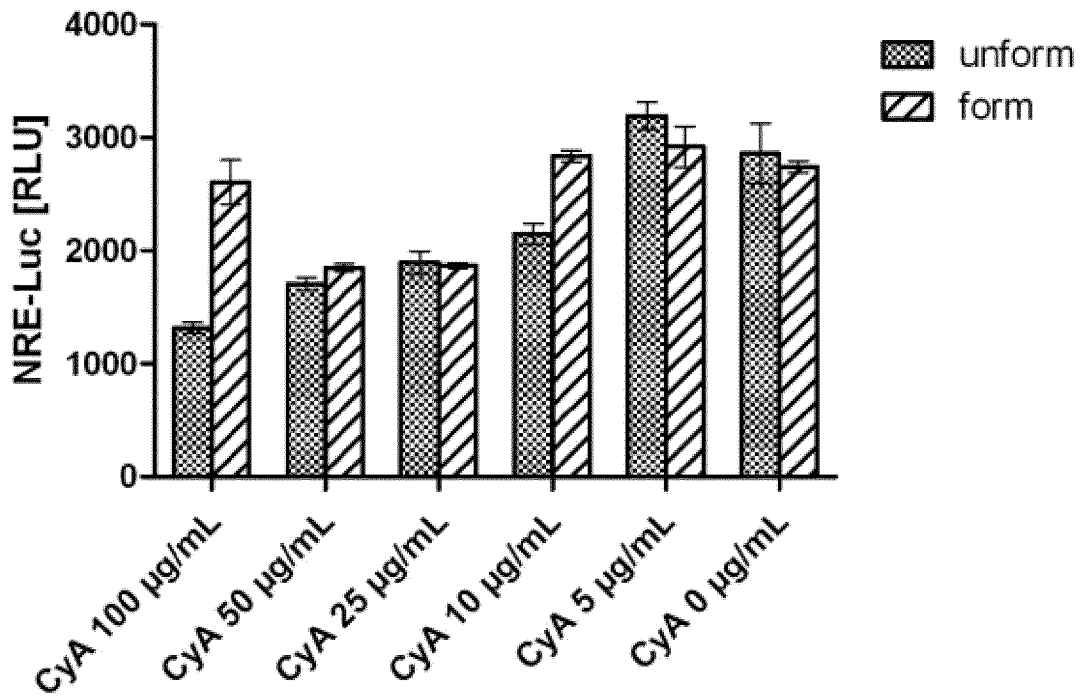
FIG. 30 is a bar chart showing normalised values of NFκB activation attained by formulated and unformulated cyclosporin A as measured using an NRE-luciferase assay.
Figure 31:
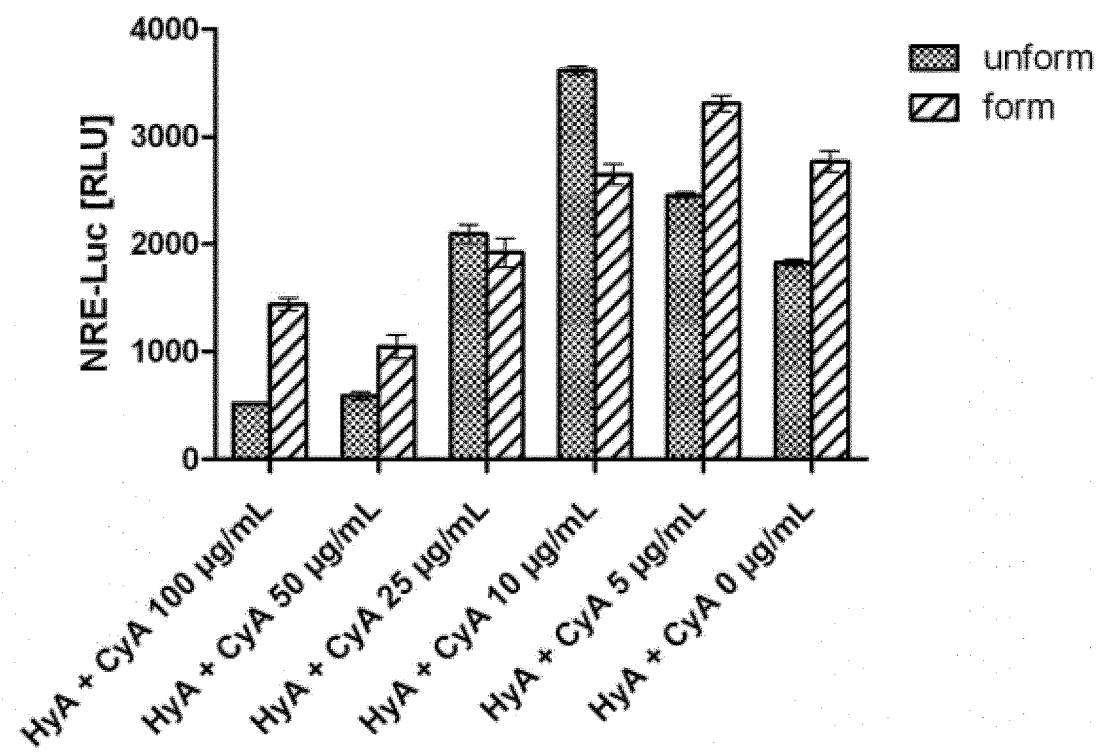
FIG. 31 is a bar chart showing normalised values of NFκB activation attained by formulated and unformulated combination of hydralazine and cyclosporin A.

The results are shown in FIGS. 29, 30 and 31, where the legend "unform" refers to unformulated active and the legend "form" refers to formulated (minibead) active. The concentrations which appear in FIG. 31 are expressed as the concentration of hydralazine.

Example 9

The aim of the experiment is to prove the stability of Hydralazine HCl and Cyclosporin A formulated (minibead) form and determine a relation between dose of drugs and HIF-1α activation. The experiment was performed by comparing different formulated drug concentrations with equivalent concentrations of unformulated drug; activation of HIF-1α was detected through Western Blot in CaCo2 cells after drug treatment.

The minibead formulations made according to the procedure of Example 1.

6 different concentrations of Hydralazine HCl and 6 different concentrations of Cyclosporin A were used. The minibead formulations used were the same as in Example 8.

Solutions of formulated (SmPill) Hydralazine HCl and Cyclosporin A (Sigmoid Pharma) were diluted at different concentrations with complete DMEM medium (Dulbecco). Stock solutions of Hydralazine HCl and Cyclosporin A were prepared by dissolving drug powder. Hydralazine HCl was dissolved in complete DMEM medium (Dulbecco), 1600 µg/mL. Cyclosporin A was dissolved in ethanol, 100 mg/mL. The solutions were then filtered using a 0.2 µm microfilter and diluted with DMEM medium (Dulbecco) to equivalent concentrations of the formulated drug solutions.

Caco2 cells were grown in 6-wells plates in order to have 60-70% confluent wells. To each well (1 mL) 1 mL of different Hydralazine HCl and Cyclosporin A solutions were added. The cells were incubated at 37° C. and 5% CO2 for 5 hours.

After incubation, cells were washed with cold PBS and incubated for 5 minutes on ice with "whole cell lysis buffer" (*M. Tumbuwala*). The lysate were then scraped form the well and resuspended into a 1.5 mL tube. The lysed cells were then centrifugated for 5 minutes at 12'000 rpm and 4° C. The supernatant was collected in a new tube and the proteins concentration were determined using Biorad protein assay kit (Sigma). 5 µL of lysate of each sample were added in each well of a 96 well plate, then 25 µL of solution A and 200 µL of solution B were added to the samples. The absorbance was read at 595 nm with reference filter at 450 nm and the concentration of protein was measured using a standard curve. Protein concentration of lysate samples was then normalized at 871 µg/mL.

5x Laemmli buffer (Laemmli) was added to normalized proteins and the protein samples were denatured by heating at 100° C. for 10 minutes. Protein samples were then loaded (20 µL/slot) and separated on a vertical dual-slab minigel system (Biorad) using a 7.5% acrylamide stacking gel. Electrophoresis was carried out at a voltage of 90 V for 2 hours. A protein marker (BioLabs) was used.

After protein separation, the gel was removed from the chamber and placed in chilled transfer buffer. Whatman paper and nitrocellulose membrane (Biorad) were also moistened in chilled transfer buffer. The blot-sandwich was assembled with, first a Whatman paper, second the nitrocellulose membrane, then the gel and finally a second Whatman paper. The proteins were transferred onto the nitrocellulose membrane using a tank transfer system (Biorad) placed on ice at a constant voltage of 100 V for 90 minutes. After the transfer, the membrane was stained with Ponceau S solution (Sigma) to confirm the successful transfer of the proteins. The membrane was then washed in PBST for 5 minutes to remove the Ponceau S solution. The membrane was blocked during 1 hour by incubation with 10% milk (Not fat dry milk (Fluka) in PBST). Then the membrane was incubated with the first antibody (Purified Mouse Anti-Human HIF-1a (BD Transduction laboratories), concentration 1/750 in 10% milk) over night at 4° C. The membrane was then washed 4 times with PBST for 5 minutes followed by incubation with the secondary antibody (Anti-Mouse IgG HRP Conjugate (Promega), concentration 1/2000 in 10% milk) for one hour. The membrane was again washed 6 times in PBST for 5 minutes. 3 mL of ECL reagent pro membrane were prepared. The membrane was carefully dried, covered with ECLplus reagent on a clean surface and incubated for 5 minutes at room temperature. The membrane was dried as before, placed into a film case and exposed to a X-ray film with exposition time of 6 seconds. After development the membrane was washed with water and stored in PBST at 4° C.

The exposed films were analyzed by comparing the bands with the protein marker. The bands of HIF-1α were identified according to its molecular weight of 120 kDa.

Figure 37:
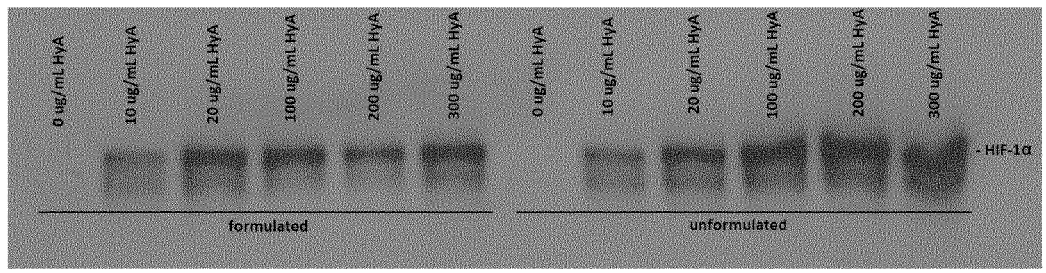
FIG. 37 is a photograph of a nitrocellulose membrane stained to show HIF-1α from a lysate of Caco2 cells incubated with hydralazine HCl (see Example 9)

The cells were treated with hydralazine at concentrations in µg/mL of 0, 10, 20, 100, 200 and 300. The results of the Hydralazine treated cells in FIG. 37 show an increase of HIF-1α expression proportional to the drug concentration between 0 and 100 µg/mL and a stabilization of the expression between 100 and 300 µg/mL in both formulated and unformulated groups. These results show an up-regulation of HIF-1α related to Hydralazine concentration and a stability of the formulated drug.

Figure 38:
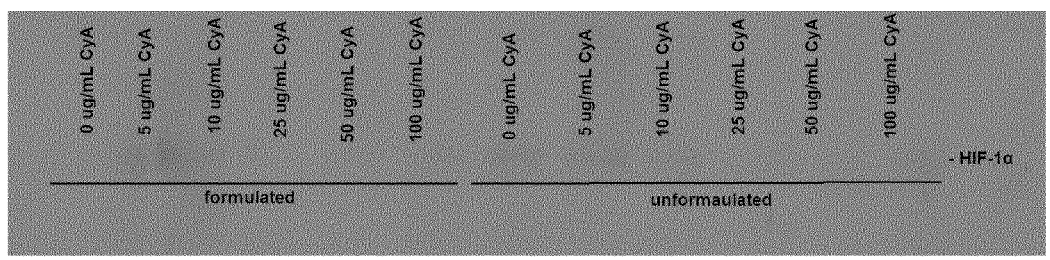
FIG. 38 is a photograph of a nitrocellulose membrane stained to show HIF-1α from a lysate of Caco2 cells incubated with cyclosporin A (see Example 9)

The cells were treated with cyclosporin A at concentrations in µg/mL of 0, 5, 10, 25, 50 and 100. The expression of HIF-1α on cells treated with Cyclosporin A is only slightly detectable at this exposure time indicating a low influence of this drug on regulation of HIF-1α expression, as can be seen in FIG. 38.

Figure 39:
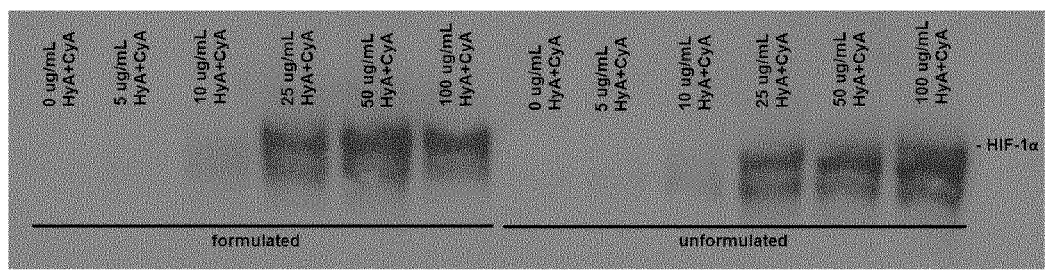
FIG. 39 is a photograph of a nitrocellulose membrane stained to show HIF-1α from a lysate of Caco2 cells incubated with a combination of hydralazine HCl and cyclosporin A (see Example 9).

The cells were treated with a combination of cyclosporin A and hydralazine at concentrations in µg/mL of 0, 5, 10, 25, 50 and 100 expressed as the concentration of hydralazine. In relation to cells treated with both Hydralazine HCl and Cyclosporin A, the results in FIG. 39 show a marked up-regulation of HIF-1α at 25, 50 and 100 µg/ml, which is not at all found with the CyA treatment. The greater influence of Hydralazine HCl on the HIF-1α activation is clearly recognizable. To note is that the signals of formulated drug is slightly stronger of that of unformulated drug. This could indicate a better stability of the combined drugs in the formulated form, thanks to the delivery in different phases.

Remarks

Hydralazine increases HIF-1α expression in a dose dependent manner indicating that hydralazine may act as an hydroxylase inhibitor (Novel Mechanism of Action for Hydralazine: Induction of Hypoxia-Inducible Factor-1 alpha, Vascular Endothelial Growth Factor, and Angiogenesis by Inhibition of Prolyl Hydroxylases. Helen J. Knowles, Ya-Min Tian, David R. Mole, Adrian L. Harris. Circ. Res. published online Jun. 10, 2004). Referring to Example 2 this mechanism may provide an explanation for hydralazine-induced protection in DSS in-vitro and DSS induced murine model of colitis. The beta-actin band indicates that equal amounts of protein were loaded in each lane.

The formulations of Example 2 with the higher HyA/CyA combination not only provide overall protection (both DAI and Wt Loss) but confer more protection at an earlier stage. This implies that improved barrier function may assist in the maintenance of intestinal epithelial functions and protect from the damage induced by DSS. In so doing, the irritation is reduced and therefore the intestinal mucosa is less likely to suffer from inflammation. Nothing completely protects cells from DSS damage but the HyA protection is an important phenomenon. Without being bound by theory, it is envisaged that, when the barrier function has been compromised, the presence of CyA will reduce inflammation.

The observations of Example 2 are supplemented by those of Example 9, showing HyA and HyA/CyA but not CyA alone up-regulate HIF-1α expression.

The above is supported by the TEER observations. As noted, the DSS causes severe damage to the epithelial barrier. HyA provides protection from this damage.

Importantly, HyA is much more effective when delivered from the intestinal lumen by a minibead than when administered orally or administered by i.p. injection.

Overall, the combination treatment both protects the epithelial barrier and suppresses inflammation when administered locally.

However, monotherapy with cyclosporin is also shown to be effective in controlling manifestations of colitis and is indicated as potentially therapeutically effective (alone or in combination therapy) to treat disorders in which a "leaky intestine" is, or may be, implicated.

Example 5 shows that local delivery of a macrolide immunosuppressant, in this case ciclosporin, to the colon achieves differential modulation of colonic and systemic cytokines. In other words, such local delivery preferentially inhibits cytokine expression in the colon to achieve a local anti-inflammatory effect without the same undesirable systemic immunosuppression achieved by comparative formulations Sandimmun® and Neoral® which do not have a controlled release function. The coated beads used in the examples achieve colonic targeting by inclusion in a polymer coat of a polymer which degrades in the presence of bacterial enzymes present in the colon, specifically pectin; a pH-independent polymer, specifically ethylcellulose is included in the coating also. The invention therefore contemplates the use of dosage units having a polymer coating comprising a delayed release polymer and a polymer which degrades in the presence of bacterial enzymes present in the colon.

The invention claimed is:

1. An oral pharmaceutical composition comprising hydralazine and cyclosporin A in a weight ratio (hydralazine:cyclosporin A) of from 0.8:1 to 5:1, wherein the composition is a multiple minibead composition and the hydralazine and cyclosporin A are contained in the minibeads, each minibead comprising a water-soluble polymer matrix material and, dispersed within the matrix material, a hydrophobic phase, the matrix material comprising the hydralazine and the cyclosporin A being dissolved in the hydrophobic phase, at least some of the minibeads having a controlled release coating adapted for the coated minibeads to release hydralazine and cyclosporin A in at least the colon.

2. The pharmaceutical composition of claim 1 wherein the weight ratio is from 0.8:1 to 2:1.

3. The pharmaceutical composition of claim 2 wherein the weight ratio is from 1:1 to 2:1.

4. The pharmaceutical composition of claim 1 which is a for oral administration.

5. The pharmaceutical composition of claim 1 wherein the matrix material comprises a hydrophilic surfactant having an HLB value of at least 15 and the hydrophobic phase comprises a non-ionic surfactant having an HLB value of at least 10 but less than that of the hydrophilic surfactant.

6. The pharmaceutical composition of claim 1 wherein the coated minibeads are coated with a coating comprising a pH independent polymer and a polymer specifically susceptible of degradation by bacterial enzymes in the colon.

7. The pharmaceutical composition of claim 6 wherein the pH independent polymer is ethylcellulose and the polymer specifically susceptible of degradation by bacterial enzymes in the colon is a polysaccharide.

8. The pharmaceutical composition of claim 1 wherein the minibeads are coated with additional drug layers, wherein the drug layer is part of the coating or independent thereof.

* * * * *